(12) United States Patent
Kindon et al.

(10) Patent No.: US 6,218,376 B1
(45) Date of Patent: Apr. 17, 2001

(54) URACIL COMPOUNDS AS P2-PURINORECEPTOR 7-TRANSMEMBRANE G-PROTEIN COUPLED RECEPTOR ANTAGONISTS

(75) Inventors: Nicholas Kindon, Ashby de la Zouch; Premji Meghani; Stephen Thom, both of Loughborough, all of (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/202,140

(22) PCT Filed: Nov. 18, 1998

(86) PCT No.: PCT/SE98/02088

§ 371 Date: Dec. 9, 1998

§ 102(e) Date: Dec. 9, 1998

(87) PCT Pub. No.: WO99/26944

PCT Pub. Date: Jun. 3, 1999

(30) Foreign Application Priority Data

Nov. 21, 1997  (SE) ................................... 9704272

(51) Int. Cl.$^7$ .................. C07D 401/04; C07D 405/04; C07D 409/04; A61K 31/506; A61P 37/08

(52) U.S. Cl. .................. 514/86; 514/212.06; 514/215; 514/235.8; 514/236.2; 514/236.5; 514/236.8; 514/274; 514/295; 540/521; 544/123; 544/243; 544/295; 544/310; 544/311; 544/314

(58) Field of Search .................. 514/274, 215, 514/235.8, 236.2, 236.5, 236.8, 295, 86, 212.06; 544/310, 311, 123, 243, 295, 314; 540/521

(56) References Cited

FOREIGN PATENT DOCUMENTS

97/08170    3/1997   (WO) .

OTHER PUBLICATIONS

Williams, M. et al, "Ann. Reports Med. Chem, vol. 31", 1996, Academic Press, San Diego, pp. 21–30.*

* cited by examiner

Primary Examiner—Mukund J. Shah
Assistant Examiner—Thomas McKenzie
(74) Attorney, Agent, or Firm—Nixon & Vanderhye

(57) ABSTRACT

Compounds of formula I or salts thereof

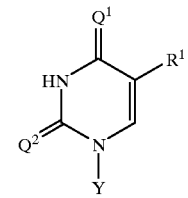
(I)

where for example Y is a group of the formula (i)

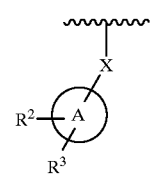

(i)

and $R^1$ is a group of formula (ii)

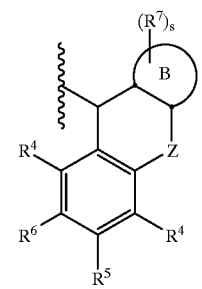

(ii)

are provided along with compositions containing them and processes for their preparation. The compounds are P2-purinoreceptor 7-transmembrane G-protein coupled receptor antagonists, and are useful in the treatment of inflammatory conditions.

16 Claims, No Drawings

URACIL COMPOUNDS AS P2-PURINORECEPTOR 7-TRANSMEMBRANE G-PROTEIN COUPLED RECEPTOR ANTAGONISTS

This application is the National Stage Application of PCT/SE98/02088, which claims priority from Swedish application 9704272-5, filed Nov. 21, 1997 and Swedish application 9801397-2, filed Apr. 21, 1998.

The invention provides new pharmaceutically active compounds, compositions containing them and processes for their preparation. The compounds are useful in therapy because they are P2-purinoceptor 7-transmembrane (TM) G-protein coupled receptor antagonists.

ATP receptors have been shown to be present on a wide number of different cell types (Dubyak et al Am J Physiol (1993) 265, C577–C606). Neutrophils, monocytes and macrophages have been isolated from several species including humans and ATP and/or UTP have been shown to increase intracellular calcium levels. Activation of these receptors on leukocytes can either directly stimulate certain types of inflammatory response or can prime the effector cells to other inflammatory mediators in vivo. ATP can upregulate the expression of adhesion molecules (Freyer et al J Immun. (1988) 141, 580–586) which causes enhanced adhesion of circulating leukocytes to endothelial cells and their enhanced migration into the tissue space. ATP has also been shown to promote chemotaxis of both neutrophils and eosinophils (Verghese et al J. B. C. (1996) 271, 15597–15601 and Burders et al Blood (1993) 81, 49–55) which may promote an inflammatory response. ATP priming of neutrophils can also potentiate superoxide production (Seifert et al Eur J Biochem (1989) 181, 277–285). ATP receptors are also present on a number of other cell types such as chondrocytes, keratinocytes, microglia and goblet cells (Leong et al BBA (1994) 1201, 298–304; Pillai et al J Clin Invest (1992) 90, 42–51; Walz et al J Neuroscience (1993) 13, 4403–4411 and Abdullah et al Biochem J (1996) 316, 943–951). Stimulation of the receptors on these cells can stimulate or enhance inflammatory responses and antagonist of the receptor may therefore be of use in a number of inflammatory diseases such as asthma, inflammatory bowel disease, ARDS, psoriasis, rheumatoid arthritis, myocardial ischaemia, COPD, cystic fibrosis, atherosclerosis, restenosis, peridontal disease, septic shock, osteoarthritis and stroke. ATP receptors have also been reported on tumour cells (Dubyak et al J. Biol. Chem., (1985) 260, 10653–10661 and Wagner et al Gastroenterology, (1997), 112(4) suppl. page A1198) and may be involved in the development of cancer. Antagonists may therefore be useful in treatment of cancer.

The invention provides new pharmaceutically active compounds, compositions containing them and processes for their preparation. The compounds are useful in therapy as P2-purinoceptor-7-transmembrane (TM) G-protein coupled receptor antagonists.

It has now been found that a series of pyrimidine derivatives are useful as P2-purinoceptor 7-transmembrane (TM) G-protein coupled receptor antagonists. In a first aspect the invention therefore provides a compound of formula (I) or a salt thereof:

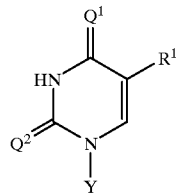

(I)

where

Y is hydrogen, $C_{1-4}$alkyl, $C_{1-4}$alkyl optionally substituted by hydroxy, alkoxy, amino, alkylamino, dialkylamino, phenyl, nitrogen and/or oxygen or optionally substituted by a $C_{3-8}$cycloalkyl ring which optionally contains 1 to 3 heteroatoms and optionally substituted by $C_{1-4}$alkyl; or Y is a group of formula (i):

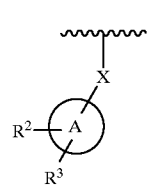

(i)

where

A is a 6 membered ring containing 0–3 nitrogen atoms, a five membered heterocyclic ring containing 1–3 heteroatoms selected from nitrogen, oxygen or sulphur or A is a fused 5,6-bicyclic ring containing 4 nitrogen atoms;

R is a group of formula (ii):

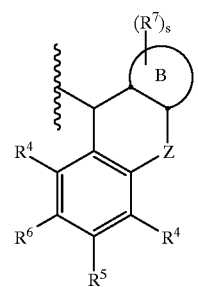

(ii)

where $R^4$ is hydrogen, halogen, $C_{1-3}$alkoxy, $C_{1-3}$alkylthio or $C_{1-3}$alkyl (optionally substituted by one or more fluorine atoms);

$R^5$ is hydrogen, hydroxy, halogen, $C_{1-3}$alkylthio, $C_{1-4}$alkyl (optionally substituted by one or more fluorine atoms), $C_{3-4}$cycloalkyl, $MeOCH_2$, $MeSCH_2$, phenyl, pyridyl, or $C_{1-3}$alkoxy; or $R^4$ and $R^5$ are —(CH$_2$)t- where t is 3 or 4 forming a fused ring;

$R^6$ is hydrogen, halogen, $C_{1-3}$alkoxy, $C_{1-3}$alkylthio, or $C_{1-3}$alkyl (optionally substituted by one or more fluorine atoms); or $R^6$ together with $R^4$ is a group —(CH$_2$)t- where t is 3 or 4 forming a fused ring;

$R^7$ is hydrogen, hydroxy, $C_{1-3}$alkoxy, amino, hydroxyC$_{1-3}$alkyl, —NHC$_{1-3}$alkyl, —NC$_{1-3}$dialkyl, —NHC$_{3-8}$cycloalkyl, —N$_{3-8}$cycloalkyl, —NHphenyl, —NHC$_{1-3}$alkylphenyl, (heterocycle)C$_{1-3}$alkyl-, (heterocycle)C$_{1-}$ $_3$alkylthio-, (heterocycle)C$_{1-3}$alkyloxy-, (heterocycle)C$_{1-3}$alkylamino-, (heterocycle)thio-, (heterocycle)oxy-, (heterocycle)amino-, C$_{1-3}$alkylthio-, cyano, thiol, C$_{1-3}$alkyl (optionally substituted by one or more fluorine atoms), —C$_{1-3}$alkylamino, —C$_{1-3}$alkylaminoalkyl, carboxamidoC$_{1-3}$alkyl, acetoxyC$_{1-3}$alkyl, or C$_{3-4}$cycloalkyl;

S is 1 or 2;

B is a 5 or 6 membered heterocyclic ring containing 1 to 3 heteroatoms selected from sulphur, oxygen or nitrogen;

Z is a bond, —O—, —S—, —SO$_2$—, —CH$_2$—, —NH—, —Nalkyl-, —CH=CH—, —CF=CH—, —CH=CF—, —CF=CF—, —CH$_2$CH$_2$—, —CH=Calkyl-, —Calkyl=CH—, —CH=C(halogen)-, —C(halogen)=CH—, —NHCO—, —CONH—, —SO$_2$NH—, —NHSO$_2$—, or a group —R$^8$CH$_2$— or —CH$_2$R$^8$— where R$^8$ is NH, Nalkyl, NCOalkyl, CO, O or S;

R$^2$ is hydrogen, NO$_2$, NH$_2$, N(C$_{1-6}$alkyl)$_2$, CO$_2$H, CH$_2$OH, halogen, CO$_2$C$_{1-6}$alkyl, C$_{1-8}$alkyl optionally interrupted by one or more oxygen, nitrogen or sulphur atoms and optionally substituted by CO$_2$H or R$^2$ is hydroxy, imidazol-1-ylCH$_2$—, phenyl optionally substituted by CH$_2$CO$_2$H or CONR$^9$R$^{10}$ where R$^9$ and R$^{10}$ are independently hydrogen, C$_{1-6}$alkyl optionally substituted by hydroxy or CO$_2$H and/or optionally interrupted by oxygen, nitrogen or sulphur;

R$^3$ is hydrogen, R$^{11}$CO$_2$H, R$^{11}$PO(OH)$_2$, R$^{12}$tetrazol-5-yl, COR$^{13}$, NR$^{14}$R$^{15}$, CH$_2$NR$^{16}$CH$_2$CO$_2$H, C$_{1-8}$alkyl optionally interrupted by one or more oxygen, sulphur or nitrogen atoms and optionally substituted by COH or R$^3$ is a group of formula (iii):

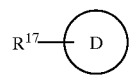

(iii)

where D is a 4,5 or 6 membered saturated ring containing a nitrogen optionally substituted by hydroxy and substituted by CO$_2$H or CONH-het where het is tetrazol-5-yl or a thiazole or a thiadiazole ring substituted by CH$_2$CO$_2$H or D is a phenyl ring or a 5 membered aromatic heterocylic ring containing 1–3 heteroatoms selected from nitrogen, oxygen or sulphur optionally substituted by one or more groups selected from CF$_3$, CO$_2$H, CH$_2$OH, C$_{1-6}$alkyl optionally interrupted by one or more oxygen atoms, (CH$_2$)pCO$_2$H, C(CO$_2$H)=NOMe, tetrazol-5-yl, CH$_2$tetrazol-5-yl, CH$_2$CON(CH$_2$CO$_2$H)$_2$, or CH$_2$COR$^{18}$; where R$^{11}$ is OCH$_2$, (CH$_2$)p, SCH$_2$, CONHCH$_2$, NHCH(R$^{19}$) or NR$^{20}$(CH$_2$)p; R$^{12}$ is a bond, (CH$_2$)p, OCH$_2$, SCH$_2$, CONH, CONHCH$_2$, CONHCH$_2$CONH, NHCH$_2$CONH, NHCH(R$^9$);

R$^{13}$ is OH, N(CH$_2$CO$_2$H)$_2$, NHS(O)$_2$R$^{21}$ or a group of formula (iv):

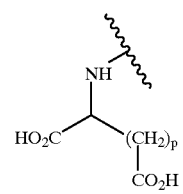

(iv)

R$^{14}$ and R$^{15}$ are independently hydrogen, CH$_2$CO$_2$H, CHPh$_2$ or C(=S)CH$_2$CH$_2$CO$_2$H;

R$^{16}$ is hydrogen, C$_{1-6}$alkyl or CO$_2$CH$_2$Ph;

R$^{17}$ is a bond, sulphur atom, CONH, CH$_2$, CH$_2$O, OCH$_2$, a group —NR$^{22}$CH(CO$_2$H)CH$_2$— group or a group CONR$^{22}$(CH$_2$)pCONR$^{23}$ or NR$^{22}$(CH$_2$)pCONR$^{23}$;

R$^{18}$ is a group of formula (iv) as defined above or a group of formula (v):

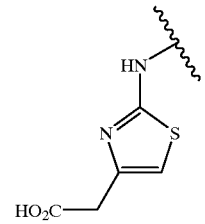

(v)

R$^{19}$ is hydrogen, C$_{1-6}$alkyl optionally substituted by hydroxy and/or optionally interrupted by oxygen, nitrogen or sulphur;

R$^{20}$ is hydrogen or C$_{1-6}$alkyl;

p is 1 or 2;

R$^{21}$ is NH$_2$ or C$_{1-6}$alkyl optionally interrupted by oxygen or nitrogen;

R$^{22}$ and R$^{23}$ are independently hydrogen, C$_{1-6}$alkyl; and

Q$^1$ and Q$^2$ each independently represent an O or S atom.

Alkyl groups, whether alone or as part of another group, can be straight chain or branched.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

Suitably Y is hydrogen, C$_{1-4}$alkyl, C$_{1-4}$alkyl optionally substituted by hydroxy, alkoxy, amino, alkylamino, dialkylamino, phenyl, nitrogen and/or oxygen or optionally substituted by a C$_{3-8}$cycloalkyl ring which optionally contains 1 to 3 heteroatoms and optionally substituted by C$_{1-4}$alkyl or Y is a group of formula (I) as defined above. Preferably Y is hydrogen, C$_{1-4}$alkyl, C$_{1-4}$alkyl optionally substituted by hydroxy, nitrogen and/or oxygen or C$_{3-8}$cycloalkyl optionally containing 1 to 3 heteroatoms and optionally substituted by C$_{1-4}$alkyl. More preferably Y is methyl, hydroxyethyl or methoxyethyl.

Suitably X is a bond or a C$_{1-3}$alkylene group optionally interrupted by oxygen. Preferably X is a bond or a CH$_2$ group.

When Y is a group of formula (i) A is a 6 membered ring containing 0–3 nitrogen atoms, a five membered heterocycle ring containing 1–3 heteroatoms selected from nitrogen, oxygen or sulphur or A is a fused 5,6-bicyclic ring containing 4 nitrogen atoms. Examples of suitable heterocyclic rings include pyridine, pyrimidine, thiazole, oxazole, thiophene, furan and pyridazine. Preferably A is furan, oxazole, pyrimidine or phenyl.

Suitably $R^4$ is hydrogen, halogen, $C_{1-3}$alkoxy, $C_{1-3}$alkylthio or $C_{1-3}$alkyl (optionally substituted by one or more fluorine atoms). $R^4$ at both positions can be the same or different. Preferably $R^4$ is hydrogen.

Suitably $R^5$ is hydrogen, hydroxy, halogen, $C_{1-3}$alkylthio, $C_{1-4}$alkyl (optionally substituted by one or more fluorine atoms), $C_{3-4}$cycloalkyl, MeOCH$_2$, MeSCH$_2$, phenyl, pyridyl, or $C_{1-3}$alkoxy; or $R^4$ and the adjacent $R^6$ group together form a group —(CH$_2$)t- where t is 3 or 4, that is $R^4$ and $R^6$ form a fused ring. Preferably $R^5$ is halogen, hydrogen, hydroxy or $C_{1-4}$alkyl, more preferably halogen, methyl or ethyl.

Suitably $R^6$ is hydrogen, halogen, $C_{1-3}$alkoxy, $C_{1-3}$alkylthio, or $C_{1-3}$alkyl (optionally substituted by one or more fluorine atoms); or $R^5$ and $R^6$ are —(CH$_2$)t- where t is 3 or 4 forming a fused ring. Preferably $R^6$ is hydrogen or methyl.

Suitably $R^7$ is hydrogen, hydroxy, $C_{1-3}$alkoxy, amino, hydroxy$C_{1-3}$alkyl, —NHC$_{1-3}$alkyl, —NC$_{1-3}$dialkyl, —NHC$_{3-8}$cycloalkyl, —N$_{3-8}$cycloalkyl, —NHphenyl, —NHC$_{1-3}$alkylphenyl, (heterocycle)C$_{1-3}$alkyl-, (heterocycle)C$_{1-3}$alkylthio-, (heterocycle)C$_{1-3}$alkyloxy-, (heterocycle)C$_{1-3}$alkylamino-, (heterocycle)thio-, (heterocycle)oxy-, (heterocycle)amino-, C$_{1-3}$alkylthio-, cyano, thiol, $C_{1-3}$alkyl (optionally substituted by one or more fluorine atoms), —C$_{1-3}$alkylamino, —C$_{1-3}$alkylaminoalkyl, carboxamido$C_{1-3}$alkyl, acetoxy$C_{1-3}$alkyl, or $C_{3-4}$cycloalkyl. The term (heterocycle) denotes a 5 or 6 membered saturated or unsaturated ring containing 1–5 heteroatoms selected from sulphur, oxygen or nitrogen. Examples of suitable heterocycles include morpholine, pyrrolidine, imidazoline, thiazoline, piperazine, pyrrole, thiophene, furan, oxazole, thiazole, imidazole, isoxazole, isthiazole, triazole, pyrazole, thiadiazole, tetrazole, pyridine, pyrimidine, pyridazine, pyrazine or triazine. Preferably $R^7$ is hydrogen, hydroxy, amino, methylamino, dimethylamino, NHcyclopropyl, NHcyclobutyl, NHbenzyl, imidazol-2-ylthio-, thiadiazol-2-ylthio-, triazol-2-ylthio-, thiol, methyl, ethyl, cyclopropyl, methylthio, methoxy, hydroxyethyl, acetoxyethyl, imidazol-4-ylethyl, or imidazol-1-ylethoxy.

More preferably $R^7$ is methyl, ethyl, hydrogen, hydroxy, hydroxyethyl, imidazol-4-ylethyl, or amino.

Suitably S is 1 or 2. Preferably S is 1 or 2.

Suitably B is a 5 or 6 membered heterocyclic ring containing 1 to 3 heteroatoms selected from sulphur, oxygen or nitrogen; Examples of suitable heterocycles include pyrrole, thiophene, furan, oxazole, thiazole, imidazole, isoxazole, isthiazole, triazole, pyrazole, thiadiazole, pyridine, pyrimidine, pyridazine, pyrazine, triazine. Preferably B is pyridine, oxazole, thiazole or imidazole Suitably Z is a bond, —O—, —S—, —SO$_2$—, —CH$_2$—, —NH—, —Nalkyl-, —CH=CH—, —CF=CH—, —CH=CF—, —CF=CF—, —CH$_2$CH$_2$—, —CH=Calkyl-, —Calkyl=CH—, —CH=C(halogen)-, —C(halogen)=CH—, —NHCO—, —CONH—, —SO$_2$NH—, —NHSO$_2$—, or a group —R$^8$CH$_2$— or —CH$_2$R$_8$— where R$^8$ is NH, Nalkyl, NCOalkyl, CO, O or S. Preferably Z is —CH=CH—, —CH$_2$CH$_2$—, or —CH$_2$O—.

Suitably $R^2$ is hydrogen, NO$_2$, NH$_2$, N(C$_{1-6}$alkyl)$_2$, CO$_2$H, CH$_2$OH, halogen, CO$_2$C$_{1-6}$alkyl, C$_{1-8}$alkyl optionally interrupted by one or more oxygen, nitrogen or sulphur atoms and optionally substituted by CO$_2$H or R$^2$ is hydroxy, imidazol-1-ylCH$_2$—, phenyl optionally substituted by CH$_2$CO$_2$H or CONR$^9$R$^{10}$ where R$^9$ and R$^{10}$ are independently hydrogen, C$_{1-6}$alkyl optionally substituted by hydroxy or CO$_2$H and/or optionally interrupted by oxygen, nitrogen or sulphur. Preferably $R^2$ is hydrogen or CO$_2$H Suitably $R^3$ is hydrogen, C$_{1-8}$alkyl optionally interrupted by one or more oxygen, sulphur or nitrogen atoms and optionally substituted by CO$_2$H, or R$^3$ is R$^{11}$PO(OH)$_2$ or R$^{11}$CO$_2$H where R$^{11}$ is OCH$_2$, (CH$_2$)p where p is 1 or 2, SCH$_2$, CONHCH$_2$; or R$^{11}$ is NHCH(R$^{19}$) where R$^{19}$ is hydrogen, C$_{1-6}$alkyl optionally substituted by hydroxy and/or optionally interrupted by oxygen, nitrogen or sulphur; or R$^{11}$ is NR$^{20}$(CH$_2$)p where p is 1 or 2 and R$^{20}$ is hydrogen or C$_{1-6}$alkyl; or R$^3$ is R$^{12}$tetrazol-5-yl where R$^{12}$ is a bond, (CH$_2$)p, OCH$_2$, SCH$_2$, CONH, CONHCH$_2$, CONHCH$_2$CONH, NHCH$_2$CONH, NHCH(R$^9$); or R$^3$ is COR$^{13}$ where R$^{13}$ is OH, N(CH$_2$CO$_2$H)$_2$, NHS(O)$_2$R$^{21}$ where R$^{21}$ is NH$_2$ or C$_{1-6}$alkyl optionally interrupted by oxygen or nitrogen or R$^{13}$ is a group of formula (iv):

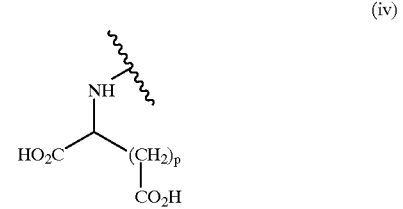

(iv)

or R$^3$ is NR$^{14}$R$^{15}$ where R$^{14}$ and R$^{15}$ are independently hydrogen, CH$_2$CO$_2$H, CHPh$_2$ or C(=S)CH$_2$CH$_2$CO$_2$H; or R$^3$ is CH$_2$NR$^{16}$CH$_2$CO$_2$H where R$^{16}$ is hydrogen, C$_{1-6}$alkyl or CO$_2$CH$_2$Ph; or R$^3$ is a group of formula (iii):

(iii)

where D is a 4, 5 or 6 membered saturated ring containing a nitrogen atom and optionally substituted by hydroxy and substituted by CO$_2$H or CONH-het where het is tetrazol-5-yl or a thiazole or a thiadiazole ring substituted by CH$_2$CO$_2$H or D is a phenyl ring or a 5 membered aromatic heterocylic ring containing 1–3 heteroatoms selected from nitrogen, oxygen or sulphur optionally substituted by one or more groups selected from CF$_3$, CO$_2$H, CH$_2$OH, C$_{1-6}$alkyl optionally interrupted by one or more oxygen atoms, (CH$_2$)pCO$_2$H, C(CO$_2$H)=NOMe, tetrazol-5-yl, CH$_2$tetrazol-5-yl, CH$_2$CON(CH$_2$CO$_2$H)$_2$, or CH$_2$COR$^{18}$ where R$^{18}$ is a group of formula (iv) as defined above or a group of formula (v):

(v)

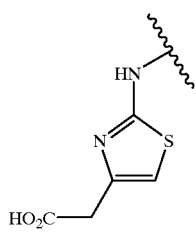

$R^{17}$ is a bond, sulphur atom, CONH, $CH_2$, $CH_2O$, $OCH_2$, a group —$NR^{22}CH(CO_2H)CH_2$— group or a group $CONR^{22}(CH_2)pCONR^{23}$ or $NR^{22}(CH_2)pCONR^{23}$ where $R^{22}$ and $R^{23}$ are independently hydrogen, $C_{1-6}$alkyl.

Preferably $R^3$ is hydrogen, a group of formula (iii) where D is a 4-membered saturated ring containing a nitrogen atom and substituted by $CO_2H$, or D is a 5-membered aromatic heterocycle containing 2 or 3 heteroatoms selected from nitrogen and sulphur and optionally substituted by $CH_2CO_2H$ or $CF_3$ and $R^{17}$ is a bond, CONH, $NHCH_2CONH$ or $CH_2$.

Suitably $Q^1$ and $Q^2$ each independently represent an O or S. Preferably $Q^1$ is S and $Q^2$ is O or S.

Particularly preferred compounds of the invention include those exemplified herein, both in free base form and as pharmaceutically acceptable salts.

In a further aspect the invention provides a process for the preparation of a compound of formula (I) which comprises:

(a) reacting a compound of formula (II):

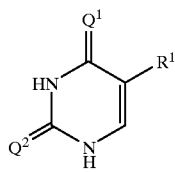

(II)

where $Q^1$ and $Q^2$ are as defined in formula (I) and $R^1$ is as defined in formula (I) or is a protected derivative thereof with a compound of formula (III):

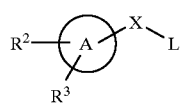

(III)

where $R^2$, $R^3$ and A are as defined in formula (I) or are protected derivatives thereof, X is as defined in formula (I) and L is a leaving group, or (b) reacting a compound of formula (IV):

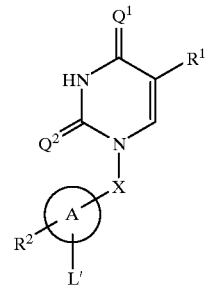

(IV)

where $Q^1$, $Q^2$, $R^1$ and X are as defined in formula (I), $R^2$ and A are as defined in formula (I) or are protected derivatives thereof and L' is a leaving group with a compound of formula (V), (VI) or (VII):

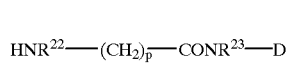

(V)

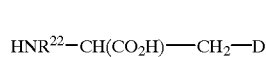

(VI)

(VII)

where $R^{22}$, $R^{23}$ and p are as defined in formula (I) and D is as defined in formula (I) or is a protected derivative thereof, or (c) when $R^3$ is a group —$R^{11}$—$CO_2H$ and $R^{11}$ is $SCH_2$ or $NR^{20}(CH_2)_p$, reacting a compound of formula (iv) as defined above with a compound H—$R^{11}$—$CO_2R^{24}$ where $R^{11}$ is $SCH_2$ or $NR^{20}(CH_2)_p$ and $R^{24}$ is hydrogen or an ester forming group;

and optionally thereafter (a), (b) or (c) in any order:
  removing any protecting groups
  converting the compound of formula (I) into a further compound of formula (I)
  forming a salt Reaction of compounds of formulae (II) and (III) can be carried out in the presence of a suitable base, for example a metal carbonate such as potassium carbonate or cesium carbonate in a suitable polar solvent such as NMP, dimethylformamide or dimethylsulphoxide at ambient or elevated temperature, for example at about 80° C. Preferably L is halogen when X is a bond, in particular chloro or fluoro. Alternatively for compounds where X is $CH_2$ the compound of formula (II) can be silylated with a suitable silylating reagent such as a trialkylsilylchloride and/or 1,1,1,3,3,3-hexamethyldisilazane in a suitable solvent such as pyridine, toluene or 1,4-dioxane at a temperature of about 80° C. to about 140° C. followed by addition of the compound of formula (III) in a suitable solvent such as acetonitrile at elevated temperature, for example at reflux. We prefer to silylate using bis(trimethylsilyl)trifluoroacetamide in refluxing 1,2-dichloroethane followed by treatment with the appropriate compound of formula (III) (where L is halogen, preferably bromide or chloride) in acetonitrile and 1,2-dichloroethane at reflux.

Compounds of formula (IV) can be reacted with compounds H—$R^{11}$—$CO_2R^{24}$ in the presence of a suitable base. When $R^{11}$ is $SCH_2$ the base is preferably NaH and when $R^{11}$ is $NR^{20}(CH_2)_p$ the base is preferably an organic amine such as N,N-diisopropylethylamine. The group $R^{24}$ is hydrogen or a suitable ester forming group such as benzyl or $C_{1-6}$alkyl. Compounds of formula (IV) can also be reacted with compounds of formulae (V), (VI) or (VII) using the procedure described above for when $R^{11}$ is $NR^{20}(CH_2)_p$.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydropyranyl. Suitable protecting groups for amino include tert-butoxycarbonyl or benzyloxy carbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

In particular compounds of formula (III) where $R^2$ and $R^3$ contains a carboxylic acid group can be protected as esters, particularly as $C_{1-6}$alkyl esters. Basic hydrolysis of such esters can be performed using metal hydroxides or quaternary ammonium hydroxides such as sodium hydroxide in a solvent such as an aqueous alcohol, 1,4-dioxane, tetrahydrofuran or dimethylformamide at a temperature between 10° C. and 100° C. When $Q^1/Q^2$ are oxygen, acidic hydrolysis may also be performed using mineral acid such as HCl or a strong organic acid such as trifluoroacetic acid in a suitable solvent such as 1,4-dioxane. We prefer basic hydrolysis using lithium hydroxide in aqueous tetrahydrofuran or aqueous methanol at ambient temperature.

Compounds of formula (I) can be converted into further compounds of formula (I) using standard procedures, for example using known alkylation, hydrolysis, esterification and amide formation chemistry, for example the use of a coupling reagent. Coupling reagents which may be used include 1,1'-carbonyldiimidazole and 1,3-dicyclohexylcarbodiimide in a suitable solvent such as dimethylformamide, dichloromethane, tetrahydrofuran or acetonitrile at about 0° C. to 30° C. We prefer to use bromo-tris(pyrrolidino)-phosphonium hexafluorophosphate with a trialkylamine such as N,N-diisopropylaminopyridine in dimethylformamide at ambient temperature. Compounds of formula (I) where $Q^1$ is oxygen can be converted to a corresponding compound of formula (I) where $Q^1$ is sulphur using standard thiation conditions for conversion of uridine and thymidine nucleosides in their corresponding thionucleoside derivatives (see "Chemistry of Nucleosides and Nucleotides" edited by Leroy B. Townsend, Plenum Press volume 1). Thiation may be achieved using reagents such as diphosphorus pentasulphide or Lawesson's reagent in a solvent such as pyridine, 1,4-dioxane, toluene, xylene, or tetrahydrofuran at a temperature of about 50° C. to about 130° C. We prefer to use Lawesson's reagent in 1,4-dioxane at about 100° C. when selectivity can be achieved.

Thiation can also be achieved by displacement of a suitable leaving group in the 2- or 4-position of the uracil by hydrogen sulphide in a suitable solvent such as pyridine and triethylamine at ambient temperature. Suitable leaving groups include alkylthio or halogen, preferably alkylthio, more preferably methylthio.

Compounds of formula (II) where $Q^1$ and $Q^2$ are oxygen can be prepared by reaction of a compound of formula (VIII):

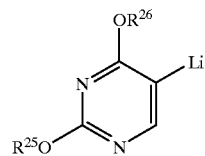

(VIII)

where $R^{25}$ and $R^{26}$ are independently $C_{1-6}$alkyl or benzyl with a compound of formula (IX):

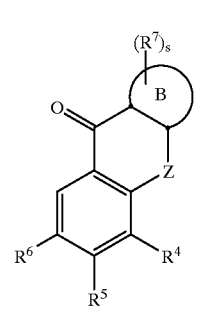

(IX)

where Z, $R^4$, $R^5$, $R^6$ and $R^7$ groups are as defined in formula (I) followed by reduction of the resulting alcohol. Compounds of formula (VIII) are prepared by treating the corresponding halide with an alkyl lithium reagent (alkyl= n-Butyl, sec-Butyl, tert-Butyl) in solvents such as tetrahydrofuran or diethyl ether at low temperature e.g. −40° C. to −78° C.

The resulting alcohol can then be reduced to compounds of type (I) by treatment with a trialkylsilane such as triethylsilane in a suitable solvent such as dichloromethane, chloroform, or 1,2-dichloroethane and an acid or Lewis acid such as trifluoroacetic acid or borontrifluoride diethyl ether complex. We preferred to perform the metal halogen exchange on 5-bromo-2,4-bis(1,1-dimethylethoxy) pyrimidine using n-butyl lithium at about −78° C in tetrahydrofuran.

When the lithio species is quenched with a compound of formula (IX) where Z is $CH_2CH_2$ the resulting alcohol can then be converted to a compound of formula (II) where Z is CH=CH by refluxing in a carboxylic acid solvent (D. Hellwinkel and T. Becker, Chem. Ber., 1989, 122, 1595). Preferred acids include acetic acid. In some cases further treatment with trifluoroacetic acid at reflux may be required for the dehydration to give the substituted uracil.

Compounds of formula (II) can also be prepared from uracil or 1-alkyluracil and the appropriately substituted alcohols of formula (XII)

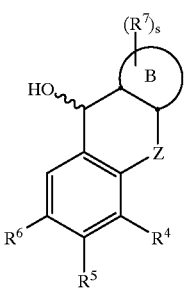

(XII)

in which Z, , $R^4$, $R^5$, $R^6$ and $R^7$ groups are as defined in formula (I) by refluxing in a carboxylic acid solvent such as acetic acid or trifluoroacetic acid (J.O.C., 1974, 39, 587) or in a siutable solvent such as acetonitrile and a Lewis acid such as boron trifluoride etherate from ambient temperature to reflux.

Compounds of formula (XII) can be prepared from compounds of formula (IX) using a reducing agent such as sodium borohydride in a suitable solvent such as an alcohol, for example ethanol or diisobutylaluminium hydride in a suitable solvent such as tetrahydrofuran or diethyl ether or benzene or toluene from 0° C. to 50° C.

Compounds of type (IX) can be prepared from compounds of type (X) by treatment with polyphosphoric acid at high temperature (100° C.–200° C.) or by treatment of the corresponding acid chloride under Friedel-Crafts type conditions using a suitable Lewis acid such as the halide salts of Boron, Tin, Iron, Zinc or Aluminium. We preferred to use anhydrous $AlCl_3$ in a suitable solvent such as dichloromethane, carbon disulphide or 1,2-dichloroethane heated under reflux

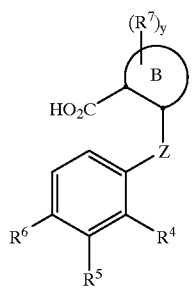

(X)

Alternatively when B is oxazole, thiazole or imidazole, (IX) can be prepared from the corresponding cycloheptanone (XI) in several steps using the methods of Galantay et al (J.Med.Chem., 1974, 17, 1316).

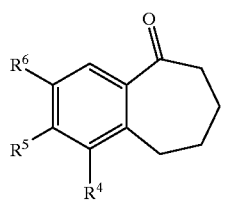

(XI)

Salts of the compounds of formula (I) may be formed by reacting the free acid, or a salt thereof, with one or more equivalents of the appropriate base (for example ammonium hydroxide optionally substituted by $C_{1-6}$-alkyl or an alkali metal or alkaline earth metal hydroxide). The reaction may be carried out in a solvent or medium in which the salt is insoluble or in a solvent in which the salt is soluble, e.g. water, alcohol or acetone, which may be removed in vacuo, or by freeze drying. The reaction may also be a metathetical process or it may preferably be carried out on an ion exchange resin. The non-toxic pharmaceutically acceptable salts are preferred, although other salts may be useful, e.g. in isolating or purifying the product.

All novel intermediates form a further aspect of the invention.

The compounds of the invention have been submitted to the assay outlined below and have been found to be P2 7-TM G-protein receptor antagonists, particularly to the $P2Y_2$ receptor. Accordingly they are useful in therapy and are, in particular, indicated for use as anti-inflammatory agents. The invention therefore provides a pharmaceutical composition comprising a compound of formula I as defined herein or a pharmaceutically acceptable salt thereof in association with a pharmaceutically acceptable adjuvant, diluent or carrier.

The invention provides in a further aspect a method of treating an inflammatory condition which comprises administering to a patient in need of therapy, a therapeutically effective amount of a compound of the invention. If desired the compounds of the invention can be administered with other anti-inflammatory agents for example NSAIDS, $cPLA_2$ inhibitors COX-2 inhibitors or iNOS inhibitors.

According to the invention there is further provided use of the compounds of the invention in the manufacture of a medicament for use in the treatment of an inflammatory condition.

The compounds may be administered orally, topically e.g. to the lung and/or the airways, dermally, in the form of solutions, suspensions, HFA areosols and dry powder formulations, e.g. Turbuhaler® formulations or by parenteral administration in the form of sterile parenteral solutions or suspensions.

The invention further provides a pharmaceutical composition comprising a compound according to the present invention in association with a pharmaceutically acceptable excipient and/or adjuvant. Particularly preferred are compositions not containing material capable of causing an adverse, e.g. an allergic, reaction. For example a chelating or sequestering agent, an antioxidant, a tonicity adjusting agent, a pH modifying agent and/or a buffering agent are suitable additives.

The compounds of the invention may also be administered by means of a dry powder inhaler. The inhaler may be a single or a multi dose inhaler, and may be a breath actuated dry powder inhaler.

A pharmaceutical composition according to the present invention could optionally be prepared in freeze dried form using any lyophilisation techniques commonly used within the pharmaceutical area. Upon use but before administration, such pharmaceutical compositions are generally reconstituted in a pharmaceutically acceptable excipient. Preferably a solution of the pharmaceutical composition according to the invention obtained after reconstitution is an isotonic solution. Such a pharmaceutical composition according to the present invention when reconstituted is preferably administered by injection, for example intravenously, subcutaneously or intramuscularly.

The invention is illustrated by the following examples. In the examples the NMR spectra were measured on a Varian Unity Inova 300 or 400 MHz spectrometer and the MS spectra measured as follows: EI spectra were obtained on a VG 70-250S or Finnigan Mat Incos-XL spectrometer, ESI and APCI spectra were obtained on Finnigan Mat SSQ7000 or a Micromass Platform spectrometer. Where necessary, the reactions were performed under an inert atmosphere of either nitrogen or argon. Where necessary, preparative HPLC separations were generally performed using a Novapak®, Bondapak®, or Hypersil® column packed with BDSC-18 reverse phase silica gel. Chromatography was generally performed using Matrex Silica 60® (35–70 micron) or Prolabo Silica gel 60® (35–75 micron) suitable for flash silica gel chromatography. Reverse phase chromatography was generally performed using C18 sep-pak® (55–105 micron).

EXAMPLE 1

(±)-5-[[5-(2-Ethyl-7-methyl-4H-benzo[5,6]cyclohepta[1,2-d]oxazol-4-yl)-3,4-dihydro-2,4-dioxo-1(2H)-pyrimidinyl]methyl]-2-furancarboxylic acid i) 5-(3-Methylphenyl)penta-2,4-dienoic acid A mixture of potassium tert-butoxide (68 g) and tert-butanol (130 ml) was treated dropwise with a mixture of 3-methylbenzaldehyde (33.8 g) and methyl crotonate (45 ml). The temperature of the reaction mixture rose to 65° C. during the addition and this was maintained for a further 3 hours. The reaction mixture was cooled to room temperature, poured into ice/water and washed with diethyl ether. The aqueous phase was acidified with concentrated HCl and extracted with diethyl ether. The organic phase was washed with water, dried ($MgSO_4$) and evaporated under reduced pressure. Purification was by trituration with isohexane and filtration.

Yield 36.8 g. 1H NMR: δ ($CDCl_3$) 8.06 (d of d, 1H), 7.4–7.3 (m, 3H), 7.15 (d, 1H), 6.85 (m, 2H), 5.74 (d, 1H), 2.38 (s, 3H).

ii) 5-(3-Methylphenyl)pentanoic acid

A solution of the product from step (i) (36.8 g) in ethanol (300 ml) was hydrogenated over 10% palladium on carbon (1 g) at 1 atmosphere pressure for 3 days. The catalyst was removed by filtration and the mother liquor was evaporated under reduced pressure.

Yield 34.2 g. 1HNMR: δ (DMSO) 12.05 (s, 1H), 7.15 (t, 1H), 6.98 (d, 3H), 2.50 (m, 2H), 2.25 (m, 5H), 1.52 (m, 4H).

iii) 6,7,8,9-Tetrahydro-2-methyl-5H-benzocyclohepten-5-one

A mixture of the product from step (ii) (14 g) and polyphosphoric acid (150 ml) was heated at 100° C. for 16 hours. The reaction mixture was poured onto ice/water and extracted with diethyl ether. The organic phase was washed with dilute NaOH and saturated brine. The organic phase was dried ($MgSO_4$) and the solvent evaporated under reduced pressure. Purification was by chromatography eluting with 10% ethyl acetate in toluene.

Yield 4.54 g. MS: APCI (+ve): 175 (M+1, 100%).

iv) 8,9-Dihydro-2-methyl-5H-benzocycloheptene-5,6(7H)-dione, 6-oxime.

A solution of the product from step (iii) (4.5 g) in diethyl ether (200 ml) and 1M HCl in diethyl ether (32 ml) was treated dropwise with isoamyl nitrite (4.5 ml) at −15° C. The reaction mixture was stirred at 0° C. for 72 hours and the solvent was evaporated under reduced pressure. Purification was by recrystallisation from isohexane/ethyl acetate.

Yield 2.2 g. MS: APCI (+ve): 204 (M+1, 100%).

v) 2-Ethyl-9,10-dihydro-7-methyl-4H-benzo[5,6]cyclohepta[1,2-d]oxazol-4-one

Propionyl chloride (4.7 ml) was added dropwise to a mixture of propionic acid (25 ml), propionic anhydride (2.5 ml) and the product from step (iv) (2.2 g) at 85° C. The reaction mixture was heated at this temperature for a further 1 hour then poured into ice/water/NaOH (sufficient to maintain pH>7) and extracted with diethyl ether. The organic phase was dried ($MgSO_4$) and the solvent was evaporated under reduced pressure. Purification was by chromatography eluting with 25% ethyl acetate in toluene.

Yield 1.26 g. MS: APCI (+ve): 242 (M+1, 100%).

vi) 5-Bromo-2,4-bis(1,1-dimethylethoxy)pyrimidine

To a solution of potassium tert-butoxide (67.5 g) in tetrahydrofuran (500 ml) was added 5-bromo-2,4-dichloropyrimidine (55 g) (*J. Am. Chem. Soc.*, 1934, 56, 134) in tetrahydrofuran (100 ml) dropwise. After 1.5 hours water (100 ml) was added carefully and the mixture extracted with ethyl acetate. The combined organic solution was washed with water, dried ($MgSO_4$) and evaporated under reduced pressure. Purification was by chromatography eluting with isohexane containing 1% triethylamine.

Yield 52.4 g. MS: GC-MS: 304/302 ($M^+$)

vii) (±)-5-(2-Ethyl-7-methyl-4H-benzo[5,6]cyclohepta[1,2-d]oxazol-4-yl)-2,4(1H,3H)-pyrimidinedione To a solution of the product of step (vi) (1.74 g) in dry tetrahydrofuran (20 ml) at −78° C. was added n-butyllithium (2.3 ml of a 2.5M solution in hexanes) dropwise. After 0.5 hours a solution of the product from step (v) (1.26 g) in tetrahydrofuran (10 ml) was added. The reaction mixture was allowed to warm to room temperature and saturated brine was added. The mixture was extracted with ethyl acetate, the organic phase was dried ($MgSO_4$) and the solvent was evaporated under reduced pressure. The residue was dissolved in acetic acid (20 ml) and the solution was heated at reflux for 64 hours. The solvent was evaporated under reduced pressure and the residue was then dissolved in trifluoroacetic acid (20 ml) and the solution heated at reflux for 64 hours. The solvent was evaporated under reduced pressure. Purification was by trituration with diethyl ether and filtration.

Yield 1.42 g. MS: APCI (+ve): 336 (M+1, 100%).

viii) (±)-5-[[5-(2-Ethyl-7-methyl-4H-benzo[5,6]cyclohepta[1,2-d]oxazol-4-yl)-3,4-dihydro-2,4-dioxo-1(2H)-pyrimidinyl]methyl]-2-furancarboxylic acid, ethyl ester To a slurry of the product of step (vii) (1.42 g) in dry 1,2-dichloroethane (15 ml) was added bis(trimethylsilyl)trifluoroacetamide (3.4 ml). The mixture was heated at reflux for 2 hours until the mixture became a homogeneous solution. The solution was allowed to cool to room temperature and a solution of 5-[bromomethyl]-2-furancarboxylic acid ethyl ester (*J. Chem. Soc. Perkin Trans.* 1, 1981, 1125, *Bull. Chem. Soc. Jpn.*, 1987, 60, 1807) (1.1 g) in dry acetonitrile (15 ml) was added. The solution was then heated at reflux for 14 hours. The reaction mixture was allowed to cool and methanol (15 ml) was added. The solvents were evaporated under reduced pressure and the residue was triturated with diethyl ether. The resultant solid was collected by filtration and partitioned between saturated aqueous sodium bicarbonate and ethyl acetate. The organic phase was dried ($MgSO_4$) and the solvent was evaporated under reduced pressure. Purification was by chromatography eluting with ethyl acetate.

Yield 0.26 g. MS: APCI (+ve): 488 (M+1, 100%).

15 ix) (±)-5-[[5-(2-Ethyl-7-methyl-4H-benzo[5,6]cyclohepta[1,2-d]oxazol-4-yl)-3,4-dihydro-2,4-dioxo-1(2H)-pyrimidinyl]methyl]-2-furancarboxylic acid A mixture of the product of step (viii) (0.26 g) and lithium hydroxide monohydrate (0.063 g) in methanol (4 ml) and water (4 ml) was stirred at room temperature for 1.5 hours. The solution was neutralised by the addition of 2M hydrochloric acid and the solvents were evaporated under reduced pressure. Purification was by preparative HPLC followed by lyophilisation.

Yield 0.035 g. MS: APCI (−ve): 458 (M−1, 100%). 1H NMR: δ (DMSO) 7.37 (d, 1H), 7.18 (d, 2H), 7.03 (d, 1H), 6.84 (s, 1H), 6.76 (d, 2H), 6.42 (d, 1H), 5.19 (s, 1H), 4.90 (d, 1H), 4.77 (d, 1H), 2.74 (q, 2H), 2.26 (s, 3H), 1.22 (t, 3H). MP: 168–169° C.

EXAMPLE 2

(±)-2-[[5-(2-Ethyl-7-methyl-4H-benzo[5,6]cyclohepta[1,2-d]oxazol-4-yl)-3,4-dihydro-2-oxo-4-thioxo-1(2H)-pyrimidinyl]methyl]-4-oxazolecarboxylic acid i) (±)-2-[[5-(2-Ethyl-7-methyl-4H-benzo[5,6]cyclohepta[1,2-d]oxazol-4-yl)-3,4-dihydro-2,4-dioxo-1(2H)-pyrimidinyl]methyl]-4-oxazolecarboxylic acid, ethyl ester The subtitle compound was prepared from the product from example 1 step (vii) (6.5 g) and 2-[bromomethyl]-4-oxazolecarboxylic acid ethyl ester (*Coll. Czech Chem. Comm.*, 1967, 32, 2155) (1.69 g) by the method of example 1 step (viii). Purification was by chromatography eluting with 60–66% ethyl acetate in toluene.

Yield 1.26 g. MS: APCI (+ve): 489 (M+1, 100%).

ii) (±)-2-[[5-(2-Ethyl-7-methyl-4H-benzo[5,6]cyclohepta[1,2-d]oxazol-4-yl)-3,4-dihydro-2-oxo-4-thioxo-1(2H)-pyrimidinyl]methyl]-4-oxazolecarboxylic acid, ethyl ester A mixture of the product of step (i) (1.26 g) and Lawesson's reagent (1.56 g) in 1,4-dioxane (30 ml) was heated at reflux for 16 hours. The solvent was evaporated under reduced pressure. The residue was partitioned between ethyl acetate and saturated brine. The organic phase was collected, dried (MgSO$_4$) and solvent evaporated under reduced pressure. Purification was by chromatography eluting with 50% ethyl acetate in toluene.

Yield 0.55 g. MS: APCI (+ve): 505 (M+1, 100%).

iii) (±)-2-[[5-(2-Ethyl-7-methyl-4H-benzo[5,6]cyclohepta[1,2-d]oxazol-4-yl)-3,4-dihydro-2-oxo-4-thioxo-1(2H)-pyrimidinyl]methyl]-4-oxazolecarboxylic acid.

A mixture of the product of step (ii) (0.55 g) and lithium hydroxide monohydrate (0.46 g) in methanol (10 ml) and water (10 ml) was stirred at room temperature for 3 hours. The solution was concentrated under reduced pressure to 10 ml and partitioned between 2M hydrochloric acid and ethyl acetate. The organic phase was dried (MgSO$_4$) and the solvent evaporated under reduced pressure. Purification was by reverse phase chromatography eluting with 50% methanol in 0.1% aqueous ammonium acetate followed by lyophilisation.

Yield 0.060 g. MS: APCI (+ve): 477 (M+1, 100%). 1H NMR: δ (DMSO) 8.61 (s, 1H), 7.63 (d, 1H), 7.28 (s, 1H), 7.20 (m, 2H), 6.86 (d, 1H), 6.76 (d, 1H), 5.92 (s, 1H), 5.11 (d, 1H), 5.01 (d, 1H), 2.76 (q, 2H), 2.27 (s, 3H), 1.22 (t, 3H).

EXAMPLE 3

(±)-2-[2-[[4-[5-(7-Ethyl-2-methyl-4H-benzo[5,6]cyclohepta[1,2-d]oxazol-4-yl)-3,4-dihydro-2,4-dioxo-1(2H)-pyrimidinyl]pyrimidin-2-yl]amino]acetylamino]-4-thiazoleacetic acid i) 3-Ethylbenzaldehyde A solution of 3-bromo-ethylbenzene (25 g) in dry tetrahydrofuran (350 ml) at −70° C. was treated dropwise with n-butyllithium (59 ml of a 2.5M solution in hexanes) and stirred for 1 hour. N,N-Dimethylformamide (30 ml) was added and the solution was stirred at −70° C. for 1 hour and allowed to warm to room temperature. The reaction mixture was partitioned between saturated ammonium chloride solution and ethyl acetate. The organic phase was washed with 1N hydrochloric acid, dried (MgSO$_4$) and evaporated.

Yield 18.55 g. 1H NMR: δ (DMSO) 10.00 (s, 1H), 7.71 (m, 2H), 7.47 (m, 2H), 2.74 (q, 2H), 1.28 (t, 3H)

ii) 5-(3-Ethylphenyl)penta-2,4-dienoic acid

The subtitle compound was prepared from the product of step (i) (18.55 g) according to the method of example 5 steps (i) and (ii).

Yield 25 g. MS: APCI (−ve): 201 (M−1, 100%)

iii) 5-(3-Ethylphenyl)pentanoic acid

The subtitle compound was prepared from the product of step (ii) (25 g) according to the method of example 1 step (ii).

Yield 21.70 g. MS: APCI (−ve): 205 (M−1, 100%)

iv) 2-Ethyl-6,7,8,9-tetrahydro-5H-benzocyclohepten-5-one

The subtitle compound was prepared from the product of step (iii) (19.81 g) according to the method of example 1 step (iii).

Yield 12.12 g. 1H NMR: δ (CDCl$_3$) 7.68 (d, 1H), 7.13 (dd, 1H), 7.02 (d, 1H), 2.92 (t, 2H), 2.68 (m, 4H), 1.84 (m, 4H), 1.24 (t, 3H)

v) 2-Ethyl-8,9-dihydro-5H-benzocycloheptene-5,6(7H)-dione, 6-oxime

The subtitle compound was prepared from the product of step (iv) (11.5 g) according to the method of example 1 step (iv).

Yield 9.8 g. 1HNMR: δ (CDCl$_3$) 8.80 (br s, 1H), 7.80 (d, 1H), 7.20 (dd, 1H), 7.04 (d, 1H), 2.86 (t, 2H), 2.70 (m, 5H), 2.04 (m, 2H), 1.27 (t, 3H)

vi) 7-Ethyl-9,10-dihydro-2-methyl-4H-benzo[5,6]cyclohepta[1,2-d]oxazol-4-one

The subtitle compound was prepared from the product of step (v) (9.20 g) according to the method of example 1 step (v) using acetic anhydride (4.9 ml), acetyl chloride (7.2 ml) and acetic acid (47 ml) (instead of propionic anhydride, propionyl chloride, and propionic acid).

Yield 3.49 g. 1HNMR: δ (CDCl$_3$) 7.93 (d, 1H), 7.21 (dd, 1H), 7.07 (d, 1H), 3.18 (m, 2H), 3.11 (m, 2H), 2.49 (s, 3H), 2.70 (q, 2H), 1.26 (t, 3H)

vii) (±)-5-(7-Ethyl-2-methyl-4H-benzo[5,6]cyclohepta[1,2-d]oxazol-4-yl)-2,4(1H,3H)-pyrimidinedione The subtitle compound was prepared from the product of step (vi) (3.38 g) according to the method of example 1 step (vii).

Yield 4.52 g. MS: APCI (−ve): 334 (M−1, 100%)

viii) (±)-1-(2-Chloropyrimidin-4-yl)-5-(7-ethyl-2-methyl-4H-benzo[5,6]cyclohepta[1,2-d]oxazol-4-yl)-2,4(1H,3H)-pyrimidinedione A solution of the product from step (vii) (4.50 g), cesium carbonate (4.37 g) and 2,4-dichloropyrimidine (3.00 g) in dry N,N-dimethylformamide (30 ml) was stirred for 25 hours. The reaction mixture was partitioned between ethyl acetate and water and the organic layer dried ($MgSO_4$). Evaporation of the solvent gave an oil which was purified by column chromatography eluting with 50–100% ethyl acetate in 40–60 petroleum ether.

Yield 0.65 g. MS: APCI (−ve): 446 (M−1, 100%)

ix) 2-[(2-Aminoacetyl)amino]-4-thiazoleacetic acid ethyl ester

A mixture of N-(tert-butoxycarbonyl)glycine (3.1 g), 2-amino-4-thiazoleacetic acid ethyl ester (3 g) and bromo-tris(pyrrolidino)-phosphonium hexafluorophosphate (7.54 g) in N,N-dimethylformamide (20 ml) was treated with N,N-diisopropylethylamine (6 ml). After 25 minutes 4-(dimethylamino)pyridine (1.96 g) was added. After 24 hours the mixture was partitioned between ethyl acetate and brine. The organic phase was washed with saturated aqueous sodium bicarbonate, brine, 1N HCl and brine, dried ($MgSO_4$) and evaporated. The residue was purified by chromatography eluting with 50% ethyl acetate in isohexane. The product (0.77 g) was dissolved in dichloromethane (25 ml) and trifluoroacetic acid (10 ml). After 2 hours the mixture was evaporated. The residue was partitioned between ethyl acetate and sodium bicarbonate solution. The aqueous phase was repeatedly extracted with ethyl acetate. The combined extracts were dried ($MgSO_4$) and evaporated.

Yield 0.41 g. MS: APCI (+ve): 244 (M+1)

x) (±)-2-[2-[[4-[5-(7-Ethyl-2-methyl-4H-benzo[5,6]cyclohept[1,2-d]oxazol-4-yl)-3,4-dihydro-2,4-dioxo-1(2H)-pyrimidinyl]pyrimidin-2-yl]amino]acetylamino]-4-thiazoleacetic acid, ethyl ester A mixture of the products from steps (viii) (0.65 g) and (ix) (1.025 g) and N,N-diisopropylethylamine (1.26 ml) in N-methylpyrrolidin-2-one (10 ml) was stirred at 90° C. for 24 hours. A further 0.342 g of product from step (ix) and N,N-diisopropylethylamine (0.5 ml) was added and heating continued for a further 24 hours. The solution was partitioned between 1N hydrochloric acid and ethyl acetate. The organic layer was washed with water, dried ($MgSO_4$) and evaporated to give a brown oil which was purified by chromatography eluting with ethyl acetate.

Yield 0.61 g. 1H NMR: δ (DMSO) 12.04 (br s, 1H), 11.34 (s, 1H), 8.30 (d, 1H), 7.83 (s, 1H), 7.42 (d, 1H), 7.30 (s, 1H), 7.19 (m, 3H), 6.85 (m, 3H), 5.34 (s, 1H), 4.24 (d, 1 H), 4.06 (q, 2H), 3.68 (s, 2H), 2,58 (q, 2H), 2,35 (s, 3H), 1.16 (m, 6H)

xi) (±)-2-[2-[[4-[5-(7-Ethyl-2-methyl-4H-benzo[5,6]cyclohepta[1,2-d]oxazol-4-yl)-3,4-dihydro-2,4-dioxo-1(2H)-pyrimidinyl]pyrimidin-2-yl]amino]acetylamino]-4-thiazoleacetic acid The title compound was prepared from the product of step (x) (0.6 g) according to the method of example 1 step (ix). Purification was by reverse phase chromatography eluting with 50% methanol in 0.1% aqueous ammonium acetate.

Yield 0.04 g. MS: APCI (−ve): 625 (M−1, 100%) 1H NMR: δ (DMSO) 12.02 (br s, 1H), 11.34 (s, 1H), 8.31 (d, 1H), 7.83 (s, 1H), 7.41 (d, 1H), 7.30 (s, 1H), 7.18 (m, 3H), 6.85 (m, 3H), 5.34 (s, 1H), 4.24 (d, 1H), 3.60 (s, 2H), 2.57 (q, 2H), 2,35 (s, 3H), 1.15 (t, 3H) MP: 205–210° C.

EXAMPLE 4

(±)-5-[[3,4-Dihydro-5-(2-methyl-4H-benzo[5,6]cyclohepta[1,2-d]oxazol-4-yl)-2-oxo-4-thioxo-1(2H)-pyrimidinyl]methyl]-2-furancarboxylic acid i) (±)-5-(2-Methyl-4H-benzo[5,6]cyclohepta[1,2-d]oxazol-4-yl)-2,4(1H,3H)-pyrimidinedione The subtitle compound was prepared from 9,10-dihydro-2-methyl-4H-benzo[5,6]cyclohepta[1,2-d]oxazol-4-one (2.98 g) (J. Med. Chem., 1974, 17, 1316) by the method of example 1 step (vii). Yield 4.0 g. Used directly in the next step.

ii) (±)-5-[[3,4-Dihydro-5-(2-methyl-4H-benzo[5,6]cyclohepta[1,2-d]oxazol-4-yl)-2,4-dioxo-1(2H)-pyrimidinyl]methyl]-2-furancarboxylic acid, ethyl ester The subtitle compound was prepared from the product of step (i) (2.0 g) by the method of example 1 step (viii).

Yield 0.66 g. 1H NMR: δ ($CDCl_3$) 8.21 (s, 1H), 7.57 (d, 1H), 7.40 (t, 1H), 7.33 (d, 1H), 7.29 (d, 1H), 7.10 (d, 1H), 6.83 (d, 1H), 6.72 (d, 1H), 6.70 (s, 1H), 6.41 (d, 1H), 5.46 (s, 1H), 4.77 (q, 2H), 4.20 (q, 2H), 2.48 (s, 3H), 1.43 (t, 3H).

iii) (±)-5-[[3,4-Dihydro-5-(2-methyl-4H-benzo[5,6]cyclohepta[1,2-d]oxazol-4-yl)-2-oxo-4-thioxo-1(2H)-pyrimidinyl]methyl]-2-furancarboxylic acid, ethyl ester The subtitle compound was prepared from the product of step (ii) (0.66 g) by the method of example 2 step (ii).

Yield 0.13 g. 1H NMR: δ (DMSO) 7.70 (d, 1H), 7.38 (m, 2H), 7.30 (m, 2H), 7.18 (s, 1H), 6.82 (d, 1H), 6.78 (d, 1H), 6.63 (d, 1H), 5.92 (s, 1H), 4.97 (q, 2H), 4.32 (q, 2H), 2.41 (s, 3H), 1.31 (t, 3H).

iv) (±)-5-[[3,4-Dihydro-5-(2-methyl-4H-benzo[5,6]cyclohepta[1,2-d]oxazol-4-yl)-2-oxo-4-thioxo-1(2H)-pyrimidinyl]methyl]-2-furancarboxylic acid A mixture of the product from step (iii) (0.13 g) and lithium hydroxide monohydrate (0.042 g) in methanol (20 ml) and water (10 ml) was stirred at room temperature for 72 hours and heated at reflux for 1 hour. The solution was concentrated under reduced pressure and the residue partitioned between 2M hydrochloric acid and ethyl acetate. The organic phase was dried ($MgSO_4$) and the solvent was evaporated under reduced pressure. The residue was triturated with ethyl acetate and the resultant solid collected by filtration.

Yield 0.08 g. MS: APCI (+ve) 448 (M+1, 100%) 1H NMR: δ (DMSO) 13.23 (br s, 1H), 12.82 (s, 1H), 7.71 (d, 1H), 7.36 (m, 2H), 7.29–7.18 (m, 3H), 6.86 (d, 1H), 6.76 (d, 1H), 6.60 (d, 1H), 5.92 (s, 1H), 4.95 (q, 2H), 2.41 (s, 3H). MP: >230° C.

EXAMPLE 5

(±)-N-[4-[3,4-Dihydro-5-(7-hydroxy-2-methyl-4H-benzo[5,6]cyclohepta[1,2-d]oxazol-4-yl)-2,4-dioxo-1(2H)-pyrimidinyl]pyrimidin-2-yl]-3-azetidinecarboxylic acid i) 5-(3-Methoxyphenyl)penta-2,4-dienoic acid, methyl ester A mixture of potassium tert-butoxide (52 g) and tert-butanol (170 ml) was treated dropwise with a mixture of 3-methoxybenzaldehyde (30 g) and methyl crotonate (35 ml). The temperature of the reaction mixture rose to 80° C. during the addition and was then maintained for a further 3 hours at 65° C. The reaction mixture was cooled to room temperature, poured into ice/water and washed with diethyl ether. The aqueous phase was acidified with concentrated HCl and extracted with ethyl acetate. The organic phase was washed with brine, dried ($MgSO_4$) and evaporated under reduced pressure to yield an orange oil. Yield 53.2 g. Used directly in the next step.

ii) 5-(3-Methoxyphenyl)penta-2,4-dienoic acid

A mixture of the product from step (i) (53.2 g) and lithium hydroxide monohydrate (52 g) in methanol (250 ml) and water (100 ml) was stirred at room temperature for 24 hours and partitioned between ethyl acetate and 2M HCl. The organic phase was washed with brine, dried (MgSO$_4$), and evaporated under reduced pressure to afford an orange oil.

Yield 55.0 g. MS: APCI (−ve): 203 (M−1, 100%).

iii) 5-(3-Methoxyphenyl)pentanoic acid

The subtitle compound was prepared from the product of step (ii) (55 g) according to the method of example 1 step (ii).

Yield 50.0 g. MS: APCI (−ve): 207 (M−1, 100%).

iv) 6,7,8,9-Tetrahydro-2-methoxy-5H-benzocyclohepten-5-one

The subtitle compound was prepared from the product of step (iii) (50.0 g) according to the method of example 1 step (iii).

Yield 28 g. MS: APCI (+ve): 191 (M+1, 100%).

v) 8,9-Dihydro-2-methoxy-5H-benzocycloheptene-5,6 (7H)-dione, 6-oxime

The subtitle compound was prepared from the product of step (iv) (28.0 g) according to the method of example 1 step (iv).

Yield 23.9 g. MS: APCI (+ve): 220 (M+1, 100%).

vi) 9,10-Dihydro-7-methoxy-2-methyl-4H-benzo[5,6]cyclohepta[1,2-d]oxazol-4-one

The subtitle compound was prepared from the product of step (v) (23.9 g) according to the method of example 3 step (vi).

Yield 3.8 g. MS: APCI (+ve): 244 (M+1)

vii) (±)-5-(7-Methoxy-2-methyl-4H-benzo[5,6]cyclohepta[1,2-d]oxazol-4-yl)-2,4(1H,3H)-pyrimidinedione The subtitle compound was prepared from the product of step (vi) (3.0 g) according to the method of example 1 step (vii). Yield 3.8 g. Used directly in the next step.

viii) (±)-5-[7-[(1,1-Dimethylethyl)dimethylsiloxy]-2-methyl-4H-benzo[5,6]cyclohepta[1,2-d]oxazol-4-yl]-2,4(1H,3H)-pyrimidinedione To a suspension of the product from step (vii) (1.5 g) in dichloromethane (20 ml) was added a solution of boron tribromide (1M in dichloromethane) (6 ml). The mixture was stirred at room temperature for 2 hours. A further 10 ml of boron tribromide solution was added and the mixture was stirred for 2 hours before quenching with water. The pH was adjusted to 7 with sodium bicarbonate solution and the aqueous solution extracted with ethyl acetate. The organic phase was dried (MgSO$_4$) and evaporated under reduced pressure to give a brown solid. The solid was dissolved in N,N-dimethylformamide (20 ml) and treated with imidazole (0.68 g) followed by tert-butyldimethylsilyl chloride (0.68 g). The mixture was stirred overnight then partitioned between water and ethyl acetate. The organic phase was dried (MgSO$_4$) and evaporated under reduced pressure. Purification was by precipitation with methanol/dichloromethane/isohexane.

Yield 0.36 g. MS: APCI (+ve): 438 (M+1, 100%).

ix) (±)-1-(2-Chloropyrimidin-4-yl)-5-[7-[(1,1-dimethylethyl)dimethylsiloxy]-2-methyl-4H-benzo[5,6]cyclohepta[1,2-d]oxazol-4-yl]-2,4(1H,3H)-pyrimidinedione A mixture of the product from step (viii) (0.35 g), 2,4-dichloropyrimidine (0.18 g) and cesium carbonate (0.26 g) in N,N-dimethylformamide (10 ml) was stirred at room temperature for 4 hours. The mixture was partitioned between water and ethyl acetate, the organic phase washed with water, dried (MgSO$_4$) and evaporated under reduced pressure. Purification was by chromatography eluting with 50–80% ethyl acetate in isohexane.

Yield 0.367 g. MS: APCI (+ve): 550 (M+1, 100%).

x) (±)-N-[4-[3,4-Dihydro-5-(7-hydroxy-2-methyl-4H-benzo[5,6]cyclohepta[1,2-d]oxazol-4-yl)-2,4-dioxo-1(2H)-pyrimidinyl]pyrimidin-2-yl]-3-azetidinecarboxylic acid The product from step (ix) was treated with 3-azetidinecarboxylic acid (0.096 g) and N,N-diisopropylethylamine (0.445 ml) in N,N-dimethylformamide (10 ml) at 85° C. for 4 hours. The mixture was partitioned between 1N HCl and ethyl acetate. The aqueous layer was adjusted to pH 6 and extracted with ethyl acetate. The organic phase was dried (MgSO$_4$) and evaporated under reduced pressure to give a solid. Purification was by reverse phase chromatography eluting with 50% methanol in 0.1% aqueous ammonium acetate solution.

Yield 0.059 g. MS: APCI (+ve): 501 (M+1) 1H NMR: δ (DMSO) 12.77 (s, 1H), 11.61 (s, 1H), 9.51 (s, 1H), 8.36 (d, 1H), 7.87 (s, 1H), 7.33 (d, 1H), 7.27 (d, 1H), 6.85–6.77 (m, 4H), 5.26 (s, 1H), 4.24 (t, 2H), 4.11–4.07 (m, 2H), 3.63–3.57 (m, 1H), 2.41 (s, 3H).

MP:285° C.

EXAMPLE 6

(±)-2-[[5-(2-Ethyl-7-methyl-4H-benzo[5,6]cyclohepta[1,2-d]oxazol-4-yl)-3,4-dihydro-2-oxo-4-thioxo-1(2H)-pyrimidinyl]methyl]-N-[5-(trifluoromethyl)-1H-1,2,4-triazol-3-yl]-4-oxazolecarboxamide A solution of the product of example 2 step (iii) (0.34 g), 4-(dimethylamino)pyridine (0.34 g), 3-amino-5-trifluoromethyl-1,2,4-triazole (J. Gen. Chem. USSR (Engl. Transl.) 1983, vol53, part 7, p1514) (0.42 g) and N,N-diisopropylethylamine (1.46 ml) in N,N-dimethylformamide (6 ml) was treated with bromo-tris (pyrrolidino)phosphonium hexafluorophosphate (1.3 g). After 2 hours the solution was quenched with aqueous tartaric acid. The solution was extracted with ethyl acetate. The combined extracts were washed with brine, dried (MgSO$_4$) and evaporated under reduced pressure. Purification was by chromatography eluting with 30% ethyl acetate in toluene. The product was triturated with ethyl acetate/isohexane and the solid collected.

Yield 0.12 g. MS: APCI (+ve): 611 (M+1, 100%) 1H NMR: δ (DMSO) 14.48 (br s, 1H), 12.87 (br s, 1H), 12.18 (br s, 1H), 7.64 (d, 1H), 7.30 (br s, 1H), 7.22 (m, 2H), 6.87 (d, 1H), 6.77 (d, 1H), 6.21 (s, 1H), 5.21 (d, 1H), 5.10 (d, 1H), 2.74 (q, 2H), 1.22 (t, 3H). MP: 188–190° C.

EXAMPLE 7

(±)-3-[[5-(7-Ethyl-2-methyl-4H-benzo[5,6]cyclohepta[1,2-d]oxazol-4-yl)-3,4-dihydro-2-oxo-4-thioxo-1(2H)-pyrimidinyl]methyl]-5-[imidazol-1-ylmethyl]benzoic acid i) 3,5-(Dichloromethyl)benzoic acid, ethyl ester Ethyl 3,5-dimethylbenzoate (15 g) was heated at reflux with N-chlorosuccinimide (25 g) in dry benzene (140 ml) in the presence a catalytic amount (~5 mg) of benzoyl peroxide whilst being irradiated with a 500 watt halogen lamp. After 6 hours the cooled reaction mixture was partitioned with saturated brine. The organic layer was collected, dried (MgSO$_4$) and the solvent evaporated under reduced pressure. The crude residue was purified by chromatography eluting with 10% ethyl acetate in isohexane to give the subtitle product as a colourless solid.

Yield: 3.7 g. 1H NMR: δ (CDCl$_3$) 8.05 (m, 2H), 7.62 (s, 1H), 4.63 (s, 4H), 4.20 (q, 2H), 1.40 (t, 3H).

ii) 3-Chloromethyl-5-(imidazol-1-ylmethyl)benzoic acid, ethyl ester hydrochloride The product of step (i) (3.7 g) was dissolved in dry DMF (16 ml) at 0° C. and treated with a preformed mixture of imidazole (1 g) and 60% sodium hydride (0.59 g) in DMF (16 ml) by syringe over 10 minutes. The reaction mixture was stirred for 20 minutes and carefully quenched with brine (20 ml). The product was extracted into diethyl ether. The organic phase was dried (MgSO$_4$) and treated with a 1.0M HCl solution in diethyl ether (20 ml) producing a white precipitate. The solvents/reagents were evaporated under reduced pressure and the residue azeotroped with diethyl ether twice. The residue was triturated with diethyl ether and filtered to leave the crude product as a white solid.

Yield 1.92 g. MS: APCI (+ve): 279 (M+1) (100%), 315 (M+HCl) (100%)

iii) (±)-3-[[5-(7-Ethyl-2-methyl-4H-benzo[5,6] cyclohepta[1,2-d]oxazol-4-yl)-3,4-dihydro-2,4-dioxo-1 (2H)-pyrimidinyl]methyl]-5-[imidazol-1-ylmethyl]benzoic acid, ethyl ester A solution of the product of example 3 step (vii) (2.5 g) in dry dimethylsulphoxide (30 ml) was treated with cesium carbonate (10 g) with stirring. After 20 min a solution of the product of step (ii) (1.5 g) in dimethylsulphoxide (10 ml) was added dropwise over 2 min. After 1.5 hours the reaction mixture was quenched with saturated brine and the product extracted into ethyl acetate. The organic phase was dried (MgSO$_4$) and the solvent was evaporated under reduced pressure to leave a brown gum. Column chromatography eluting with 10% methanol in ethyl acetate containing 1% triethylamine gave the product as a glass.

Yield: 0.92 g. MS: APCI (+ve): 578 (M+1) (100%)

iv) (±)-3-[[5-(7-Ethyl-2-methyl-4H-benzo[5,6]cyclohepta [1,2-d]oxazol-4-yl)-3,4-dihydro-2-oxo-4-thioxo-1(2H)-pyrimidinyl]methyl]-5-[imidazol-1-ylmethyl]benzoic acid, ethyl ester The subtitle compound was prepared from the product of step (iii) (0.92 g) according to the method of example 2 step (ii) as a yellow foam.

Yield: 0.45 g. MS: APCI (+ve): 594 (M+1) (100%)

v) (±)-3-[[5-(7-Ethyl-2-methyl-4H-benzo[5,6]cyclohepta [1,2-d]oxazol-4-yl)-3,4-dihydro-2-oxo-4-thioxo-1(2H)-pyrimidinyl]methyl]-5-[imidazol-1-ylmethyl]benzoic acid The title compound was prepared from the product of step (iv) (0.45 g) according to the method of example 1 step (ix) as a yellow solid. Yield 0.32 g. A small portion of this material (0.09 g) was subjected to purification by reverse phase chromatography eluting with 50% methanol in 1% aqueous ammonium acetate.

Yield 0.03 g. MS: APCI (+ve): 566 (M+1) (100%) 1H NMR: δ (DMSO) 7.99 (2xs, 3H), 7.6 (d, 1H), 7.40 (s, 1H), 7.20 (m, 4H), 6.95 (s, 1H), 6.62 (q, 2H), 5.86 (s, 1H), 5.33 (s, 2H), 4.95 (q, 2H), 2.5 (q, 2H), 2.40 (s, 3H), 1.10 (t, 3H). MP: 204° C. dec.

EXAMPLE 8

(±)-2-[[5-(7-Ethyl-2-methyl-4H-benzo[5,6] cyclohepta[1,2-d]oxazol-4-yl)-3,4-dihydro-2-oxo-4-thioxo-1(2H)-pyrimidinyl]methyl]-4-oxazolecarboxylic acid (i) (±)-2-[[5-(7-Ethyl-2-methyl-4H-benzo[5,6]cyclohepta [1,2-d]oxazol-4-yl)-3,4-dihydro-2,4-dioxo-1(2H)-pyrimidinyl]methyl]-4-oxazolecarboxylic acid, ethyl ester The subtitle compound was prepared from the product of example 3 step (vii) (2.2 g) and 2-bromomethyl-4-oxazolecarboxylic acid ethyl ester (0.52 g) using the method of example 1 step (viii). Purification was by chromatography eluting with ethyl acetate.

Yield 0.67 g. MS: APCI (+ve): 489 (M+1, 100%)

(ii) (±)-2-[[5-(7-Ethyl-2-methyl-4H-benzo[5,6] cyclohepta[1,2-d]oxazol-4-yl)-3,4-dihydro-2-oxo-4-thioxo-1(2H)-pyrimidinyl]methyl]-4-oxazolecarboxylic acid, ethyl ester The subtitle compound was prepared from the product of step (i) (0.67 g) using the method of example 2 step (ii). Purification was by chromatography eluting with 50% ethyl acetate in toluene.

Yield 0.51 g. MS: APCI (+ve): 505 (M+1, 100%)

(iii) (±)-2-[[5-(7-Ethyl-2-methyl-4H-benzo[5,6] cyclohepta[1,2-d]oxazol-4-yl)-3,4-dihydro-2-oxo-4-thioxo-1(2H)-pyrimidinyl]methyl]-4-oxazolecarboxylic acid The title compound was prepared from the product of step (ii) (0.45 g) using the method of example 1 step (ix).

Yield 0.4 g. MS: APCI (+ve): 477 (M+1, 100%) 1 H NMR: δ (DMSO) 12.87 (s, 1H), 8.8 (s, 1H), 7.65 (d, 1H), 7.3 (s, 1H), 7.2–7.25 (m, 2H), 6.84 (d, 1H), 6.74 (d, 1H), 5.93 (s, 1H), 5.08 (d, 1H), 5.04 (d, 1H), 2.58 (q, 2H), 2.4 (s, 3H), 1.15 (t, 3H). MP: 210° C.

EXAMPLE 9

(±)-3-[[5-(7-Ethyl-2-methyl-4H-benzo[5,6] cyclohepta[1,2-d]oxazol-4-yl)-3,4-dihydro-2-oxo-4-thioxo-1(2H)-pyrimidinyl]methyl]benzoic acid i) (±)-3-[[5-(7-Ethyl-2-methyl-4H-benzo[5,6]cyclohepta [1,2-d]oxazol-4-yl)-3,4-dihydro-2,4-dioxo-1(2H)-pyrimidinyl]methyl]benzoic acid, methyl ester The subtitle compound was prepared from the product of example 3 step (vii) (2. g) and 3-bromomethyl benzoic acid methyl ester (0.5 g) using the method of example 1 step (viii). Purification was by chromatography eluting with 60% ethyl acetate in toluene.

Yield 0.58 g. MS: APCI (+ve) 484 (M+1, 100%)

ii) (±)-3-[[5-(7-Ethyl-2-methyl-4H-benzo[5,6]cyclohepta [1,2-d]oxazol-4-yl)-3,4-dihydro-2-oxo-4-thioxo-1(2H)-pyrimidinyl]methyl]benzoic acid, methyl ester The subtitle compound was prepared from the product of step (i) (0.56 g) using the method of example 2 step (ii). Purification was by chromatography eluting with 30% ethyl acetate in toluene.

Yield 0.5 g. MS: APCI (+ve): 500 (M+1, 100%)

iii) (±)-3-[[5-(7-Ethyl-2-methyl-4H-benzo[5,6] cyclohepta[1,2-d]oxazol-4-yl)-3,4-dihydro-2-oxo-4-thioxo-1(2H)-pyrimidinyl]methyl]benzoic acid The title compound was prepared from the product of step (ii) (0.5 g) using the method of example 1 step (ix).

Yield 0.43 g. MS: APCI (+ve): 486 (M+1, 100%) 1 H NMR: δ (DMSO) 13.05 (br s, 1H), 12.75 (s, 1H), 7.9–8.0 (m, 1H), 7.84 (s, 1H), 7.59 (d, 1H), 7.5–7.6 (m, 2H), 7.27 (s, 1H), 7.1–7.2 (m, 2H), 6.75 (d, 1H), 6.68 (d, 1H), 5.86 (s, 1H), 4.99 (d, 1H), 4.85 (d, 1H), 2.55 (q, 2H), 2.4 (s, 3H), 1.14 (t, 3H).

MP: 168–180° C. (decomp)

EXAMPLE 10

(±)-3-[[5-(7-Ethyl-2-methyl-4H-benzo[5,6] cyclohepta[1,2-d]oxazol-4-yl)-3,4-dihydro-2-oxo-4-thioxo-1(2H)pyrimidinyl]methyl]-N-[5-(trifluoromethyl)-1H-1,2,4-triazol-3-yl] benzenecarboxamide The title compound was prepared from the product of example 9 step (iii) (0.35 g) using the method of example 6.

Yield 0.035 g. MS: APCI (+ve): 620 (M+1, 100%) 1H NMR: δ (DMSO) 12.75 (s, 1H), 8.20 (br s, 2H), 8.03 (dt, 1H), 7.8 (s, 1H), 7.7–7.5 (m, 3H), 7.23 (s, 1H), 7.17 (dd, 1H), 7.09 (d, 1H), 6.64 (s, 2H), 5.87 (s, 1H), 2.5 (q, 2H), 2.35 (s, 3H), 1.15 (t, 3H). MP: 142–145° C.

EXAMPLE 11

(±)-3-[[5-(7-Ethyl-9,10-dihydro-2-methyl-4H-benzo [5,6]cyclohepta[1,2-d]oxazol-4-yl)-3,4-dihydro-2-oxo-4-thioxo-1(2H)-pyrimidinyl]methyl]benzoic acid i) (±)-4-(2,4-Bis(1,1-dimethylethoxy)pyrimidin-5-yl)-7-ethyl-2-methyl-9,10-dihydro-4H-benzo[5,6]cyclohepta[1,2-d]oxazol-4-ol A stirred solution of the product from example 1 step (vi) (3.60 g) in tetrahydrofuran (30 ml) at −70° C. was treated dropwise with n-butyllithium (4.75 ml of a 2.5M solution in hexanes) and stirred for 30 minutes. A solution of the product from example 3 step (vi) (2.60 g) in tetrahydrofuran (30 ml) was added dropwise and the reaction stirred at room temperature for 3 hours. The reaction was partitioned between brine and ethyl acetate and the organics dried (MgSO$_4$) and evaporation under reduced pressure gave a brown oil. Purification was by column chromatography eluting with 50% ethyl acetate in isohexane.

Yield 4.06 g. 1H NMR: δ (CDCl$_3$) 7.87 (d, 1H), 7.78 (s, 1H), 7.12 (dd, 1H), 6.98 (s, 1H), 4.71 (s, 1H), 2.92 (m, 2H), 2.67 (m, 4H), 2.39 (s, 3H), 1.56 (s, 9H), 1.44 (s, 9H), 1.23 (m, 3H)

ii) (±)-5-(7-Ethyl-9,10-dihydro-2-methyl-4H-benzo[5,6]cyclohepta[1,2-d]oxazol-4-yl)-2,4(1H,3H)-pyrimidinedione A stirred solution of the product from step (i) (0.60 g) in dichloromethane (15 ml) was treated with triethylsilane (0.225 ml) and cooled to 0° C. Boron trifluoride etherate (0.65 ml) was added in four equal portions at 5 minute intervals and the reaction stirred at room temperature for 16 hours. The reaction was poured into saturated sodium bicarbonate solution (200 ml) and extracted with ethyl acetate. The extracts were dried (MgSO$_4$) and evaporated to give a yellow solid which was purified by reverse phase chromatography eluting with 50% to 80% methanol in 0.1% aqueous ammonium acetate.

Yield 0.38 g. MS: APCI (+ve) 338 (M+1, 100%)

iii) (±)-3-[[5-(7-Ethyl-9,10-dihydro-2-methyl-4H-benzo [5,6]cyclohepta[1,2-d]oxazol-4-yl)-3,4-dihydro-2,4-dioxo-1 (2H)-pyrimidinyl]methyl]benzoic acid, methyl ester The subtitle compound was prepared from the product of step (ii) (0.38 g) and methyl 3-[bromomethyl]benzoate according to the method of example 1 step (viii).

Yield 0.105 g. MS: APCI (+ve) 486 (M+1, 100%)

iv) (±)-3-[[5-(7-Ethyl-9,10-dihydro-2-methyl-4H-benzo [5,6]cyclohepta[1,2-d]oxazol-4-yl)-3,4-dihydro-2-oxo-4-thioxo-1(2H)-pyrimidinyl]methyl]benzoic acid, methyl ester The subtitle compound was prepared from the product of step (iii) (0.1 g) according to the method of example 2 step (ii).

Yield 0.045 g. MS: APCI (+ve) 502 (M+1, 100%)

v) (±)-3-[[5-(7-Ethyl-9,10-dihydro-2-methyl-4H-benzo [5,6]cyclohepta[1,2-d]oxazol-4-yl)-3,4-dihydro-2-oxo-4-thioxo-1(2H)-pyrimidinyl]methyl]benzoic acid The title compound was prepared from the product of step (iv) (0.045 g) according to the method of example 2 step (iii). Purification was by reverse phase chromatography eluting with 50% to 60% methanol in 0.1% aqueous ammonium acetate.

Yield 0.01 g. MS: APCI (−ve) 486 (M−1, 100%)

1H NMR: δ (DMSO) 7.90 (m, 2H), 7.65 (s, 1H), 7.45 (m, 3H), 6.94 (m, 2H), 5.61 (s, 1H), 5.08 (d, 1H), 4.96 (d, 1H), 2.94 (m, 2H), 2.70 (m, 2H), 2.50 (q, 2H), 2.28 (s, 3H), 1.12 (t, 3H)

EXAMPLE 12

(±)-3-[[5-(7-Ethyl-2-methyl-4H-benzo[5,6] cyclohepta[1,2-d]thiazol4-yl)-3,4-dihydro-2,4-dioxo-1(2H)-pyrimidinyl]methyl]benzoic acid i) 7-Ethyl-9,10-dihydro-2-methyl-4H-benzo[5,6]cyclohepta[1,2-d]thiazol4-one A stirred suspension of potassium tert-butoxide (1.80 g) in dry N,N-dimethylformamide (20 ml) was cooled to 5° C. and saturated with hydrogen sulphide. The product from example 3 step (vi) (1.00 g) was added and the reaction stirred at room temperature for 1 hour. The mixture was poured into ice, acidified to pH4 with 2N hydrochloric acid and extracted with ethyl acetate. The extracts were washed with brine, dried (MgSO$_4$) and evaporated to give an orange solid which was purified by chromatography eluting with 50% ethyl acetate in isohexane.

Yield 0.84 g. MS: APCI (+ve) 258 (M+1, 100%)

ii) (±)-4-(2,4-Bis(1,1-dimethylethoxy)pyrimidin-5-yl)-7-ethyl-2-methyl-9,10-dihydro-4H-benzo[5,6]cyclohepta[1,2-d]thiazol-4-ol The subtitle compound was prepared from the product of step (i) according to the method of example 11 step (i). Purification was by chromatography eluting with 20% ethyl acetate in isohexane.

Yield 0.907 g. 1H NMR: δ (DMSO) 7.89 (s, 1H), 7.23 (d, 1H), 7.04 (d, 1H), 6.98 (dd, 1H), 5.95 (s, 1H), 3.19 (m, 1H), 2.91 (t, 2H), 2.81 (m, 1H), 2.56 (q, 2H), 1.55 (s, 9H), 1.16 (m, 12H)

iii) (±)-5-(7-Ethyl-9,10-dihydro-4-hydroxy-2-methyl-4H-benzo[5,6]cyclohepta[1,2-d]thiazol-4-yl)-2,4(1H,3H)-pyrimidinedione A solution of the product from step (ii) (0.44 g) in glacial acetic acid (10 ml) was stirred at room temperature overnight. The reaction mixture was evaporated to dryness (azeotroped twice with toluene) and the residue triturated with diethyl ether to give a pink solid.

Yield 0.303 g. MS: APCI (−ve) 369 (M−1, 100%)

iv) (±)-3-[[5-(7-Ethyl-9,10-dihydro-4-hydroxy-2-methyl-4H-benzo[5,6]cyclohepta[1,2-d]thiazol-4-yl)-3,4-dihydro-2,4-dioxo-1(2H)-pyrimidinyl]methyl]benzoic acid, methyl ester The subtitle compound was prepared from the product of step (iii) (0.35 g) according to the method of example 15 step (i).

Yield 0.185 g. 1H NMR: δ (DMSO) 11.17 (s, 1H), 7.93 (m, 2H), 7.60 (m, 3H), 7.20 (d, 1H), 7.01 (d, 1H), 6.93 (dd, 1H), 5.95 (s, 1H), 5.06 (s, 2H), 3.87 (s, 3H), 3.38 (m, 1H), 2.93 (m, 3H), 2.53 (q, 2H), 2.46 (s, 3H), 1.15 (t, 3H)

v) (±)-3-[[5-(7-Ethyl-2-methyl-4H-benzo[5,6]cyclohepta [1,2-d]thiazol-4-yl)-3,4-dihydro-2,4-dioxo-1(2H)-pyrimidinyl]methyl]benzoic acid, methyl ester A solution of the product from step (iv) (0.18 g) in glacial acetic acid (6 ml) was stirred at 100° C. for 2 hours. The solution was evaporated to dryness (azeotroped twice with toluene) and the residue purified by chromatography eluting with ethyl acetate.

Yield 0.15 g. MS: APCI (+ve) 500 (M+1, 100%)

vi) (±)-3-[[5-(7-Ethyl-2-methyl-4H-benzo[5,6]cyclohepta[1,2-d]thiazol-4-yl)-3,4-dihydro-2,4-dioxo-1(2H)-pyrimidinyl]methyl]benzoic acid The title compound was prepared from the product of step (v) according to the method of example 2 step (iii). Purification was by reverse phase chromatography eluting with 50% to 60% methanol in 0.1% aqueous ammonium acetate.

Yield 0.014 g. MS: APCI (+ve) 486 (M+1, 100%) 1H NMR: δ (DMSO) 7.90 (m, 1H), 7.80 (s, 1H), 7.44 (m, 3H), 7.22 (dd, 1H), 7.14 (d, 1H), 6.98 (s, 1H), 6.79 (dd, 2H), 5.46 (s, 1H), 4.92 (d, 1H), 4.80 (d, 1H), 2.60 (s, 3H), 2.56 (q, 2H), 1.14 (t, 3H) MP: 159–161° C.

EXAMPLE 13

(±)-3-[[5-(2,7-Dimethyl-10H-benzo[4,5]cyclohepta[1,2-d]oxazol-10-yl)-3,4-dihydro-2-oxo-4-thioxo-1(2H)-pyrimidinyl]methyl]benzoic acid i) 5-(3-Methylphenyl)-3-oxopentanoic acid, ethyl ester Ethyl acetoacetate (74.5 ml) was added dropwise to a solution of lithium diisopropylamide (2.0M solution in heptane/tetrahydrofuran/ethylbenzene, 600 ml) in tetrahydrofuran (2.5 L) at 0° C. The mixture was stirred for 30 min then 3-methylbenzylbromide (79 ml) was added dropwise. The mixture was stirred for 1 hour at 0° C. then quenched with 2M HCl. The mixture was extracted with ethyl acetate, the extracts washed with water, dried (MgSO$_4$) and evaporated to give an oil which was purified by chromatography eluting with 5–10% ethyl acetate in isohexane.

Yield 84.7 g. MS: APCI (–ve) 233 (M–1, 100%)

ii) 2-Acetoxy-5-(3-methylphenyl)-3-oxopentanoic acid, ethyl ester

Lead tetraacetate (60 g) was added in 10 g portions over 1 hour to a stirred solution of the product from step (i) (40 g) in benzene (200 ml) at room temperature. The mixture was stirred for 0.5 hour, quenched with ice-cold water and extracted with ether. The extracts were washed with aqueous sodium bicarbonate, dried (MgSO$_4$) and evaporated to give an oil which was purified by chromatography eluting with 5–10% ethyl acetate in isohexane.

Yield 19.7 g. MS: APCI (–ve) 291 (M–1, 100%)

iii) 2-Methyl-4-[2-(3-methylphenyl)ethyl]-5-oxazolecarboxylic acid, ethyl ester

A mixture of the product from step (ii) (19.6 g) and ammonium acetate (25.8 g) in acetic acid (150 ml) was heated under reflux for 2 hours. The reaction mixture was evaporated to dryness and the residue partitioned between water and ethyl acetate. The organic phase was washed with aqueous sodium bicarbonate and water, dried (MgSO$_4$) and evaporated under reduced pressure. The product was used without purification in the next step.

MS: APCI (+ve) 274 (M+1, 100%)

iv) 2-Methyl-4-[2-(3-methylphenyl)ethyl]-5-oxazolecarboxylic acid

The subtitle compound was prepared from the product from step (iii) according to the method of example 1 step (ix). Purification was by trituration with ethyl acetate and isohexane.

Yield 11.0 g. MS: APCI (–ve): 244 (M–1, 100%)

v) 4,5-Dihydro-2,7-dimethyl-10H-benzo[4,5]cyclohepta[1,2-d]oxazol-10-one

Oxalyl chloride (4.8 ml) was added dropwise to a stirred suspension of the product from step (iv) (9.0 g) and N,N-dimethylformamide (3 drops) in dichloromethane (100 ml) at room temperature. After 2 hours the solvent was removed under reduced pressure. The residue was dissolved in 1,2-dichloroethane (140 ml), aluminium trichloride (14.7 g) added and the mixture heated under reflux for 1 hour. The reaction mixture was added slowly to a stirred mixture of ice and 1M HCl, then extracted with chloroform. The extracts were dried (MgSO$_4$) and evaporated under reduced pressure to 40 ml. The product was obtained by precipitation with isohexane.

Yield 5.52 g. MS: APCI (+ve) 228 (M+1, 100%)

vi) (±)-5-(4,5-Dihydro-10-hydroxy-2,7-dimethyl-10H-benzo[4,5]cyclohepta[1,2-d]oxazol-10-yl)-2,4-bis(1,1-dimethylethoxy)pyrimidine The subtitle compound was prepared from the product from step (v) (6.0 g) according to the method of example 11 step (i). The product was used without further purification in the next step.

Yield 11.37 g.

vii) (±)-5-(2,7-Dimethyl-10H-benzo[4,5]cyclohepta[1,2-d]oxazol-10-yl)-2,4(1H,3H)-pyrimidinedione A solution of the product from step (vi) (5.7 g) in acetic acid (20 ml) was added dropwise over 5 min to acetic acid heated at 100° C. The mixture was heated for a further 3 hours at 100° C., the solvent removed under reduced pressure and azeotroped with toluene. Purification was by chromatography eluting with 5% methanol in dichloromethane.

Yield 0.67 g MS: APCI (+ve) 322 (M+1, 100%)

viii) (±)-3-[[5-(2,7-Dimethyl-10H-benzo[4,5]cyclohepta[1,2-d]oxazol-10-yl)-3,4-dihydro-2,4-dioxo-1(2H)-pyrimidinyl]methyl]benzoic acid, methyl ester The subtitle compound was prepared from the product of step (vii) and methyl 3-(bromomethyl)benzoate (690 mg) by the method of example 1 step (viii).

Yield 309 mg. MS: APCI (+ve) 470 (M+1, 100%)

ix) (±)-3-[[5-(2,7-Dimethyl-10H-benzo[4,5]cyclohepta[1,2-d]oxazol-10-yl)-3,4-dihydro-2-oxo-4-thioxo-1(2H)-pyrimidinyl]methyl]benzoic acid, methyl ester The subtitle compound was prepared from the product of step (viii) (0.47 g) by the method of example 2 step (ii). Purification was by chromatography eluting with 30–50% ethyl acetate in isohexane.

Yield 245 mg. MS: APCI (+ve) 486 (M+1, 100%)

x) (±)-3-[[5-(2,7-Dimethyl-10H-benzo[4,5]cyclohepta[1,2-d]oxazol-10-yl)-3,4-dihydro-2-oxo4-thioxo-1(2H)-pyrimidinyl]methyl]benzoic acid The title compound was prepared from the product of step (ix) according to the method of example 2 step (iii). Purification was by precipitation from ethyl acetate with isohexane.

Yield 0.06 g. MS: APCI (+ve) 472 (M+1, 100%) 1H NMR: δ (DMSO) 13.15 (s, 1H), 12.83 (s, 1H), 7.93 (d, 1H), 7.80 (s, 1H), 7.54–7.46 (m, 3H), 7.17 (d, 1H), 7.14 (s, 1H), 7.07 (s, 1H), 6.57 (AB quartet, 2H), 6.12 (s, 1H), 4.87 (AB quartet, 2H), 2.37 (s, 3H), 2.26 (s, 3H) MP: 180° C.

EXAMPLE 14

(±)-5-(2,7-Dimethyl-4H-benzo[5,6]cyclohepta[1,2-d]oxazol-4-yl)-1-(3-methyl-5-(5-trifluoromethyl)-1H-1,2,4-triazol-3-yl)phenylmethyl-3,4-dihydro-4-thioxo-2(1H)pyrimidinone i) 2-(Hydroxyimino)-5-(3-methylphenyl)-3-oxopentanoic acid, ethyl ester Sodium nitrite (32 g) in water (60 ml) was added dropwise over 1 hour to a stirred solution of the product from example 13 step (i) (99.4 g) in acetic acid (200 ml) at a rate such that the internal temperature did not rise above 30° C. The solution was allowed to stir a further 1 hour before adding water (500 ml). After stirring for a further 24 h the reaction mixture was extracted with diethyl ether (×4). The combined ether extracts were washed with saturated sodium bicarbonate solution, and finally water before collecting the organic layer and drying over magnesium sulphate. The solution was filtered and the solvent evaporated under reduced pressure to leave the subtitle product.

Yield: 88 g 1H NMR: δ (DMSO) 13.23 (s, 1H), 7.15–7.20 (m, 1H), 6.95–7.05 (m, 3H), 4.25 (q, 2H), 3.1 (t, 2H), 2.8 (t, 2H), 2.22 (s, 3H), 1.2 (t, 3H)

ii) 2-(Acetylamino)-5-(3-methylphenyl)-3-oxopentanoic acid, ethyl ester

Zinc dust (10 micron, 150 g) was added portionwise to a stirred solution of the product from step (i) (88 g) in acetic acid (400 ml) and acetic anhydride (125 ml) keeping the internal temperature below 40° C. The solution was stirred at room temperature for a further 1 hour before adding water (500 ml) dropwise at such a rate so as to keep the internal temperature below 40° C. The mixture was stirred at room temperature for a further 16 h then filtered and the mother liquor extracted with chloroform. The organic extracts were further washed with brine and water, collected dried over magnesium sulphate and solvent removed under reduced pressure to give the subtitle product.

Yield: 70 g MS: APCI (+ve); 290 (M−1, 100%)

iii) 2-Methyl-5-(2-(3-methylphenyl)ethyl)-4-oxazole carboxylic acid, ethyl ester Thionyl chloride (200 ml) was added dropwise over 15 min to the product from step (ii) (70 g) with cooling provided by an ice bath. The mixture was then set at reflux for 1 h. After cooling to room temperature the thionyl chloride was evaporated under reduced pressure and the residue partitioned between ethyl acetate and saturated sodium bicarbonate solution. The organic layer was collected, dried over magnesium sulphate and solvent removed under reduced pressure. Purification of the residue was performed by flash chromatography eluting with 2% ethanol in dichloromethane.

Yield: 39 g MS: APCI (+ve); 274 (M+1, 30%, 228, 100%)

iv) 2-Methyl-5-(2-3-methylphenyl)ethyl)-4-oxazolecarboxylic acid

The product from step (iii) (39 g) was stirred in a solution of methanol (100 ml), water (50 ml) and lithium hydroxide hydrate (16.8 g). After 16 h the slurry was evaporated to remove the methanol and the residue partitioned between ethyl acetate and 2M hydrochloric acid. The organic layer collected, dried over magnesium sulphate and solvent removed under reduced pressure.

Yield: 33 g MS: APCI (+ve); 246 (M+1, 10%, 228, 100%)

v) 9,10-Dihydro-2,7-dimethyl-4H-benzo[5,6]cyclohepta[1,2-d]oxazol-4-one

The product of step (iv) (31 g) was stirred with oxalyl chloride (16.6 ml) in dichloromethane (300 ml) at room temperature for 2 h. The solvent/reagents were evaporated under reduced pressure to dryness. The residue was suspended in 1,2-dichloroethane (200 ml) and aluminium chloride (65 g) added. The mixture was then set at reflux for 1 h. The cooled reaction mixture was added to 1N HCl (1.5 L) and ice and then extracted with dichloromethane (×4). The combined extracts were dried over magnesium sulphate and solvent evaporated under reduced pressure. Purification was by flash chromatography eluting with 1% ethanol in dichloromethane to give the subtitle product.

Yield: 9 g MS: APCI (+ve); 228 (M+1, 100%)

vi) (±)-5-(9,10-Dihydro-4-hydroxy-2,7-dimethyl-4H-benzo[5,6]cyclohepta[1,2-d]oxazol-4-yl)-2,4(1H,3H)-pyrimidinedione To a solution of the product from example 1 step (vi) (9 g) in dry tetrahydrafuran (100 ml) under nitrogen at −78° C. was added n-butyllithium (2.5M, 14.3 ml) dropwise over 1 min. After 30 min a warm solution of the product from step (v) (6.73 g) in tetrahydrofuran (350 ml) was added rapidly via cannula. After further stirring for 1 h the cooling bath was removed and the mixture allowed to stir at room temperature for 30 min. The reaction mixture was quenched with saturated brine and extracted with ethyl acetate (×2). The combined organic extracts were dried over magnesium sulphate and solvent removed under reduced pressure to leave a pale yellow foam. This was dissolved in acetic acid (100 ml) and stirred at room temperature for 16 h. The solvent was evaporated under reduced pressure and the residue azeotroped with toluene (×2) to remove last traces of acetic acid. The remaining residue was triturated with diethyl ether/isohexane mixtures and filtered to give the subtitle product as a beige solid.

Yield: 11 g MS: APCI (−ve); 338 (M−1, 100%)

vii) N-(2-Cyanoethyl)-3,5-dimethylbenzenecarboxamide

A stirred suspension of 3,5-dimethylbenzoic acid (50 g) in dry dichloromethane (500 ml) was treated dropwise with oxalyl chloride (100 ml) and then set at reflux for 16 h. Another aliquot of oxalyl choride (50 ml) was added and reflux continued for a further 6 h. The solvents/reagents were removed under reduced pressure and the residue azeotroped with benzene (×2). The resultant yellow oil was dissolved in dry tetrahydrofuran to a final volume of 250 ml. This solution was added dropwise in five 50 ml portions alternating with five 67 ml portions of 1.0N aqueous sodium hydroxide into a stirred solution of 3-aminopropionitrile fumarate (42.7 g) in 1.0N aqueous sodium hydroxide (333 ml) at 0° C. under nitrogen. After addition was complete the reaction mixture was allowed to attain room temperature and further stirred for 16 h. Water (500 ml) was added and the mixture extracted with ethyl acetate (3×500 ml). The organic layer was further washed with saturated sodium bicarbonate solution (2×500 ml). The organic layer was collected, dried over magnesium sulphate and solvent evaporated under reduced pressure to give the subtitle product as a white solid.

Yield: 48.85 g MS: APCI (+ve); 203 (M+1, 100%), APCI (−ve); 201 (M−1, 100%)

viii) N-(2-Cyanoethyl)-3,5-dimethylbenzenecarbohydrazonamide

A mixture of the product from step (vii) (35.68 g) and phosphorus pentachloride (36.86 g) was stirred under a water-aspirator vacuum and heated at 100° C. giving rise to a yellow oil. The oil was further stirred at 100° C. under vacuum for a further 30 min. The boiling phosphorus oxychloride liberated was collected by distillation to leave a dark brown oil which was cooled to room temperature and dissolved in dry 1,4-dioxane (50 ml). This solution was transferred rapidly via cannula to a stirring solution of hydrazine in tetrahydrofuran (1.0M, 882 ml) under nitrogen at room temperature. An exotherm was produced raising the reaction temperature to ~40° C. The resultant opaque yellow solution was further stirred for 16 h. The solvent was removed under reduced pressure and the residue partitioned between ethyl acetate and water. The organic layer was collected, dried over magnesium sulphate and solvent removed under reduced pressure to give the subtitle product as a red oil (34.7 g). This was not purified but used directly in the next step ix) 3-(3,5-Dimethylphenyl)-5-trifluoromethyl-1H-1,2,4-triazole A solution of the crude product from step (viii) (34.7 g) in dichoromethane (50 ml) was added to trifluoroacetic anhydride (1200 ml) at 0° C., under nitrogen with stirring. The cooling bath was removed and the resultant bright-orange solution stirred at room temperature for a further 16 h. The solvent/reagent was removed under reduced pressure and the residue dissolved in ethyl acetate (500 ml) and extracted with 1.0N sodium hydroxide solution (3×200 ml) and saturated brine (400 ml), organic layer collected, dried over magnesium sulphate and solvent removed under reduced pressure to leave an orange solid. (42 g). This solid was dissolved in tetrahydrofuran (600 ml) and treated with 1N sodium hydroxide (157 ml). The resultant dark solution was stirred for 5 h. The reaction mixture was concentrated to dryness under reduced pressure and the residue treated with water (500 ml) and partitioned between ethyl acetate and 2N hydrochloric acid. The combined organic extracts were collected, dried over magnesium sulphate and solvent evaporated to leave a viscous red oil. Purification by flash chromatography eluting with 4:1 isohexane/ethyl acetate gave the subtitle product as a pale pink solid.

Yield: 17.47 g MS: APCI (+ve); 242 (M+1, 100%), APCI (−ve); (M−1, 100%)

x) 3-(3,5-Dimethylphenyl)-5-trifluoromethyl-4-(2-(trimethylsilyl)ethoxymethyl)-1,2,4-triazole A stirred solution of the product from step (ix) (17.46 g) in dry N,N-dimethylformamide (300 ml) was treated with 60% dispersion of sodium hydride (3.22 g) in portions at room temperature under nitrogen. After the initial effervescence had subsided the resultant orange oil was stirred for a further 30 min before being treated with 2 -(trimethylsilyl) ethoxymethyl chloride (14.3 ml) dropwise giving a pale yellow suspension which was further stirred for 30 min. The mixture was carefully poured onto water (700 ml) and extracted with ethyl acetate (3×250 ml). The combined organic extracts were further washed with water (3×250 ml) and saturated brine (250 ml) before collecting, drying over magnesium sulphate and evapoaration of the solvent under reduced pressure to give the subtitle product as a yellow oil. Yield: 26.1 g. This was not purified but used directly in the next step.

xi) 3-(3-Bromomethyl-5-methylphenyl)-5-trifluoromethyl-4-(2-(trimethylsilyl)ethoxymethyl)-1,2,4-triazole The product from step (x) (2 g), N-bromosuccinamide (1 g) in dry ethyl acetate (25 ml) was irradiated at reflux with a 500 Watt halogen lamp for 1 h. The cooled reaction mixture was partitioned with dilute sodium bicarbonate solution. The organic layer collected, dried (MgSO$_4$) and solvent removed by evaporation under reduced pressure. Yield:2.5 g The product was not purified but used directly in the next step.

xii) (±)-5-(4-Hydroxy-9,10-dihydo2,7-dimethyl- -4H-benzo[5,6]cyclohepta[1,2-d]oxazol-4-yl)-1-(3-methyl-5-(5-trifluoromethyl4-(2-(trimethylsilyl)ethoxymethyl)-1,2,4-triazol-3-yl)phenylmethyl-3,4-dihydro-2,4(1H,3H)-pyrimidinedione The product from step (xi) (2.5 g) was added to a stirred solution of the product of step (vi) (2.8 g), cesium carbonate (2.7 g) in dry dimethylsulphoxide (20 ml) at room tempera-ture. After 30 min. the reaction mixture was partitioned between brine and ethyl acetate. The organic layer was further washed with brine (×4), collected, dried over MgSO$_4$ and solvent removed under reduced pressure to leave a pale yellow foam. The crude product was purified by silica gel chromatography eluting with ethyl acetate to give the subtitle product as a colourless foam.

Yield: 0.75 g MS: APCI (+ve); 691 (M−18, 100%)

xiii) (±)-5-(2,7-Dimethyl-4H-benzo[5,6]cyclohepta[1,2-d]oxazol-4-yl)-1-(3-methyl-5-(5-trifluoromethyl)-1,2,4-triazol-3-yl)phenylmethyl-3,4-dihydro-2,4-dioxo-1(2H)pyrimidinedione The product from step (xii) (0.75 g) was dissolved in acetic acid (50 ml) and heated at reflux for 16 h. The solvent was removed and reduced pressure and replaced with trifluoroacetic acid (50 ml) and heated at reflux for 1 h. The solvent removed under reduced pressure. The residue purified by flash chromatography to give the subtitle product.

Yield: 0.32 g MS: APCI (+ve); 561 (M+1, 100%)

xiv) (±)-5-(2,7-Dimethyl-4H-benzo[5,6]cyclohepta[1,2-d]oxazol-4-yl)-1-(3-methyl-5-(5-trifluoromethyl)-1H-1,2,4-triazol-3-yl)phenylmethyl-3,4-dihydro-4-thioxo-2(1H)pyrimidinone The title compound was prepared from the product of step (xiii) (0.32 g) according to the method of example 2 step (ii). Purification was by flash chromatography eluting with 60/40 iso-hexane/ethyl acetate.

Yield: 0.05 g MS: APCI (+ve): 577 (M+1, 100%, APCI (−ve); 575 (M−1, 100%) 1H NMR: δ (DMSO) 15.32 (bs, 1H), 12.76 (bs, 1H), 7.87 (s, 1H), 7.70 (s, 1H), 7.58 (d, 1H), 7.25 (s, 1H), 7.20 (s, 1H), 7.15 (d, 1H), 7.0 (s, 1H), 6.60 (dd, 2H), 5.87 (s, 1H), 4.90 (q, 2H), 2.50 (s, 3H), 2.40 (s, 3H), 2.20 (3, 3H) MP: 184° C.

EXAMPLE 15

(±)-3-[5-(2,7-Dimethyl-4H-benzo[5,6]cyclohepta[1,2-d]oxazol-4-yl)-3,4-dihydro-2-oxo-4-thioxo-1(2H)-pyrimidinylmethyl]benzoic acid i) (±)-3-[9,10-Dihydro-4-hydroxy-2,7-dimethyl-4H-benzo[5,6]cyclohepta[1,2-d]oxazol-4-yl)-2,4-dioxo-(1H,3H)-pyrimidinylmethyl]benzoic acid methyl ester A mixture of the product from example 14 step (vi) (3.57 g) and cesium carbonate (3.43 g) in dry dimethyl sulphoxide (40 ml) was stirred for 20 minutes and treated dropwise with a solution of methyl 3-(bromomethyl)benzoate (1.21 g) in dry dimethyl sulphoxide (10 ml) and stirred for 4 hours. The solution was partitioned between brine and ethyl acetate. The organic extracts were washed with brine, dried (MgSO$_4$) and evaporated under reduced pressure to give a yellow foam. Purification was by flash column chromatography eluting with ethyl acetate.

Yield 1.08 g. 1H NMR: δ (DMSO) 11.21 (s, 1H), 7.95 (d, 1H), 7.91 (d, 1H), 7.76 (s, 1H), 7.65 (d, 1H), 7.56 (t, 1H), 7.05 (m, 2H), 6.89 (dd, 1H), 5.91 (s, 1H), 5.08 (s, 2H), 3.87 (s, 3H), 2.86 (m, 4H), 2.26 (s, 3H), 2.24 (s, 3H)

ii) (±)-3-[5-(2,7-Dimethyl-4H-benzo[5,6]cyclohepta[1,2-d]oxazol-4-yl)-3,4-dihydro-2,4-dioxo-1(2H)-pyrimidinylmethyl]benzoic acid, methyl ester A solution of the product from step (i) (1.07 g) in trifluoroacetic acid (30 ml) was stirred under reflux for 48 hrs. The solution was evaporated under reduced pressure and azeotroped twice with toluene. The residue was purified by flash column chromatography eluting with ethyl acetate.

Yield 0.41 g. MS: APCI (+ve): 470 (M+1, 100%), APCI (−ve): 468 (M−1, 100%)

iii) (±) 3-[5-(2,7-Dimethyl-4H-benzo[5,6]cyclohepta[1,2-d]oxazol-4-yl)-3,4-dihydro-2-oxo-4-thioxo-1(2H)-pyrimidinylmethyl]benzoic acid, methyl ester The subtitle compound was prepared from the product of step (ii) according to the method of example 2 step (ii). Purification was by flash column chromatography eluting with 30% to 100% ethyl acetate in isohexane.

Yield 0.26 g. MS: APCI (+ve): 486 (M+1, 100%), APCI (−ve): 484 (M−1, 100%)

iv) (±)-3-[5-(2,7-Dimethyl-4H-benzo[5,6]cyclohepta[1,2-d]oxazol-4-yl)-3,4-dihydro-2-oxo-4-thioxo-1(2H)-pyrimidinylmethyl]benzoic acid The title compound was prepared from the product of step (iii) (0.16 g) according to the method of example 1 step (ix). Purification was by reverse phase chromatography eluting with 40%–60% methanol in 0.1% aqueous ammonium acetate.

Yield 0.053 g MS: APCI (+ve): 472 (M+1, 100%), APCI (−ve): 470 (M−1, 100%) 1H NMR: δ (DMSO) 7.91 (d, 1H), 7.84 (s, 1H), 7.57 (d, 1H), 7.35 (t, 1H), 7.24 (d, 1H), 7.20 (s, 1H), 7.13 (d, 2H), 6.73 (dd, 2H), 5.85 (s, 1H), 4.94 (d, 1H), 4.74 (d, 1H), 2.39 (s, 3H), 2.21 (s, 3H).

EXAMPLE 16

(±)-1-Methyl-5-(2,7-dimethyl-4H-benzo[5,6]cyclohepta[1,2-d]oxazol-4-yl)-3,4-dihydro-4-thioxo-2(1H)-pyrimidinone i) (±)-1-Methyl-5-(9,10-dihydro-4-hydroxy-2,7-dimethyl-4H-benzo[5,6]cyclohepta[1,2-d]oxazol-4-yl)-2,4(1H,3H)-pyrimidinedione The subtitle compound was prepared from the product of example 14 step (vi) (1.55 g) and methyl iodide (0.284 ml) according to the method of example 15 step (i). Purification was by flash column chromatography eluting with 5% methanol in ethyl acetate.

Yield 0.20 g MS: APCI (−ve): 352 (M−1, 100%)

ii) (±)-1-Methyl-5-(2,7-dimethyl-4H-benzo[5,6]cyclohepta[1,2-d]oxazol-4-yl)-2,4(1H,3H)-pyrimidinedione The subtitle compound was prepared from the product of step (i) (0.55 g) according to the method of example 15 step (ii). Purification was by flash column chromatography eluting with 5% methanol in ethyl acetate.

Yield 0.20 g. MS: APCI (+ve): 336 (M+1, 100%)

iii) (±)-1-Methyl-5-(2,7-dimethyl-4H-benzo[5,6]cyclohepta[1,2-d]oxazol-4-yl)-3,4-dihydro-4-thioxo-2(1H)-pyrimidinone The title compound was prepared from the product from step (ii) (0.20 g) according to the method of example 2 step (ii). Purification was by flash column chromatography eluting with 2% methanol in dichloromethane.

Yield 0.039 g. MS: APCI (+ve): 352 (M+1, 100%), APCI (−ve): 350 (M−1, 100%) 1H NMR: δ (DMSO) 12.67 (s, 1H), 7.62 (d, 1H), 7.24 (s, 1H), 7.18 (d, 2H), 6.91 (d, 1H), 6.82 (d, 1H), 5.99 (s, 1H), 3.18 (s, 3H), 2.42 (s, 3H), 2.27 (s, 3H). MP: 146–150° C.

EXAMPLE 17

(±)-1-Methyl-5-(2,6-dimethyl-4H-benzo[5,6]cyclohepta[1,2-d]oxazol-4-yl)-3,4-dihydro-4-thioxo-2(1H)-pyrimidinone i) 5-(4-Methylphenyl)-3-oxopentanoic acid, ethyl ester The subtitle compound was prepared from 4-methylbenzyl bromide (76.7 g) according to the method of example 13 step (i). Purification was by flash column chromatography eluting with 10% diethyl ether in isohexane.

Yield 62 g. MS: APCI (+ve): 235 (M+1, 100%)

ii) 2-(Hydroxyimino)-5-(4-methylphenyl)-3-oxopentanoic acid, ethyl ester

The subtitle compound was prepared from the product of step (i) (62 g) according to the method of example 14 step (i).

Yield 69 g MS: APCI (−ve): 262 (M−1, 100%)

iii) 2-Acetylamino-5-(4-methylphenyl)-3-oxo-pentanoic acid, ethyl ester

The subtitle compound was prepared from the product of step (ii) (70 g) according to the method of example 14 step (ii).

Yield 73 g. 1H NMR: δ (DMSO) 8.65 (1H, d), 7.10–7.00 (m, 4H), 5.21 (d, 1H), 4.10 (q, 2H), 2.95–2.90 (m, 2H), 2.80–2.70 (m, 2H), 2.25 (s, 3H), 1.91 (s, 3H), 1.17 (t, 3H)

iv) 5-[2-(4-Methylphenyl)ethyl]-2-methyloxazole-4-carboxylic acid, ethyl ester

The subtitle compound was prepared from the product from step (iii) according to the method of example 14 step (iii).

Yield 26 g MS: APCI (+ve): 274 (M+1, 100%)

v) 5-[2-(4-Methylphenyl)ethyl]-2-methyloxazole-4-carboxylic acid

The subtitle compound was prepared from the product of step (iv) (26 g) according to the method of example 14 step (iv).

Yield 21.40 g MS: APCI (−ve): 244 (M−1, 100%)

vi) 9,10-Dihydro-2,6-dimethyl-4H-benzo[5,6]cyclohepta[1,2-d]oxazole-4-one

A mixture of the product from step (v) (21.5 g), polyphosphoric acid (120 g) and sulpholane (60 ml) was stirred at 130° C. for 2 days. The cooled mixture was poured onto ice/water and extracted with ethyl acetate. The extracts were washed with water, dried (MgSO$_4$) and evaporated. Purification was by flash column chromatography eluting with 2% ethyl acetate in dichloromethane followed by recrystallisation from ethyl acetate.

Yield 4.00 g. 1H NMR: δ (DMSO) 7.55 (br s, 1H), 7.33 (d, 1H), 7.28 (d, 1H), 3.20–3.00 (m, 4H), 2.49 (s, 3H), 2.33 (s, 3H)

vii) (±)-4-(2,4-Bis(1,1-dimethylethoxy)pyrimidin-5-yl)-9,10-dihydro-2,6-dimethyl-4H-benzo[5,6]cyclohepta[1,2-d]oxazol-4-ol The subtitle compound was prepared from the product of step (vi) (7.80 g) according to the method of Example 11 step (i). Purification was by flash column chromatography eluting with 1:1 ethyl acetate:isohexane.

Yield 10.65 g. 1H NMR: δ (DMSO) 8.13 (s, 1H), 7.12 (d, 1H), 6.99 (d, 1H), 6.93 (s, 1H), 5.90 (s, 1H), 3.29 (m, 1H), 2.74 (m, 3H), 2.29 (s, 3H), 2.17 (s, 3H), 1.57 (s, 9H), 1.14 (s, 9H).

viii) (±)-5-(9,10-Dihydro-4-hydroxy-2,6-dimethyl-4H-benzo[5,6]cyclohepta[1,2-d]oxazol-4-yl)-2,4(1H,3H)-pyrimidinedione The subtitle compound was prepared from the product of step (vii) (10.00 g) according to the method of example 12 step (iii).

Yield 7.15 g MS: APCI (−ve): 338 (M−1, 100%)

ix) (±)-1-Methyl-5-(9,10-dihydro-4-hydroxy-2,6-dimethyl-4H-benzo[5,6]cyclohepta[1,2-d]oxazol-4-yl)-2,4(1H,3H)-pyrimidinedione The subtitle compound was prepared from the product of step (viii) (7.10 g) according to the method of example 21 step (vi). Purification was by flash column chromatography eluting with 5% methanol in dichloromethane.

Yield 1.96 g MS: APCI (−ve): 352 (M−1, 100%)

x) (±)-1-Methyl-5-(2,6-dimethyl-4H-benzo[5,6]cyclohepta[1,2-d]oxazol-4-yl)-2,4(1H,3H)-pyrimidinedione The subtitle compound was prepared from the product of step (ix) (1.93 g) according to the method of example 15 step (ii). Purification was by flash column chromatography eluting with 2% methanol in dichloromethane.

Yield 0.275 g MS: APCI (+ve): 336 (M+1, 100%), APCI (−ve): 334 (M−1, 100%)

xi) (±)-1-Methyl-5-(2,6-dimethyl-4H-benzo[5,6]cyclohepta[1,2-d]oxazol-4-yl)-3,4-dihydro-4-thioxo-2(1H)-pyrimidinone The title compound was prepared from the product of step (x) (0.245 g) according to the method of example 2 step (ii). Purification was by flash column chromatography eluting with 30% acetone in isohexane.

Yield 0.057 g MS: APCI (+ve): 352 (M+1, 100%), APCI (−ve): 350 (M−1, 100%) 1H NMR: δ (DMSO) 12.68 (s, 1H), 7.55 (s, 1H), 7.33 (d, 1H), 7.19 (s, 1H), 7.10 (dd, 1H), 6.92 (d, 1H), 6.78 (d, 1H), 6.00 (s, 1H), 3,18 (s, 3H), 2.41 (s, 3H), 2.29 (s, 3H) MP: 238–240° C.

EXAMPLE 18

(±)-1-Methyl-5-(2,7-dimethyl-4H-benzo[5,6]cyclohepta[1,2-d]thiazol-4-yl)-3,4-dihydro-4-thioxo-2(1H)-pyrimidinone i) 2,7-Dimethyl-9,10-dihydro-4H-benzo[5,6]cyclohepta[1,2-d]thiazol-4-one.

A stirred suspension of potassium tert-butoxide (6.4 g), in N,N-dimethylformamide (60 ml) was saturated at 5° C. with hydrogen sulphide. The mixture was treated with the product from example 14 step (v) (3.4 g), stirred for 2 h and poured onto ice. The mixture was acidified to pH 4 with dilute hydrochloric acid, and extracted with ethyl acetate. The organic phase was collected, dried (MgSO$_4$) and evaporated under reduced pressure to give a solid. Recrystallised from ethyl acetate/isohexane gave a buff solid.

Yield 1.5 g MS: APCI (+ve): 244 (M+1, 100%)

ii) (±)-5-[9,10-Dihydro-4-hydroxy-2,7-dimethyl-4H-benzo[5,6]cyclohepta[1,2-d]thiazol-4-yl]-2,4(1H,3H)-pyrimidinedione The subtitle compound was prepared from the product of step (i) (1.9 g), by the method of example 14, step (vi).

Yield 1.5 g MS: APCI (−ve): 354 (M−1, 100%)

iii) (±)-5-[9,10-Dihydro-4-hydroxy-2,7-dimethyl-4H-benzo[5,6]cyclohepta[1,2-d]thiazol-4-yl]-1-methyl-2,4(1H,3H)-pyrimidinedione The subtitle compound was prepared from the product of step (ii) (0.7 g), by the method of example 21, step (vi).

Yield 0.22 g MS: APCI (+ve): 366 (M+1, 100%)

iv) (±)-1-Methyl-5-[2,7-dimethyl-4H-benzo[5,6]cyclohepta[1,2-d]thiazol-4-yl]-2,4(1H,3H)-pyrimidinedione.

A stirred solution of the product from step (iii) (0.22 g), in glacial acetic acid (5 ml) was stirred at 100° C. for 3 h and evaporated to give an oil. Yield: 190 mg. Used directly in the step.

v) (±)-1-Methyl-5-(2,7-dimethyl-4H-benzo[5,6]cyclohepta[1,2-d]thiazol-4-yl)-3,4-dihydro-4-thioxo-2(1H)-pyrimidinone The title compound was prepared from the product from step (iv) (0.19 g) according to the method of example 2 step (ii). Purification was by flash column chromatography eluting with 0 to 1% methanol in dichloromethane, followed by a second flash column eluting with 30% ethyl acetate in toluene.

Yield: 0.07 g. MS: APCI (+ve): 368 (M+1, 100%) 1H NMR: δ (DMSO) 2.27 (s, 3H), 2.62 (s, 3H), 3.26 (s, 3H), 6.05 (s, 1H), 7.03 (d of d, 2H), 7.16–7.25 (mult, 2H), 7.50–7.53 (mult, 2H), 12.65 (s1, H). MP: 235–237° C.

EXAMPLE 19

(±)-1-Methyl-5-(2,7-dimethyl-10H-benzo[4,5]cyclohepta[1,2-d]oxazol-10-yl)-2,4-(1H,3H)-pyrimidinedione The title compound was prepared from the product of example 13 step (vii) (0.66 g) and iodomethane (0.49 ml) according to the method of example 1 step (viii). Purification was by chromatography eluting with 5% methanol in dichloromethane.

Yield 0.315 g. MS: APCI (+ve) 336 (M+1, 100%) 1H NMR: δ (DMSO) 11.32 (s, 1H), 7.37 (d, 1H), 7.25 (s, 1H), 7.22 (d, 1H), 6.90 (d, 1H), 6.67 (s, 1H), 6.64 (d, 1H), 5.47 (s, 1H), 3.08 (s, 3H), 2.39 (s, 3H), 2.30 (s, 3H)

EXAMPLE 20

(±)-1-Methyl-5-(2,7-dimethyl-10H-benzo[4,5]cyclohepta[1,2-d]oxazol-10-yl)-3,4-dihydro-2-oxo-4-thioxo-1(2H)-pyrimidine The title compound was prepared from the product of example 19 (0.29 g) according to the method of example 2 step (ii). Purification was by chromatography eluting with 2% methanol in dichloromethane followed by a second column eluting with ethyl acetate.

Yield 0.080 g. MS: APCI (+ve) 352 (M+1, 100%) 1H NMR: δ (DMSO) 12.75 (s, 1H), 7.58 (d, 1H), 7.27 (s, 1H), 7.20 (d, 1H), 7.06 (s, 1H), 6.91 (d, 1H), 6.66 (d, 1H), 6.30 (s, 1H), 3.14 (s, 3H), 2.38 (s, 3H), 2.29 (s, 3H) MP: 235° C.

EXAMPLE 21

(±)-1-Methyl-5-(2,7-dimethyl-10H-benzo[4,5]cyclohepta[1,2-d]thiazol-10-yl)-3,4-dihydro-4-thioxo-2(1H)-pyrimidinone i) 2-Methyl-4-[2-(3-methylphenyl)ethyl]-5-thiazolecarboxylic acid, ethyl ester Bromine (4 ml) was added dropwise to a stirred mixture of the product from example 13 step (i) (15 g) in water at 0° C. After 15 min the mixture was partitioned between ether and water. The organic phase was separated, dried (MgSO$_4$) and evaporated under reduced pressure. The residue was dissolved in ethanol (200 ml), thioacetamide (4.8 g) added and the mixture heated at reflux for 3 h. The solvent was removed under reduced pressure and the residue partitioned between ethyl acetate and aqueous sodium hydrogencarbonate. The organic phase was separated, dried (MgSO$_4$) and evaporated under reduced pressure. Purification was by chromatography eluting with 5–10% ethyl acetate in isohexane.

Yield 12.85 g. MS: APCI (+ve) 290 (M+1, 100%)

ii) 2-Methyl-4-[2-(3-methylphenyl)ethyl]-5-thiazolecarboxylic acid

The subtitle compound was prepared from the product of step (i) (12.84 g) according to the method of example 1 step (ix). Purification was by trituration with ethyl acetate and isohexane.

Yield 8.23 g. 1H NMR: δ (DMSO) 7.11 (t, 1H), 6.99–6.94 (m, 3H), 3.24–3.20 (m, 2H), 2.85–2.81 (m, 2H), 2.60 (s, 3H), 2.22 (s, 3H)

iii) 4,5-Dihydro-2,7-dimethyl-10H-benzo[4,5]cyclohepta[1,2-d]thiazol-10-one

The subtitle compound was prepared from the product of step (ii) (7.0 g) according to the method of example 1 step (iii). Purification was by trituration with ethyl acetate and isohexane.

Yield 3.5 g. MS: APCI (+ve) 244 (M+1, 100%)

iv) (±)-10-(2,4-Bis(1,1-dimethylethoxy)pyrimidin-5-yl)-4,5-dihydro-2,7-dimethyl-10H-benzo[4,5]cyclohepta[1,2-d]thiazol-10-ol The subtitle compound was prepared from the product of step (iii) (3.45 g) according to the method of example 11 step (i). Purification was by chromatography eluting with 1% methanol in dichloromethane.

Yield 3.22 g. MS: APCI (+ve) 468 (M+1)

v) (±)-5-(4,5-Dihydro-10-hydroxy-2,7-dimethyl-10H-benzo[4,5]cyclohepta[1,2-d]thiazol-10-yl)-2,4(1H,3H)-pyrimidinedione A solution of the product from step (iv) in acetic acid was stirred overnight. The solvent was removed under reduced pressure and the residue purified by chromatography eluting with 5–6% methanol in dichloromethane.

Yield 2.04 g. MS: APCI (+ve) 356 (M+1)

vi) (±)-1-Methyl-5-(4,5-dihydro-10-hydroxy-2,7-dimethyl-10H-benzo[4,5]cyclohepta[1,2-d]thiazol-10-yl)-2,4(1H,3H)-pyrimidinedione Sodium hydride (60% dispersion by wt) (112 mg) was added to a stirred solution of the product from step (v) (1.0 g) in N,N-dimethylformamide (20 ml) at room temperature. After 0.75 h, methyl iodide (0.175 ml) was added and stirring continued for 1 h. The mixture was quenched with water and extracted with ethyl acetate. The organic phase was washed with water, dried (MgSO$_4$) and evaporated under reduced pressure. Purification was by chromatography eluting with 5% methanol in dichloromethane.

Yield 0.14 g. MS: APCI (+ve) 370 (M+1)

vii) (±)-1-Methyl-5-(2,7-dimethyl-10H-benzo[4,5]cyclohepta[1,2-d]thiazol-10-yl)-2,4(1H,3H)-pyrimidinedione The subtitle compound was prepared from the product of step (vi) (0.18 g) by the method of example 12 step (v). Purification was by chromatography eluting with 3% methanol in dichloromethane.

MS: APCI (−ve) 350 (M−1)

viii) (±)-1-Methyl-5-(2,7-dimethyl-10H-benzo[4,5]cyclohepta[1,2-d]thiazol-10-yl)-4-thioxo-2(1H)-pyrimidinone The title compound was prepared from the product of step (vii) according to the method of example 2 step (ii). Purification was by chromatography eluting with ethyl acetate.

Yield 0.008 g. MS: APCI (+ve) 368 (M+1, 100%) 1H NMR: δ (DMSO) 12.75 (s, 1H), 7.31 (s, 1H), 7.29 (d, 1H), 7.22 (d, 1H), 7.12 (s, 1H), 7.04 (d, 1H), 6.96 (d, 1H), 6.08 (s, 1H), 3.17 (s, 3H), 2.56 (s, 3H), 2.31 (s, 3H)

EXAMPLE 22

(±)-5-[8-Methyl-5H-benzo[4,5]cyclohepta[1,2-b]pyridin-5-yl]-3,4-dihydro-4-thioxo-2(1H)-pyrimidinone i) (E)-2-[2-(3-Methylphenyl)ethenyl]pyridine-3-carboxylic acid.

A mixture of methyl 2-methylnicotinate (24.5 g), 3-methylbenzaldehyde (58 ml) and anhydrous zinc chloride (25 g) were heated at 180° C. under nitrogen for 0.5 hr. The reaction mixture was allowed to cool to room temperature and diluted with toluene (100 ml) and 10% NaOH solution (100 ml). This mixture was stirred for 0.5 hr and the resultant precipitate was removed by filtration. The aqueous phase was washed with toluene (3×50 ml) and acidified to pH5 by the addition of glacial acetic acid. The resultant precipitate was collected by filtration, washed with water and dried. Yield 10.88 g. The aqueous filtrate was extracted with chloroform (3×50 ml), the combined extracts were dried (MgSO$_4$) and evaporated under reduced pressure. Yield 6.02 g. Both crops were combined.

Total yield: 16.9 g MS: APCI (+ve): 240 (M+1, 100%).

ii) 8-Methyl-5H-benzo[4,5]cyclohepta[1,2-b]pyridin-5-one

A mixture of the product from step (i) (16.90 g) and polyphosphoric acid (300 ml) was heated at 180° C. for 4 hr. After cooling to room temperature the reaction mixture was added to ice/water and insoluble material was removed by filtration through Celite. The filtrate was adjusted to pH5 by the addition of 1M NaOH solution. and extracted with ethyl acetate (3×50 ml). The combined extracts were dried (NaSO$_4$) and evaporated under reduced pressure. Purification was by chromatography eluting with 30% ethyl acetate in toluene.

Yield 6.50 g. (The product was contaminated with 33 mole % of the corresponding 6-methyl isomer) MS: APCI (+ve): 222 (M+1, 100%).

iii) (±)-8-Methyl-5H-benzo[4,5]cyclohepta[1,2-b]pyridin-5-ol

A solution of the product from step (ii) (5.87 g) in dry tetrahydrofuran (50 ml) was treated with diisobutylaluminum hydride (4.7 ml) in one portion. The solution was stirred under nitrogen for 1.75 hr then partitioned between ethyl acetate and saturated brine. The organic phase was separated, dried (Na$_2$SO$_4$) and the solvent evaporated under reduced pressure. Purification was by chromatography eluting with 50% ethyl acetate in toluene.

Yield 3.56 g MS: APCI (+ve): 224 (M+1, 100%).

iv) (±)-5-[8-Methyl-5H-benzo[4,5]cyclohepta[1,2-b]pyridin-5-yl]-2,4(1H,3H)pyrimidinedione A solution of uracil (1.87 g) and the product of step (iii) (3.73 g) in glacial acetic acid (30 ml) was heated at 120° C. under nitrogen for 40 hr. The solvent was evaporated under reduced pressure and the residue was partitioned between ethyl acetate and saturated. sodium bicarbonate solution. The organic phase was separated, dried (MgSO$_4$) and evaporated under reduced pressure. Purification was by chromatography eluting with 0–20% methanol in ethyl acetate.

Yield 3.5 g. MS: APCI (+ve): 318 (M+1, 100%).

v) (±)-5-[8-Methyl-5H-benzo[4,5]cyclohepta[1,2-b]pyridin-5-yl]-3,4-dihydro-4-thioxo-2(1H)-pyrimidinone The title compound was prepared from the product of step (iv) (0.53 g) and Lawesson's reagent (0.675 g) according to the method of example 2 step (ii). Purification was by chromatography eluting with 50% acetone in iso-hexane followed by trituration with acetonitrile.

Yield 0.18 g. MS: APCI (+ve): 334 (M+1, 100%). 1H NMR: δ (DMSO) 12.39 (s, 1H), 11.26 (s, 1H), 8.44 (d of d, 1H), 8.08 (d of d, 1H), 7.45 (d, 1H), 7.34 (m, 2H), 7.26 (d of d, 1H), 7.17 (d, 1H), 7.01 (d, 1H), 6.65 (s, 1H), 5.73 (s, 1H), 2.32 (s, 3H). MP: >250° C.

EXAMPLE 23

(±)-1-Methyl-5-[8-Methyl-5H-benzo[4,5]cyclohepta[1,2-b]pyridin-5-yl]-3,4-dihydro-4-thioxo-2(1H)-pyrimidine i) (±)-1-Methyl-5-[8-methyl-5H-benzo[4,5]cyclohepta[1,2-b]pyridin-5-yl]-2,4-(1H,3H)pyrimidinedione A solution of the product of example 22 step (iv) (0.68 g) in dry N,N-dimethylformamide (10 ml) was treated in one portion with sodium hydride (60% dispersion by wt, 0.086 g). After 1 hr iodomethane (0.13 ml) was added and the solution was stirred for 16 hr. The reaction mixture was diluted with water (50 ml) and the mixture was extracted with ethyl acetate (3×20 ml). The combined extracts were dried ($Na_2SO_4$) and the solvent was evaporated under reduced pressure. Purification was by chromatography eluting with 50–60% acetone in isohexane.

Yield 0.15 g. MS: APCI (+ve): 332 (M+1, 100%).

ii) (±)-1-Methyl-5-[8-methyl-5H-benzo[4,5]cyclohepta[1,2-b]pyridin-5-yl]-3,4-dihydro-4-thioxo-2(1H)-pyrimidinone The title compound was prepared from the product of step (i) (0.2 g) and Lawesson's reagent (0.29 g) according to the method of example 2 step (ii). Purification was by chromatography eluting with 50% acetone in isohexane followed by trituration with isohexane/ethyl acetate.

Yield 0.044 g MS: APCI (+ve): 348 (M+1, 100%). 1H NMR: δ (DMSO) 12.59 (s, 1H), 8.44 (d, 1H), 8.08 (d, 1H), 7.44 (d, 1H), 7.32 (m, 2H), 7.25 (m, 2H), 7.03 (d, 1H), 6.97 (s, 1 H), 5.78 (s, 1 H), 3.19 (s, 3H), 2.32 (s, 3H). MP: 157–160° C.

EXAMPLE 24

(±)-1-Methyl-5-[2,7-dimethyl-4H-benzo[5,6]cyclohepta[1,2-d]thiazol-4-yl]-2,4(1H,3H)-pyrimidinedione A solution of the product from example 18 step (iii) (0.111 g) in glacial acetic acid (5 ml) was stirred at 100° C. for 3 h and evaporated. Purification of the residue was by flash chromatography, eluting with 40% acetone in isohexane to give the title compound.

MS: APCI (+ve): 352 (M+1, 100%) 1H NMR: δ (DMSO) 2.28 (s, 3H), 2.62 (s, 3H), 3.12 (s, 3H), 5.49 (s, 1H), 6.86 (fine d, 1H), 6.96 (d of d, 2H), 7.20–7.21 (mult, 2H), 7.36–7.39 (mult, 1H)

EXAMPLE 25

(±)-5-[7-Chloro-2-methyl-4H-benzo[5,6]cyclohepta[1,2-d]oxazol-4-yl]-1-methyl-2,4(1H,3H)-pyrimidinedione i) 5-(3-Chlorophenyl)-3-oxopentanoic acid, ethyl ester To a solution of LDA (2.0M solution in heptanes/tetrahydrofuran/ethylbenzene, 500 ml) in tetrahydrofuran (2 L) at 0° C. was added ethyl acetoacetate (62 ml). After 40 min 3-chlorobenzyl bromide (100 g) was added dropwise and the mixture was stirred at 0° C. for 1 hour. The reaction mixture was acidified with 2N HCl and the organic phase was concentrated under reduced pressure. The residue was dissolved in ethyl acetate and washed with water and brine, dried (MgSO$_4$) and evaporated. Purification was by chromatography eluting with 5–10% ethyl acetate in isohexane.

Yield 84.4 g. MS:APCI (–ve) 253 (M–1, 100%)

ii) 5-(3-Chlorophenyl)-2-hydroxyimino-3-oxo-pentanoic acid, ethyl ester

A solution of sodium nitrite (12.6 g) in water (25 ml) was added to a stirred solution of the product from step (i) (42.2 g) in acetic acid (50 ml) at <30° C. The reaction mixture was stirred at room temperature for 30 min. Water (75 ml) was added and the mixture was stirred for 2 hours and extracted with diethyl ether. The combined extracts were washed with water and saturated aqueous sodium bicarbonate solution. The organic layer was collected, dried (MgSO$_4$) and solvent evaporated under reduced pressure to give the subtitle product.

The product was used directly in the next step without further purification. MS: APCI (–ve) 282 (M–1, 100%)

iii) 2-Acetylamino-5-(3-chlorophenyl)-3-oxo-pentanoic acid, ethyl ester

To a stirred solution of the product from step (ii) in acetic acid (125 ml) and acetic anhydride (40 ml) was added zinc dust (45 g) portionwise at a rate to maintain the internal temperature <40° C. The mixture was stirred for 30 min and water (125 ml) was added at such a rate as to maintain the temperature at around 40° C. The mixture was stirred at room temperature for 2 hours and filtered. The mother liquor was extracted with dichloromethane and further washed with water. The organic layer was collected, dried (MgSO$_4$) and solvent evaporated under reduced pressure to give the subtitle product.

Yield 45.5 g. MS:APCI (–ve) 310 (M–1, 100%)

iv) 5-[2-(3-Chlorophenyl)ethyl]-2-methyloxazole-4-carboxylic acid, ethyl ester

Thionyl chloride (180 ml) was added to the product of step (iii) (45.5 g) at 0° C. The mixture was stirred at room temperature for 2 hours and heated at reflux for 40 min. The residue after evaporation under reduced pressure was dissolved in ethyl acetate and washed with saturated sodium bicarbonate solution. The organic phase was dried (MgSO$_4$) and solvent evaporated under reduced pressure. Purification was by chromatography eluting with 1–2% ethanol in dichloromethane to give the subtitle product as an orange oil.

Yield 24.56 g. MS: APCI (+ve) 294 (M+1, 100%)

v) 5-[2-(3-Chlorophenyl)ethyl]-2-methyloxazole-4-carboxylic acid

A solution of the product from step (iv) (24.36 g) and potassium hydroxide (9 g) in ethanol (250 ml) and water (20 ml) was stirred at room temperature for 4 hours and concentrated under reduced pressure. The residue was suspended in water, acidified with 2N HCl and extracted with ethyl acetate. The combined extracts were washed with water and saturated brine. The organic layer was collected, dried (MgSO$_4$) and solvent evaporated to give the subtitle product.

Yield 20 g. MS: APCI (+ve) 266 (M+1), 248 (100%)

vi) 7-Chloro-9,10-dihydro-2-methyl-4H-benzo[5,6]cyclohepta[1,2-d]oxazol-4-one

A suspension of the product from step (v) (19.5 g) in benzene (150 ml) and thionyl chloride (50 ml) was heated at reflux for 1 hour. The resultant solution was evaporated to dryness and the residue was dissolved in 1,2-dichloroethane (150 ml) and treated with aluminium chloride (50 g). The reaction mixture was heated at reflux for 2 hours, allowed to cool and poured onto ice. The resultant suspension was repeatedly extracted with dichloromethane. The combined organic extracts were dried (MgSO$_4$) and solvent evaporated under reduced pressure. Purification was by chromatography eluting with 1% ethanol in dichloromethane.

Yield 5 g. MS: APCI (+ve) 248 (M+1, 100%)

vii) (±)-5-[7-Chloro-9,10-dihydro-4-hydroxy-2-methyl-4H-benzo[5,6]cyclohepta[1,2-d]oxazol-4-yl]-2,4(1H,3H)-pyrimidinedione n-BuLi (2.5M in hexanes, 8.4 ml) was added to a solution of the product from example 1 step (vi) (5.76 g) in tetrahydrofuran (50 ml) at −78° C. The reaction mixture was stirred at −65° C. for 30 min. A solution of the product from step (vi) (4.8 g) in tetrahydrofuran (100 ml) was added and the mixture was stirred at −70° C. for 1.5 hours and room temperature for 1 hour. The reaction mixture was quenched with aqueous ammonium chloride and partitioned between ethyl acetate and water. The organic phase was washed with water and saturated brine, dried (MgSO$_4$) and solvent evaporated. The residue was dissolved in glacial acetic acid and the solution stirred for 16 h at room temperature. The solvent was evaporated and the residue was triturated with ethyl acetate/isohexane. The solid was filtered off and the filtrate purified by chromatography eluting with 5–10% methanol in dichloromethane to give a pale yellow solid.

Yield 2.05 g. MS: APCI (−ve) 358 (M−1, 100%)

viii) (±)-5-[7-Chloro-9,10-dihydro-4-hydroxy-2-methyl-4H-benzo[5,6]cyclohepta[1,2-d]oxazol-4-yl]-1-methyl-2,4(1H,3H)-pyrimidinedione To a stirred solution of the product from step (vii) (2.0 g) in tetrahydrofuran (20 ml) at 0° C. was added sodium hydride (60% dispersion by wt, 0.22 g). The mixture was stirred at 0° C. for 40 min and treated with methyl iodide (0.35 ml). The mixture was further stirred at 0° C. for 2 hours and room temperature for 24 hours then partitioned between ethyl acetate and water. The organic phase was washed with water and saturated brine, dried (MgSO$_4$) and solvent evaporated. Purification was by chromatography eluting with 10% ethanol in dichloromethane to give the product as a pale yellow solid.

Yield 0.92 g. 1H NMR: δ (CDCl$_3$) 8.17 (br s, 1H), 7.84 (d, 1H), 7.29 (dd, 1H), 7.21 (d, 1H), 6.94 (s, 1H), 4.96 (s, 1H), 3.29 (s, 3H), 3.14–2.73 (m, 4H), 2.42 (s, 3H).

ix) (±)-5-[7-Chloro-2-methyl-4H-benzo[5,6]cyclohepta[1,2-d]oxazol-4-yl]-1-methyl-2,4(1H,3H)-pyrimidinedione A solution of the product from step (viii) (0.85 g) in trifluoroacetic acid (20 ml) was heated at reflux for 8 days. The solvent was evaporated and the residue triturated with ethyl acetate/isohexane to give a solid.

Yield 0.5 g. 1H NMR: δ (DMSO) 11.29 (s, 1H), 7.55–7.52 (m, 2H), 7.43 (dd, 1H), 6.90 (s, 2H), 6.89 (s, 1H), 5.23 (s, 1H), 3.12 (s, 3H), 2.44 (s, 3H)

EXAMPLE 26

(±)-5-[7-Chloro-2-methyl-4H-benzo[5,6]cyclohepta[1,2-d]oxazol-4-yl]-1-methyl-3,4-dihydro-4-thioxo-2(1H)-pyrimidinone The title compound was prepared from the product of example 25 step (ix) (0.48 g) according to the method of example 2 step (ii). Purification was by HPLC (SFC; 0–45% methanol).

Yield 0.08 g. MS: APCI (+ve) 372 (M+1, 100%) 1H NMR: δ (DMSO) 12.72 (s, 1H), 7.76 (d, 1H), 7.55 (d, 1H), 7.42 (dd, 1H), 7.23 (s, 1H), 6.94 (q, 2H), 5.96 (s, 1H), 3.20 (s, 3H), 2.43 (s, 3H).

EXAMPLE 27

(S)-5-[7-Chloro-2-methyl-4H-benzo[5,6]cyclohepta[1,2-d]oxazol-4yl]-1-methyl-3,4-dihydro-4-thioxo-2(1H)-pyrimidinone The title compound was obtained from the product of example 26 by resolution of the racemate on HPLC (SFC; Chiralpak® AD column, 30–45% isopropanol in liquid CO$_2$). The title compound was the first enantiomer to be eluted off the column.

MS: APCI (+ve) 372 (M+1, 100%) 1H NMR: δ (DMSO) 12.72 (s, 1H), 7.76 (d, 1H), 7.55 (d, 1H), 7.42 (dd, 1H), 7.23 (s, 1H), 6.94 (q, 2H), 5.96 (s, 1H), 3.20 (s, 3H), 2.43 (s, 3H).

EXAMPLE 28

(±)-5-(7-Chloro-2-(2-(imidazol-1-yl)ethoxy)-4H-benzo[5,6]cyclohepta[1,2-d]thiazol-4-yl)-1-methyl-3,4-dihydro-4-thioxo-2(1H)-pyrimidinone i) 5-(7-Chloro-2-(2-(imidazol-1-yl)ethoxy)-4H-benzo[5,6]cyclohepta[1,2-d]thiazol-4-yl)-1-methyl-2,4(1H,3H)-pyrimidinedione The product from example 44 step (viii) (0.2 g), 1-(2-hydroxyethyl)imidazole (0.114 g) and 60% sodium hydride (0.048 g) in N,N-dimethylformamide (10 ml) was stirred under nitrogen at room temperature for 16 hours. The reaction mixture was partitioned between ethyl acetate and water. The organic phase was collected, dried (MgSO$_4$) and evaporated under reduced pressure to leave a yellow oil. Purification was by chromatography eluting with 10:1 dichloromethane/methanol to give the subtitle product as a yellow oil.

MS: APCI (+ve): 468 (M+1, 100%), APCI (−ve): 466 (M−1, 100%)

ii) (±)-5-7-Chloro-2-(2-(imidazol-1-yl)ethoxy)-4H-benzo[5,6]cyclohepta[1,2-d]thiazol-4-yl)-1-methyl-3,4-dihydro-4-thioxo-2(1H)-pyrimidinone The title product was prepared from the product of step (i) (0.15 g) according to the method of example 70. Purification was by chromatography eluting with 9:1 ethyl acetate/methanol to give a yellow solid.

Yield: 0.055 g MS: APCI (+ve): 485 (M+1, 100%) 1HNMR: δ (DMSO): 12.69 (brs, 1H), 7.68–6.85 (m, 8H), 5.77–5.75 (s, 1H), 4.69–4.66 (t, 2H), 4.41–4.39 (m, 2H), 3.29 (s, 3H) MP: 190–193° C.

EXAMPLE 29

(±)-1-[(1-Methyl)-1H-imidazol-2-ylmethyl]-5-(2,6-dimethyl-4H-benzo[5,6]cyclohepta[1,2-d]oxazol-4-yl)-3,4-dihydro-4-thioxo-2(1H)-pyrimidinone i) (±)-1-[(1-Methyl)-1H-imidazol-2-ylmethyl]-5-(9,10-dihydro-4-hydroxy-2,6-dimethyl-4H-benzo[5,6]cyclohepta[1,2-d]oxazol-4-yl)-2,4(1H,3H)-pyrimidinedione A solution of the product from example 17 step (viii) (1.39 g) in dry N,N-dimethylformamide (20 ml) was treated with sodium hydride (0.328 g of a 60% dispersion by wt.) and stirred for 0.5 h. 2-Chloromethyl-1-methyl-imidazole hydrochloride (J. Chem. Soc., Perkin1., 1993, 2298) (0.684 g) was added and stirring continued for a further 2 hours before being partitioned between ethyl acetate and saturated brine. The aqueous layer was continuously extracted with chloroform for 24 hours. The continuous extracts were evaporated and the residue triturated with 1:1 diethyl ether-:isohexane to give a pale yellow solid.

Yield 0.60 g MS: APCI (−ve): 432 (M−1, 100%)

ii) (±)-1-[(1-Methyl)-1H-imidazol-2-ylmethyl]-5-(2,6-dimethyl-4H-benzo[5,6]cyclohepta[1,2-d]oxazol-4-yl)-2,4(1H,3H)-pyrimidinedione The subtitle compound was prepared from the product of step (i) (0.60 g) according to the method of example 15 step (ii). Purification was by flash column chromatography eluting with 5% methanol in dichloromethane (+0.1% triethylamine).

Yield 0.60 g MS: APCI (+ve): 416 (M−1, 100%)

iii) (±)-1-[(1-Methyl)-1H-imidazol-2-ylmethyl]-5-(2,6-dimethyl-4H-benzo[5,6]cyclohepta[1,2-d]oxazol-4-yl)-3,4-dihydro-4-thioxo-2(1H)-pyrimidinone The title compound was prepared from the product from step (ii) (0.163 g) according to the method of example 2 step (ii). Purification was by flash column chromatography eluting with 5% methanol in dichloromethane.

Yield 0.02 g MS: APCI (+ve): 432 (M+1, 100%) 1H NMR: δ (DMSO) 12.77 (s, 1H), 7.51 (s, 1H), 7.29 (d, 1H), 7.18 (s, 1H), 7.14 (s, 1H), 7.09 (d, 1H), 6.88 (s, 1H), 6.76 (d, 1H), 6.61 (d, 1H), 5.93 (s, 1H), 4.94 (d, 1H), 4.82 (d, 1H), 3.54 (s, 3H), 2.40 (s, 3H), 2.29 (s, 3H)

EXAMPLE 30

(±)-5-(2,7-Dimethyl-4H-benzo[5,6]cyclohepta[1,2-d]thiazol-4-yl)-1-(2-(N-pyrrolidinyl)ethyl)-3,4-dihydro-4-thioxo-2(1H)-pyrimidinone i) (±)-5-(2,7-Dimethyl-4H-benzo[5,6]cyclohepta[1,2-d]thiazol-4-yl)-1-(2-(N-pyrrolidinyl)ethyl)-2,4(1H,3H)-pyrimidinedione The product from example 18 step (ii) (1.44 g) was dissolved in dry N,N-dimethylformamide (20 ml) and treated cautiously with sodium hydride (60% dispersion by wt, 0.5 g) under nitrogen. After 10 min 1-(2-chloroethyl)pyrrolidine hydrochloride (0.8 g) was added and the whole heated at 50° C. for 16 h. The reaction mixture was partitioned between water and ethyl acetate. The organic layer was collected, dried over magnesium sulphate and solvent evaporated under reduced pressure. Purification was by flash chromatography eluting with 9:1 dichloromethane/methanol. The product obtained was dissolved in acetic acid (10 ml) and heated at 100° C. for 2 h. The solvent was removed under reduced pressure. Purification was by flash chromatography eluting with dichloromethane/methanol mixtures to give the subtitle product as pale yellow foam.

Yield: 0.1 g MS: APCI+ve: (435 (M+1), 100%)

ii) (±)-5-(2,7-Dimethyl-4H-benzo[5,6]cyclohepta[1,2-d]thiazol-4-yl)-1-(2-(N-pyrrolidinyl)ethyl)-3,4-dihydro-4-thioxo-2(1H)-pyrimidinone The title product was prepared from the product of step (i) according to the method of example 2 step (ii). Purification was by flash chromatography eluting with dichloromethane/methanol/triethylamine mixtures followed by SFC chromatography eluting with a 20–45% CO$_2$/methanol gradient.

Yield. 0.011 g MS: APCI+ve: (451 (M+1), 100%), APCI (−ve): (449 (M−1, 100%) NMR: δ (CDCl$_3$): 9.35 (bs, 1H), 7.6 (d, 1H), 7.3–7.2 (m, 2H), 7.19 (d, 1H), 7.0–6.85 (dd, 2H), 6.21 (s, 1H), 3.8–3.6 (br hump, 2H), 2.7 (bs, 1H), 2.5 (bs, 2H), 1.8–1.4 (b multiplet, 4H), 2.7 (s, 3H), 2.30 (s, 3H) MP: 198° C.

EXAMPLE 31

(±)-5-(2-Ethyl-7-methyl-4H-benzo[5,6]cyclohepta[1,2-d]thiazol-4-yl)-3,4-dihydro-4-thioxo-2(1H)-pyrimidinone i) 2-Ethyl-9,10-dihydro-7-methyl-4H-benzo[5,6]cyclohepta[1,2-d]thiazol-4-one Hydrogen sulphide was passed through a suspension of potassium tert-butoxide (9.31 g) in N,N-dimethylformamide (80 ml) at 5° C. until the mixture was saturated. The product from example 1 step (v) (5.0 g) was added and the reaction mixture stirred at room temperature for 2 h. The mixture was poured onto ice, acidified to pH3 and extracted with ethyl acetate. The organic phase was washed with water, dried (MgSO$_4$) and evaporated under reduced pressure. Purification was by chromatography eluting with 40–50% ethyl acetate in isohexane.

Yield 3.15 g. MS: APCI (+ve) 258 (M+1, 100%)

ii) 2-Ethyl-7-methyl-4H-benzo[5,6]cyclohepta[1,2-d]thiazol-4-one

A solution of the product from step (i) (3.14 g) and N-bromosuccinimide (2.18 g) in benzene (40 ml) was irradiated with a 500 Watt halogen lamp for 2 h. The reaction mixture was partitioned between dichloromethane and water. The organic phase was further washed with water, collected, dried (MgSO$_4$) and solvent evaporated under reduced pressure. The residue was dissolved in dichloromethane (25 ml) and triethylamine (10 ml) added. After stirring for 16 h the solvent/reagent were evaporated under reduced pressure. Purification was by chromatography eluting with 30–40% ethyl acetate in isohexane.

Yield 0.88 g. MS: APCI (+ve) 256 (M+1, 100%)

iii) (±)-2-Ethyl-7-methyl-4H-benzo[5,6]cyclohepta[1,2-d]thiazol-4-ol

Sodium borohydride (78 mg) was added to a stirred solution of the product from step (ii) (0.87 g) in dichloromethane (4 ml) and ethanol (16 ml) at 5° C. The reaction mixture was stirred for 2.5 h, warmed to room temperature and left for 2 h before a further 200 mg of sodium borohydride was added. The reaction mixture was quenched with 1M sodium hydroxide solution then partitioned between dichloromethane and water. The organic phase was washed with water, dried (MgSO$_4$) and evaporated under reduced pressure.

Yield 0.845 g. MS: APCI (+ve) 258 (M+1)

iv) (±)-5-(2-Ethyl-7-methyl-4H-benzo[5,6]cyclohepta[1,2-d]thiazol-4-yl)-2,4(1H,3H)-pyrimidinedione A solution of the product from step (iii) (785 mg) in acetic acid (5 ml) was added to a suspension of uracil (0.673 g) in acetic acid (25 ml) at 90° C. over 3 min. After 1.5 h the solvent was removed under reduced pressure and the residue partitioned between ethyl acetate and water. The organic phase was washed with water, dried (MgSO$_4$) and evaporated under reduced pressure. Purification was by chromatography eluting with ethyl acetate.

Yield 0.408 g. MS: APCI (+ve): 352 (M+1, 100%)

v) (±)-5-(2-Ethyl-7-methyl-4H-benzo[5,6]cyclohepta[1,2-d]thiazol-4-yl)-3,4-dihydro-4-thioxo-2(1H)-pyrimidinone The title compound was prepared from the product of step (iv) (0.385 g) by the method of example 2 step (ii). Purification was by chromatography eluting with 70% ethyl acetate in isohexane.

Yield 0.268 g. MS: APCI (+ve) 368 (M+1, 100%) 1H NMR: δ (DMSO) 12.47 (s, 1H), 11.40 (d, 1H), 7.50 (d, 1H), 7.27 (d, 1H), 7.22 (s, 1H), 7.19 (d, 1H), 7.08–6.66 (AB, 2H), 6.04 (s, 1H), 2.94 (q, 2H), 2.28 (s, 3H), 1.27 (t, 3H)

EXAMPLE 32

(±) 5-(2-Ethyl-7-methyl-4H-benzo[5,6]cyclohepta[1,2-d]thiazol-4-yl)-1-(N-methyl)imidazol-2-ylmethyl)-3,4-dihydro-4-thioxo-2(1H)-pyrimidinone i) (±)-5-(2-Ethyl-7-methyl-4-H-benzo[5,6]cyclohepta[1,2-d]thiazol-4-yl)-4-methylthio-2(1H)-pyrimidinone Methyl iodide (0.044 ml) was added to a stirred solution of the product from example 31 step (v) (0.250 g) and sodium bicarbonate (0.057 g) in ethanol (5 ml) and water (3 ml). After 3 h the reaction mixture was partitioned between ethyl acetate and water. The organic phase was washed with water, dried (MgSO$_4$) and evaporated under reduced pressure. Purification was by trituration with ethyl acetate and isohexane.

Yield 0.140 g. MS: APCI (+ve): 382 (M+1, 100%)

ii) (±)-5-(2-Ethyl-7-methyl-4H-benzo[5,6]cyclohepta[1,2-d]thiazol-4-yl)-1-(N-methyl)imidazol-2-ylmethyl)-3,4-dihydro-4-thioxo-2(1H)-pyrimidinone Sodium hydride (60% dispersion by wt. 25 mg) was added to a stirred solution of the product from step (i) in N,N-dimethylformamide (3 ml) at room temperature. After 0.25 h a solution of 2-chloromethyl-1-methyl-imidazole hydrochloride (J. Chem. Soc. Perkin 1., 1993, 2298) (41 mg) in N,N-dimethylformamide (1 ml) was added and the mixture stirred for 3 h at room temperature. Pyridine (5 ml), diisopropylethylamine (1 ml) and triethylamine (1 ml) were added and hydrogen sulphide gas bubbled through the mixture for 0.5 h. The reaction mixture was stirred at room temperature for a further 16 h and the solvent evaporated under reduced pressure. Purification was by chromatography eluting with triethylamine-methanol-dichloromethane (2:50:950), followed by HPLC (SFC; 20–45% 0.1% diethylamine in methanol), followed by a C-18 Sep-Pak column eluting with 50–60% methanol-water with 0.1% 0.88 ammonia).

Yield 0.011 g. MS: APCI (+ve): 462 (M+1, 100%) 1H NMR: δ (DMSO) 9.52 (s, 1H), 7.64 (d, 1H), 7.20 (s, 1H), 7.18 (d, 1H), 7.08 (s, 1H), 7.06 (d, 1H), 6.91 (1H, d), 6.75–6.67 (AB, 2H), 6.19 (s, 1H), 4.99 (d, 1H), 4.84 (d, 1H), 3.58 (s, 3H), 2.96 (q, 2H), 2.31 (s, 3H), 1.34 (t, 3H)

EXAMPLE 33

(±)-5-(2-Ethyl-7-methyl-4H-benzo[5,6]cyclohepta[1,2-d]thiazol-4-yl)-1-(2-(N,N-dimethyl)ethyl)-3,4-dihydro-4-thioxo-2(1H)-pyrimidinone Sodium hydride (60% dispersion by wt. 83 mg) was added to a stirred solution of the product from example 32 step (i) (318 mg) in dry N,N-dimethylformamide (10 ml) at room temperature under nitrogen. After 20 min 2-dimethylaminoethyl chloride hydrochloride (130 mg) was added with stirring at room temperature for 1 h. The temperature was then raised to 80° C. for 2 h. A further 40 mg of 60% dispersion of sodium hydride and 2-dimethylaminoethyl chloride hydrochloride (60 mg) was added and heating continued at 80° C. for a further 1 h. The cooled mixture was then treated with NaSH.hydrate (200 mg) and the mixture heated at 80° C. for 1.5 h. The solvent was removed under reduced pressure and the residue purified by a C18 Sep-Pak column eluting with 30–70% methanol/water (containing 0.2% aq. Ammonia) to leave a solid residue after lyophilisation. Further purification was performed by SFC chromatography eluting with 8 to 30% gradient of methanol (containing 0.1% diethylamine)/CO$_2$ to give the give the title product as a yellow solid after trituration with isohexane/ethyl acetate and filtration.

Yield: 51 mg MS:APCI (+ve); 439 (M+1, 100%) 1HNMR δ (DMSO): 12.62 (s, 1H), 7.58 (s, 1H), 7.53 (d, 1H), 7.22 (s, 1H), 7.19 (d, 1H), 7.08–6.99 (d, 2H), 6.03 (s, 1H), 3.80–3.75 (m, 2H), 2.94 (m, 2H), 2.42 (t, 2H), 2.28 (s, 3H), 2.13 (s, 6H), 1.29 (t, 3H) MP: 155° C.

EXAMPLE 34

(±)-5-[2-methyl-4H-benzo[5,6]cyclohepta[1,2-d]oxazol-4-yl)-1-methyl-3,4-dihydro-4-thioxo-2(1H)-pyrimidinone i) (±)-5-(9,10-Dihydro-4-hydroxy-2-methyl-4H-benzo[5,6]cyclohepta[1,2-d]oxazol-4-yl)-2,4(1H,3H)-pyrimidinedione The subtitle compound was prepared from 9,10-dihydro-2-methyl-4H-benzo[5,6]cyclohepta[1,2-d]oxazol-4-one (2.0 g) (J. Med. Chem., 1974, 17, 1316) according to the method of example 14 step (vi).

Yield 2.0 g. MS: APCI (–ve): 324 (M–1, 100%)

ii) (±)-5-(9,10-Dihydro-4-hydroxy-2-methyl-4H-benzo[5,6]cyclohepta[1,2-d]oxazol-4-yl)-1-methyl-2,4(1H,3H)-pyrimidinedione The subtitled compound was prepared from the product from step (i) (1.9 g) according to the method of example 21, step (vi). Purification was by flash column chromatography on silica eluting with 3 to 8% ethanol in dichloromethane to give the subtitle product.

Yield: 0.29 g MS: APCI (–ve): 338 (M–1, 100%)

iii) (±)-5-(2-Methyl-4H-benzo[5,6]cyclohepta[1,2-d]oxazol-4-yl)-1-methyl-2,4(1H,3H)-pyrimidinedione A stirred solution of the product from step (ii) (280 mg) in trifluoroacetic acid (5 ml), was heated under reflux for 96 h and evaporated. The residue was slurried in toluene and evaporated (twice). Purification was by flash chromatography eluting 50% acetone in isohexane, followed by a second column eluting with 4% ethanol in dichloromethane to give a yellow solid. Yield 75 mg. Used directly in the next step.

iv) (±)-5-[2-methyl-4H-benzo[5,6]cyclohepta[1,2-d]oxazol-4-yl)-1-methyl-3,4-dihydro-4-thioxo-2(1H)-pyrimidinone A mixture of the product from step (iii), (0.075 g) and Lawesson's reagent (0.094 g) in 1,4-dioxane (5 ml) under nitrogen was heated at reflux 16 h. The reaction mixture was partitioned between ethyl acetate and saturated brine. The organic phase was collected, dried over magnesium sulphate and solvent evaporated under reduced pressure. Purification was by flash chromatogaphy eluting with 0 to 2% ethanol in dichloromethane followed by a second column eluting with 40% ethyl acetate in toluene to give the title compound as a yellow solid.

Yield: 0.037 g MS: APCI (+ve): 338 (M+1, 100%) 1H NMR: δ (DMSO) 2.42 (s, 3H), 3.19 (s, 3H), 6.01 (s, 3H), 6.86 (d, 1H), 6.98 (d, 1H), 7.24 (s, 1H), 7.28 (d of t, 1H), 7.37 (d of t, 1H), 7.44 (d of d, 1H), 7.75 (d, 1H), 12.96 (s, 1H).

EXAMPLE 35

(±)-1-Methyl-5-(2-methyl-7-ethyl-4H-benzo[5,6]cyclohepta[1,2-d]thiazol-4-yl)-3,4-dihydro-4-thioxo-2(1H)-pyrimidinone 3-Ethylphenylmethanol n-Butyllithium (34 ml of a 2.5M solution in hexanes) was added to a solution of 1-bromo-3-ethylbenzene (15 g) in tetrahydrofuran (320 ml) at –78° C. After 1 hour N,N-dimethylformamide (15 ml) was added. The mixture was stirred at –78° C. for 1 hour and allowed to warm to room temperature. The mixture was quenched with aqueous ammonium chloride and partitioned between ethyl acetate and water. The organic phase was dried (MgSO$_4$) and evaporated. The residue was dissolved in methanol (250 ml) and treated with sodium borohydride (1.51 g) portionwise. The mixture was stirred at room temperature for 16 hours, quenched with 2M HCl (100 ml) and stirred for 4 hours. The mixture was concentrated under reduced pressure and the residue partitioned between ethyl acetate and 2M HCl. The organic phase was dried (MgSO$_4$), evaporated and the residue purified by chromatography eluting with 5–10% ethyl acetate in isohexane.

Yield: 7.6 g. MS: GC-MS: 136 (M+) 97% ii) 1-Bromomethyl-3-ethylbenzene

A mixture of the product from step (i) (29 g) and phosphorus tribromide (6.7 ml) in toluene (300 ml) was heated at reflux for 4 hours. After cooling to room temperature, the toluene layer was decanted from the brown phosphorus residues and concentrated under reduced pressure. The crude product was dissolved in diethyl ether (300 ml), washed with water, saturated aqueous sodium bicarbonate solution, and saturated brine. The organic phase was collected, dried ($MgSO_4$) and evaporated under reduced pressure.

Yield: 39 g 1H NMR: δ ($CDCl_3$) 7.2 (m, 4H), 4.49 (s, 2H), 2.65 (q, 2H), 1.22 (t, 3H).

iii) 5-(3-Ethylphenyl)-3-oxopentanoic acid, ethyl ester

To a stirred solution of ethyl acetoacetate (25 g) in tetrahydrofuran (800 ml) at 0° C. was added LDA (2.0M solution in heptanes/tetrahydrofuran/ethylbenzene) (194 ml). After 40 min the product from step (ii) (39 g) was added dropwise and the mixture was stirred at 0° C. for 1 hour. The reaction mixture was acidified with 2N HCl and the organic phase was concentrated under reduced pressure. The residue was dissolved in diethyl ether and washed with water and saturated brine. The organic phase was collected, dried ($MgSO_4$) and evaporated under reduced pressure. Purification was by chromatography eluting with 5–10% ethyl acetate in isohexane.

Yield: 20.6 g. MS:APCI (−ve) 247 (M−1, 100%)

iv) 5-(3-Ethylphenyl)-2-hydroxyimino-3-oxo-pentanoic acid, ethyl ester

A solution of sodium nitrite (6.3 g) in water (10 ml) was added to a stirred solution of the product from step (iii) (20.6 g) in acetic acid (30 ml) at <30° C. The reaction mixture was stirred at room temperature for 18 hours. Water (150 ml) was added and the mixture was stirred for 2 hours and extracted with diethyl ether. The combined extracts were washed with water and saturated aqueous sodium bicarbonate solution. The organic phase was collected, dried ($MgSO_4$) and solvent evaporated under reduced pressure.

Yield: 20.9 g MS: APCI (−ve) 276 (M−1, 100%)

v) 2-Acetylamino-5-(3-ethylphenyl)-3-oxo-pentanoic acid, ethyl ester

To a stirred solution of the product from step (iv) (20.9 g) in acetic acid (100 ml) and acetic anhydride (25 ml) was added zinc dust (30 g) portionwise at a rate to maintain the internal temperature <40° C. The mixture was stirred for 18 hours and water (125 ml) was added at such a rate as to maintain the temperature at around 40° C. The mixture was stirred at room temperature for 1 hour and filtered. The filtrate was extracted with dichloromethane and the extract was washed with water and saturated aqueous sodium bicarbonate solution. The organic phase was collected, dried ($MgSO_4$) and evaporated under reduced pressure to give a yellow oil.

Yield 21.1 g. MS:APCI (+ve) 306 (M+1, 50%)

vi) 5-[2-(3-Ethylphenyl)ethyl]-2-methyloxazole-4-carboxylic acid, ethyl ester

Thionyl chloride (80 ml) was added to the product from step (v) (21.0 g) at 0° C. The mixture was stirred at room temperature for 1 hour and heated at reflux for 1 hour. The residue after evaporation was dissolved in ethyl acetate and washed with saturated sodium bicarbonate solution. The organic phase was dried ($MgSO_4$) and evaporated.

Yield: 19.2 g. MS: APCI (+ve) 288 (M+1, 100%)

vii) 5-[2-(3-Ethylphenyl)ethyl]-2-methyloxazole-4-carboxylic acid

A solution of the product from step (vi) (19.0 g) and lithium hydroxide (5.6 g) in tetrahydrofuran (200 ml) and water (100 ml) was heated at reflux for 4 hours and concentrated under reduced pressure. The residue was suspended in water, acidified with 2N HCl and extracted with ethyl acetate. The combined extracts were washed with water and saturated brine. The organic phase was collected, dried ($MgSO_4$) and solvent evaporated to give a brown solid. Purification was by flash chromatography, eluting with 50% ethyl acetate in dichloromethane with 0.5% acetic acid.

Yield 9.7 g. MS: APCI (+ve) 260 (M+1) (100%)

viii) 7-Ethyl-9,10-dihydro-2-methyl-4H-benzo[5,6]cyclohepta[1,2-d]oxazole-4-one

A solution of the product from step (vii) (9.5 g) in thionyl chloride (100 ml) was stirred at room temperature for 4 days. After removal of solvent under reduced pressure, the residue was dissolved in 1,2-dichloroethane (200 ml) and treated with aluminium chloride (23 g). The reaction mixture was heated at reflux for 1 hour and allowed to cool. The resultant suspension was partitioned between 10% hydrochloric acid and dichloromethane. The combined extracts were evaporated, triturated with acetonitrile, and filtered through a plug of celite. Evaporation afforded a residue which was purified by chromatography eluting with 50–100% ethyl acetate in isohexane.

Yield 4.8 g. MS: APCI (+ve) 242 (M+1, 100%)

ix) 7-Ethyl-9,10-dihydro-2-methyl-4H-benzo[5,6]cyclohepta[1,2-d]thiazole-4-one

Hydrogen sulphide gas was bubbled through a solution of potassium tert-butoxide (17.4 g) in dimethylformamide (75 ml) at 0° C., maintaining the temperature below 5° C., until a permanent blue colour appeared. The product from step (viii) was added to this solution, and the reaction mixture stirred at room temperature for 3 hours, before it was poured onto ice. The mixture was acidified to pH 4 with 10% hydrochloric acid and extracted with ethyl acetate. The combined extracts were dried ($MgSO_4$) and evaporated to give a brown solid. Purification was by chromatography, eluting with 50–100% ethyl acetate in isohexane.

Yield: 2.5 g. MS: APCI (+ve) 258 (M+1, 100%)

x) 7-(1-Bromoethyl)-2-methyl-4H-benzo[5,6]cyclohepta[1,2-d]thiazole-4-one

A stirred mixture of N-bromosuccinimide (2.1 g) and the product from step (ix) (2.0 g) in ethyl acetate (100 ml) was irradiated with a 500 Watt lamp for 3 hours at room temperature. The solvent was removed under reduced pressure and the residue redissolved in dichloromethane (100 ml). Triethylamine (0.82 ml) was added and the mixture stirred at room temperature for 2 hours. Evaporation of solvent under reduced pressure gave a residue which was purified by chromatography, eluting with 20% isohexane in ethyl acetate.

Yield: 0.94 g. 1H NMR: δ ($CDCl_3$) 8.76 (d, 1H), 7.74 (m, 2H), 7.23 (s, 2H), 5.29 (q, 1H), 2.84 (s, 3H), 2.11 (d, 3H).

xi) (±)-7-Ethyl-2-methyl-4H-benzo[5,6]cyclohepta[1,2-d]thiazol-4-ol

A solution of sodium borohydride (0.31 g) and the product from step (x) (1.35 g) in 1,4-dioxan (40 ml) and dimethyl sulphoxide (10 ml) was stirred at room temperature for 18 hours. The reaction was quenched with water (4 ml) before solvent was removed under reduced pressure. The residue was dissolved in ethyl acetate which was washed with saturated aqueous sodium bicarbonate and saturated brine. The organic phase was collected, dried (MgSO₄) and evaporation of solvent under reduced pressure gave a yellow oil which was purified by chromatography, eluting with 20% isohexane in ethyl acetate.

Yield: 0.45 g. 1H NMR: δ (CDCl₃) 7.60 (d, 1H), 7.32 (dd, 1H), 7.26 (d, 1H), 7.09 (d, 1H), 6.90 (d, 1H), 5.74 (br s, 1H), 2.69 (s, 3H), 2.68 (q, 2H), 1.24 (t, 3H).

xii) (±)-5-[7-Ethyl-2-methyl-4H-benzo[5,6]cyclohepta[1,2-d]thiazol-4-yl]-1-methyl-2,4(1H,3H)-pyrimidinedione 1-Methyluracil (0.064 g) was added to a solution of the product from step (xi) (0.10 g) in dichloromethane (2 ml), followed by trifluoroacetic acid (1 ml). The orange solution was stirred at room temperature for 10 minutes before the solvent was removed under reduced pressure. The residue was azeotroped twice with acetonitrile, and the crude product purified by chromatography, eluting with 0–5% methanol in ethyl acetate.

MS: APCI (+ve) 366 (M+1) (100%)

xiii) (±)-1-Methyl-5-(2-methyl-7-ethyl-4H-benzo[5,6]cyclohepta[1,2-d]thiazol-4-yl)-3,4-dihydro-4-thioxo-2-(1H)-pyrimidinone A mixture of the product of step (xii) (0.070 g) and Lawesson's reagent (0.077 g) in 1,4-dioxane (5 ml) was heated at reflux for 16 hours. The solvent was evaporated under reduced pressure. Purification was by chromatography eluting with 2% ethanol in dichloromethane to give the title compound.

Yield: 0.01 g. MS: APCI (+ve): 382 (M+1, 100%). 1H NMR: δ (CDCl₃) 9.31 (br s, 1H), 7.63 (d, 1H), 7.25 (dd, 1H), 7.18 (d, 1H), 7.13 (s, 1H), 6.98 (d, 1H), 6.81 (d, 1H), 6.26 (s, 1H), 3.28 (s, 3H), 2.68 (s, 3H), 2.64 (q, 2H), 1.23 (t, 3H). MP: 265° C.

EXAMPLE 36

(±)-1-Methyl-5-(2-methyl-7-n-propyl-4H-benzo[5,6]cyclohepta[1,2-d]thiazol-4-yl)-3,4-dihydro-4-thioxo-2(1H)-pyrimidinone i) 3-n-Propylphenylmethanol The subtitle product was prepared from 1-bromo-3-n-propylbenzene (81.5 g) according to the method of example 35 step (i) as a pale yellow oil.

Yield: 26.7 g NMR: δ (CDCl₃): 7.35–7.10 (m, 4H), 4.67 (s, 2H), 2.60 (t, 2H), 1.7 (quin, 2H), 0.90 (t, 3H)

ii) 1-Bromomethyl-3-n-propylbenzene

The subtitle product was prepared from the product of step (i) (26.7 g) according to the method of example 35 step (ii) as a colourless oil. Yield: 29.06 g. Used directly in the next step.

iii) 5-(3-n-Propylphenyl)-3-oxopentanoic acid, ethyl ester

The subtitle product was prepared from the product of step (ii) (29 g) according to the method of example 35 step (iii). Purification was by flash chromatography eluting with 5–10% ethyl acetate in iso-hexane.

Yield: 14.88 g MS: APCI (+ve); (263 (M+1), 245, 100%), APCI–ve; (261 (M–1), 100%)

iv) 5-(3-n-Propylphenyl)-2-hydroxyimino-3-oxo-pentanoic acid, ethyl ester

The subtitle product was prepared from the product of step (iii) (22.84 g) according to the method of example 35 step (iv).

Yield: 24.27 g MS:APCI (–ve); (290 (M–1, 100%)

v) 2-Acetylamino-5-(3-n-propylphenyl)-3-oxo-pentanoic acid, ethyl ester

The subtitle product was prepared from the product of step (iv) (24.25 g) according to the method of example 35 step (v).

Yield: 23.1 g MS:APCI (+ve); (320 (M+1), 230, 100%), APCI–ve; (318 (M–1), 272, 100%)

vi) 5-[2-(3-n-Propylphenyl)ethyl]-2-methyloxazole-4-carboxylic acid, ethyl ester The subtitle product was prepared from the product of step (v) (23.1 g) according to the method of example 35 step (vi).

Yield: 15.95 g MS: APCI (+ve); 302 (M+1, 100%)

vii) 5-[2-(3-n-Propylphenyl)ethyl]-2-methyloxazole-4-carboxylic acid

The subtitle product was prepared from the product of step (vi) (15.95 g) according to the method of example 35 step (vii).

Yield: 14.36 g MS:APCI (+ve); 274 (M+1, 256, 100%), APCI–ve; 272 (M–1, 100%)

viii) 9,10-Dihydro-2-methyl-7-n-propyl-4H benzo[5,6]cyclohepta[1,2-d]oxazol-4-one The subtitle product was prepared from the product of step (vii) (13.72 g) according to the method of example 35 step (viii).

Yield: 6.79 g MS: APCI (+ve); (256 (M+1, 100%)

ix) 9,10-Dihydro-2-methyl-7-n-propyl-4H-benzo[5,6]cyclohepta[1,2-d]thiazol-4-one The subtitle product was prepared from the product of step (viii) (6.78 g) according to the method of example 35 step (ix).

Yield: 3.38 g MS: APCI (+ve); 272 (M+1, 100%)

x) 2-Methyl-7-n-propyl-4H-benzo[5,6]cyclohepta[1,2-d]thiazol-4-one

The product from step (ix) (2.8 g) and N-bromosuccinamide were dissolved in ethyl acetate (30 ml) and irradiated with a 500 Watt halogen lamp at reflux for 2 h. The solvent was evaporated under reduced pressure and the solid residue dissolved in dichloromethane (30 ml) and treated with triethylamine (10 ml). After 2 h the solvents were removed under reduced pressure and the residue partitioned between water and ethyl acetate. The organic layer was collected and dried over MgSO₄. The solvent was evaporated under reduced pressure and the product purified by flash chromatography.

Yield: 3.1 g MS: APCI (+ve); 272 (M+1, 100%)

xi) (±)-2-Methyl-7-n-propyl-4H-benzo[5,6]cyclohepta[1,2-d]thiazol-4-ol

To a solution of the product from step (x) (3.1 g) in dry dimethylsulphoxide (30 ml) and dry 1,4-dioxane (90 ml) was added sodium borohydride (0.7 g). After stirring at room temperature for 24 h the reaction mixture was quenched with water and extracted with ethyl acetate. The organic layer was washed with saturated sodium bicarbonate solution, then brine. The organic layer was collected and dried over magnesium sulphate and solvent removed under reduced pressure to leave a pale yellow gum.

Yield: 1.4 g

MS: APCI (+ve); 254 (M–17, 100%)

xii) (±)-1-Methyl-5-(2-methyl-7-n-propyl-4H-benzo[5,6]cyclohepta[1,2-d]thiazol-4-yl)-2,4-(1H,3H)-pyrimidinedione A mixture of the 1-methyluracil (0.5 g) and the product from step (xi) in acetic acid (50 ml) was heated at reflux 2 h. The solvent was removed under reduced pressure and the residue partitioned between ethyl acetate/water. The organic layer collected and dried over $MgSO_4$. The solvent evaporated and the crude product purified by flash chromatography eluting with ethyl acetate.

Yield: 0.06 g MS: APCI+ve; 380 (M+1, 100%)

xiii) (±)-1-Methyl-5-(2-methyl-7-n-propyl-4H-benzo[5,6]cyclohepta[1,2-d]thiazol-4-yl)-3,4-dihydro-4-thioxo-2(1H)-pyrimidinone The title product was prepared from the product of step (xii) according to the method of example 35 step (xiii). Purification was by flash chromatography eluting with 60/40 toluene/ethyl acetate.

Yield: 0.03 g MS: APCI (+ve); 396 (M+1, 100%), APCI-Ve; 394 (M−1), 100%) 1HNMR δ ($CDCl_3$): 9.3 (bs, 1H), 7.64 (d, 1H), 7.22 (d, 1H), 7.18 (s, 1H), 7.17 (s, 1H), 7.0–6.80 (2xd, 2H), 6.26 (s, 1H), 3.37 (s, 3H), 2.68 (s, 3H), 2.58 (t, 2H), 1.60 (sextet, 2H), 0.96 (t, 3H) MP: 235° C.

EXAMPLE 37

(±)-1-Methyl-5-(2-methyl-4H-benzo[5,6]cyclohepta[1,2-d]imidazol-4-yl)-3,4-dihydro-4-thioxo-2(1H)-pyrimidinone i) 2-Methyl-4H-benzo[5,6]cyclohepta[1,2-d]oxazol-4-one A stirred mixture of 9,10-dihydro-2-methyl-4H-benzo[5,6]cyclohepta[1,2-d]oxazol-4-one (9.52 g) (J. Med. Chem., 1974, 17, 1316) and N-bromosuccinimide (7.95 g) in benzene (200 ml) was irradiated with a 500 Watt halogen lamp for 2 h. The mixture was then treated with N,N-diisopropylethylamine (15.5 ml) and set at reflux for 1 hour. The mixture was then partitioned between ethyl acetate and water. The organic phase was collected, dried ($MgSO_4$) and solvent evaporated under reduced pressure. Purification was by recrystallisation from ethyl acetate to give a buff solid.

Yield: 5.07 g MS: APCI (+ve); 212 (M+1, 100%)

ii) 2-Methyl-1-(4-methoxyphenylmethyl)-4H-benzo[5,6]cyclohepta[1,2-d]imidazol-4-one A stirred mixture of the product from step (i) (5.07 g) and 4-methoxybenzylamine (12 ml) was heated at 100° C. for 24 h. The excess 4-methoxybenzylamine was distilled off under reduced pressure. The remaining residue was purified by recrystallisation from ethyl acetate to give the subtitle product as a pale yellow powder.

Yield: 4.34 g MS: APCI (+ve); 331 (M+1, 100%)

iii) 2-Methyl-1-(4-methoxyphenylmethyl)-4H-benzo[5,6]cyclohepta[1,2-d]imidazol-4-ol To a stirred solution of the product from step (ii) (1 g) in ethanol (40 ml) and dichloromethane (20 ml) was added sodium borohydride (0.28 g). After 48 h the solvent was evaporated (without heat) under reduced pressure and the residue partitioned between dilute aqueous sodium hydroxide solution and dichloromethane. The organic phase was collected, dried, ($MgSO_4$) and solvent evaporated under reduced pressure to leave a yellow foam.

Yield: 1.08 g MS: APCI (+ve); 333 (M+1, 100%)

iv) (±)-1-Methyl-5-(2-methyl-4H-benzo[5,6]cyclohepta[1,2-d]imidazol-4-yl)-2,4(1H,3H)-pyrimidinedione A stirred solution of the product from step (iii) (0.819 g) in trifluoroacetic acid (20 ml) was heated at reflux for 1 h. 1-Methyluracil (0.311 g) was added and the reflux continued for 5 days. The solvent was evaporated under reduced pressure. The residue was purified by chromatography eluting with 10% methanol in dichloromethane to give the subtitle product as pale green glass.

Yield: 0.3 g MS: APCI (+ve): 321 (M+1, 100%), APCI (−ve); 319 (M−1, 100%)

v) (±)-1-Methyl-5-(2-methyl-4H-benzo[5,6]cyclohepta[1,2-d]imidazol-4-yl)-3,4-dihydro-4-thioxo-2(1H)-pyrimidinone The title product was prepared from the product of step (iv) (0.1 g) and Lawesson's reagent (0.378 g) according to the method of example 34 step (iv). Purification was by chromatography eluting with 0–5% methanol in dichloromethane followed by reverse phase HPLC using a 40 mm Novapak column eluting with 15–85% methanol in 0.1% aqueous ammonium acetate gradient over 9 min.

Yield: 0.015 g MS: APCI (+ve): 337 (M+1, 100%) 1HNMR δ ($CDCl_3$): 7.31–7.43 (m, 4H), 6.86 (d, 1H), 6.77 (s, 1H), 6.72 (d, 1H), 6.05 (s, 1H), 3.20 (s, 3H), 2.43 (s, 3H). MP: 280° C. (dec)

EXAMPLE 38

(±)-5-(7-Chloro-2-methyl-4H-benzo[5,6]cyclohepta[1,2-d]thiazol-4-yl)-3,4-dihydro-4-thioxo-2(1H)-pyrimidinone i) 7-Chloro-9,10-dihydro-2-methyl-4H-benzo[5,6]cyclohepta[1,2-d]thiazole-4-one To a solution of the product from example 25 step (vi) (21 g) in N,N-dimethylformamide (225 ml) was added $NaSH.H_2O$ (23.76 g) and the whole heated at 80° C. for 1 hour. After cooling to room temperature, 2M hydrochloric acid solution (250 ml) was added. Nitrogen gas was then bubbled through the solution for 5 min and the mixture then poured into water (2 L) and extracted with chloroform (×2). The organic phases were collected, dried ($MgSO_4$) and solvent evaporated to leave a cream solid.

Yield: 10.1 g MS: APCI (+ve): 266/4 (M+1, 100%)

ii) 7-Chloro-2-methyl-4H-benzo[5,6]cyclohepta[1,2-d]thiazole-4-one

A solution of the product from step (i) (6.05 g) in 1,2-dichloroethane (85 ml) with N-bromosuccinimide (4.1 g) was irradiated with a 500 Watt halogen lamp for 1 h. After cooling to room temperature, triethylamine (7 ml) was added with further stirring for 0.5 hours. The solvents were evaporated under reduced pressure and the residue triturated with acetone, filtered and then further washed with water and then dried under vacuum to leave the subtitle compound as a cream solid.

Yield: 3.41 g 1HNMR δ (DMSO): 8.51 (d, 1H), 8.10 (d, 1H), 7.80 (dd, 1H), 7.64 (d, 1H), 7.43 (d, 1H), 2.78 (s, 3H).

iii) (±)-7-Chloro-2-methyl-4H-benzo[5,6]cyclohepta[1,2-d]thiazol-4-ol

Sodium borohydride (0.3 g) was added portionwise to a suspension of the product from step (ii) (1 g) in a mixture of methanol (40 ml) and dichloromethane (30 ml) at room temperature. After 1 hour the reaction mixture was partitioned between dichloromethane and brine. The organic phase was collected, dried ($MgSO_4$) and evaporated under reduced pressure to leave a beige foam. Yield: 1 g. Used directly in the next step.

iv) (±)-5-(7-Chloro-2-methyl-4H-benzo[5,6]cyclohepta[1,2-d]thiazol-4-yl)-2,4(1H,3H)-pyrimidinedione The product from step (iii) (1 g) and uracil (3 g) were heated at 100° C. in acetic acid (200 ml) for 16 h. The solvent was evaporated under reduced pressure and the residue partitioned between ethyl acetate and brine. The organic phase was collected, dried (MgSO$_4$), and evaporated under reduced pressure to leave a beige solid. The solid was triturated with isohexane/ethyl acetate mixtures and filtered to leave a cream solid. Yield. 1.35 g Used directly in the next step.

v) (±)-5-(7-Chloro-2-methyl-4H-benzo[5,6]cyclohepta[1,2-d]thiazol-4-yl)-3,4-dihydro-4-thioxo-2(1H)-pyrimidinone The product from step (iv) (1.35 g) and Lawesson's reagent (1.85 g) were heated at reflux in dioxane (50 ml) under nitrogen for 16 h. The reaction mixture was partitioned between ethyl acetate and brine. The organic phase was collected, dried (MgSO$_4$), and evaporated under reduced pressure to leave a brown solid. The solid was triturated with ethyl acetate and filtered to leave a yellow solid.

Yield. 0.9 g MS: APCI (+ve): 374 (M+1, 100%), APCI (−ve): 372 (M−1) 1HNMR δ (DMSO): 12.55 (bs, 1H), 11.51 (bd, 1H), 7.64 (d, 1H), 7.62 (s, 1H), 7.42 (dd, 1H), 7.30 (s, 1H), 7.10 (dd, 2H), 6.0 (s, 1H), 2.63 (s, 3H)

EXAMPLE 39

(5S, 2R)-5-(7-Chloro-2-methyl-4H-benzo[5,6]cyclohepta[1,2-d]thiazol-4-yl)-1-(2-pyrrolidinylmethyl)-3,4-dihydro-4-thioxo-2(1H)-pyrimidinone i) (±)-5-(7-Chloro-2-methyl-4H-benzo[5,6]cyclohepta[1,2-d]thiazol-4-yl)-4-methylthio-2(1H)-pyrimidinone A suspension of the product from example 38, step (v) (1.8 g) in ethanol (200 ml) and sodium bicarbonate (0.5 g) in water (15 ml) was heated until a complete solution formed. After cooling to room temperature methyl iodide (0.33 ml) was added and the whole stirred for 18 h. Another aliquot of methyl iodide was added (0.2 ml) followed by heating at 50° C. for 4 h. The reaction mixture was concentrated under reduced pressure and then partitioned between dichloromethane and brine. The organic phase was collected, dried (MgSO$_4$) and evaporated under reduced pressure to leave a beige foam. Purification was by chromatography eluting with ethyl acetate/methanol mixtures to give the subtitle product as colourless solid.

Yield 1.5 g MS:APCI (+ve); 388 (M+1, 100%), APCI (−ve); 386 (M−1, 100%)

ii) (R)-N-(1,1-Dimethylethoxycarbonyl)-2-[[(4-methylsulphonyl)oxy]methyl]pyrrolidine p-Toluenesulphonyl chloride (1.04 g) was added in portions to a stirred solution of (R)-N-(1,1-dimethylethoxycarbonyl)-2-pyrrolidinemethanol (1 g) in pyridine (6 ml) under nitrogen at 0° C. The mixture was allowed to reach room temperature and further stirred for 20 h. The reaction mixture was partitioned between diethyl ether and water. The organic phase was collected and further washed with 1N HCl, saturated copper sulphate solution, and brine. The organic phase was collected, dried (MgSO$_4$) and evaporated under reduced pressure to leave a colourless oil.

Yield: 1.85 g MS: APCI (+ve); 297 (M−57, 100%) 1HNMR δ (CDCl$_3$): 7.79 (d, 2H), 7.36 (m, 2H), 4.10 (m, 1H), 3.90 (m, 2H), 3.30 (m, 2H), 1.6–2.0 (m, 4H), 1.20 (2×S, 9H) rotamers iii) (5S, 2R)-5-(7-Chloro-2-methyl-4H-benzo[5,6]cyclohepta[1,2-d]thiazol-4-yl)-1-(2-(1-(1,1-dimethylethoxycarbonyl)pyrrolidinylmethyl)-4-methylthio-2(1H)-pyrimidinone To a solution of the product from step (i) (0.5 g) in N,N-dimethylformamide (6 ml) under nitrogen was added 60% sodium hydride (60 mg). After 15 min the product from step (ii) (0.5 g) was added and the whole heated at 50° C. for 14 h. A further aliquot of the product from step (ii) (1 g) was added and heating continued at 70° C. for 24 h. The reaction mixture was partitioned between ethyl acetate and brine. The organic phase was collected, dried (MgSO$_4$) and evaporated under reduced pressure to leave a yellow gum. Two diastereoisomers were separable by TLC using ethyl acetate as eluant. Purification and isolation of the less polar diastereoisomer was by chromatography eluting with ethyl acetate to give the subtitle product as a colourless foam.

Yield. 0.12 g MS: APCI (+ve); 572 (M+1, 30%), 471 (100%)

iv) (5S, 2R)-5-(7-Chloro-2-methyl-4H-benzo[5,6]cyclohepta[1,2-d]thiazol-4-yl)-1-(2-(pyrrolidinylmethyl)-4-methylthio-2(1H)-pyrimidinone trifluoroacetate.

Trifluoroacetic acid (4 ml) was added to a solution of the product from step (iii) (0.12 g) in dichloromethane (8 ml) under nitrogen. After 1 h the volatiles were evaporated under reduced pressure to leave a pale yellow gum. Yield. 0.12 g. Used directly in the next step.

v) (5S,2R)-5-(7-Chloro-2-methyl-4H-benzo[5,6]cyclohepta[1,2-d]thiazol-4-yl)-1-(2-(pyrrolidinylmethyl)-3,4-dihydro-4-thioxo-2(1H)-pyrimidinone The product from step (iv) (0.12 g) was dissolved in dry pyridine (15 ml) and triethylamine (10 ml) and treated with hydrogen sulphide gas bubbled through for 35 min. The volatiles were then removed under reduced pressure leaving a yellow gum. The title product was obtained by purification by chromatography eluting with ethyl acetate, methanol and triethylamine mixtures to give the product as a yellow solid.

Yield. 0.05 g MS: APCI (+ve); 457 (M+1, 100%), APCI (−ve); 455 (M−1, 100% 1HNMR δ (CDCl$_3$): 7.67 (d, 1H), 7.50 (s, 1H), 7.30 (m, 2H), 6.90 (dd, 2H), 6.11 (s, 1H), 3.75 (m, 2H), 3.55 (m, 1H), 3.0 (m, 2H), 2.0–1.6 (m, 4H) MP. 178° C.

EXAMPLE 40

(5S,2S)-5-(7-Chloro-2-methyl-4H-benzo[5,6]cyclohepta[1,2-d]thiazol-4-yl)-1-(2-(pyrrolidinylmethyl)-3,4-dihydro-4-thioxo-2(1H)-pyrimidinone i) (S)-N-(1,1-Dimethylethoxycarbonyl)-2-[[(4-methylsulphonyl)oxy]methyl]pyrrolidine The subtitle product was prepared from (S)-N-(1,1-dimethylethoxycarbonyl)-2-pyrrolidinemethanol (2.2 g) according to the method of example 39 step (ii) as a colourless oil. Yield: 3.8 g Used directly in the next step.

ii) (5S, 2S)-5-(7-Chloro-2-methyl-4H-benzo[5,6]cyclohepta[1,2-d]thiazol-4-yl)-1-(2-(1-(1,1-dimethylethoxycarbonyl)pyrrolidinylmethyl)-4-methylthio-2(1H)-pyrimidinone The subtitle compound was prepared from the products of example 39 step (i) (0.71 g) and the product of step (i) (3.8 g) according to the method of example 39 step (ii). Two diastereoisomers were separable by TLC using ethyl acetate as eluant. Purification and isolation of the more polar diastereoisomer was by chromatography eluting with ethyl acetate to give the subtitle product as a colourless foam.

Yield. 0.16 g MS: APCI (+ve); 572 (M+1, 30%), 471 (100%)

iii) (5S,2S)-5-(7-Chloro-2-methyl-4H-benzo[5,6]cyclohepta[1,2-d]thiazol-4-yl)-1-(2-pyrrolidinylmethyl)-4-methylthio-2(1H)-pyrimidinone trifluoroacetate The subtitle product was prepared from the product of step (ii) according to the method of example 39 step (iv). Yield. 0.16 g. Used directly in the next step.

iv) (5S,2S)-5-(7-Chloro-2-methyl-4H-benzo[5,6]cyclohepta[1,2-d]thiazol-4-yl)-1-(2-(pyrrolidinylmethyl)-3,4-dihydro-4-thioxo-2(1H)-pyrimidinone The title product was prepared from the product of step (iii) (0.16 g) according to the method of example 39 step (v). Purification was by chromatography eluting with ethyl acetate, methanol and triethylamine mixtures to give the product as a yellow solid.

Yield: 0.05 g MS: APCI (+ve); 457 (M+1, 100%), APCI (−ve); 455 (M−1, 100% 1HNMR δ (CDCl$_3$): 7.74 (d, 1H), 7.50 (s, 1H), 7.30 (m, 2H), 6.90 (dd, 2H), 6.18 (s, 1H), 3.85 (dd, 1H), 3.42 (m, 1H), 3.30 (m, 1H), 3.0–2.8 (m, 2H), 2.70 (s, 3H), 2.0–1.20 (m, 4H), MP. 235° C.

EXAMPLE 41

(±)-5-(7-Chloro-1-((imidazol-4-yl)ethyl)-2-methyl-4H-benzo[5,6]cyclohepta[1,2-d]imidazol-4-yl)-1-methyl-3,4-dihydro-4-thioxo-2(1H)-pyrimidinone i) 7-Chloro-1-((imidazol-4-yl)ethyl)-2-methyl-4H-benzo[5,6]cyclohepta[1,2-d]imidazol-4-one A mixture of the product from example 42 step (i) (1 g) and histamine (3 g) in 1-methyl-2-pyrrolidone (10 ml) was stirred at 100° C. for 4 hours. The mixture was diluted with water (10 ml) and the solid filtered. The solid was further washed with water and then dichloromethane to leave the subtitle product as a beige powder.

Yield: 0.986 g MS: APCI (+ve): 339 (M+1, 100%), APCI (−ve); 337 (M−1, 100%)

ii) (±)-7-Chloro-1-((imidazol-4-yl)ethyl)-2-methyl-4H-benzo[5,6]cyclohepta[1,2-d]imidazol-4-ol The subtitle product was prepared from the product of step (i) (0.966 g) and sodium borohydride (0.215 g) according the method of example 71 step (ii). Used directly in the next step.

iii) (±)-5-(7-Chloro-1-((imidazol-4-yl)ethyl)-2-methyl-4H-benzo[5,6]cyclohepta[1,2-d]imidazol-4-yl)-1-methyl-2,4(3H,4H)-pyrimidinedione The subtitle product was prepared from the product of step (ii) and 1-methyluracil (0.36 g) according to the method of example 42 step (iv). Purification was by biotage chromatography on silica eluting with 5% methanol in dichloromethane with 1% 0.880 ammonia present to give a white solid.

Yield: 0.756 g MS: APCI (+ve): 449 (M+1, 100%), APCI (−ve); 447 (M−1, 100%)

iv) (±)-5-(7-Chloro-1-((imidazol-4-yl)ethyl)-2-methyl-4H-benzo[5,6]cyclohepta[1,2-d]imidazol-4-yl)-1-methyl-3,4-dihydro-4-thioxo-2(1H)-pyrimidinone The title compound was prepared from the product of step (iii) (0.2 g) and Lawesson's reagent (0.9 g) according to the method of example 34 step (iv). Purification was by biotage chromatography on silica eluting with 5% methanol in dichloromethane with 1% 0.880 ammonia present to give a yellow glass.

Yield: 0.044 g MS: APCI (+ve); 465 (M+1, 100%), APCI (−ve); 463 (M−1, 100%) 1HNMR δ (DMSO): 12.6 (bs, 1H), 7.70 (d, 1H), 7.6 (s, 1H), 7.45 (d, 1H), 7.34 (dd, 1H), 7.17 (s, 1H), 6.78 (m, 3H), 5.74 (s, 1H), 4.20 (m, 2H), 3.22 (s, 3H), 2.84 (m, 2H), 2.17 (s, 3H)

EXAMPLE 42

(±)-5-(7-Chloro-1,2-dimethyl-4H-benzo[5,6]cyclohepta[1,2-d]imidazol-4-yl)-1-methyl-3,4-dihydro-4-thioxo-2(1H)-pyrimidinone i) 7-Chloro-2-methyl-4H-benzo[5,6]cyclohepta[1,2-d]oxazol-4-one A stirred solution of the product from example 25, step (vi) (10 g), and N-bromosuccinimide (7.19 g) in benzene (500 ml), was irradiated under a 500 Watt halogen lamp for 3.5 h. The mixture was then treated with triethylamine (11.25 ml), and further stirred for 16 h. The mixture was diluted with dichloromethane, washed with water, organic phase collected, dried (MgSO$_4$), and evaporated under reduced pressure. The residue was recrystallised from ethyl acetate to give the subtitled product as a beige crystalline solid.

Yield: 6 g MS: APCI (+ve); 246 (M+1, 100%)

ii) 7-Chloro-1,2-dimethyl-4H-benzo[5,6]cyclohepta[1,2-d]imidazol-4-one

A mixture of the product from step (i) (3.33 g), and 40% w/v aqueous methylamine solution was heated at 40° C. for 4 h. The solid was filtered and washed with water then dried under vacuum to give the subtitled product as a cream powder.

Yield: 2.1 g MS: APCI (+ve); 261 (M+1, 100%)

iii) (±)-7-Chloro-1,2-dimethyl-4H-benzo[5,6]cyclohepta[1,2-d]imidazol-4-ol

A mixture of the product from step (ii) (1.43 g), and sodium borohydride (0.42 g) in ethanol (100 ml) and dichloromethane (20 ml) were heated at 50° C. for 4 h. The solvents were evaporated under reduced pressure and the residue was dissolved in dichloromethane, washed with dilute aqueous sodium hydroxide solution, dried (CaCl$_2$), and evaporated to give the subtitled product as a brown solid.

Yield: 1.12 g MS: APCI (+ve); 243 (M+1, 100%)

iv) (±)-5-(7-Chloro-1,2-dimethyl-4H-benzo[5,6]cyclohepta[1,2-d]imidazol-4-yl)-1-methyl-2,4(1H,3H)-pyrimidinedione A mixture of the product from step (iii) (0.91 g), and 1-methyluracil (0.44 g) in acetonitrile (40 ml) was treated with boron trifluoride etherate (2.47 g) and heated at 50° C. for 4 h. The solution was treated with methanol (1 ml) and evaporated. Purification was by chromatography on a biotage silica column, using 3% methanol/0.1% 0.880 ammonia in dichloromethane as eluant to give the subtitled product as a cream powder.

Yield: 0.54 g MS: APCI (+ve); 369 (M+1, 100%)

v) (±)-5-(7-Chloro-1,2-dimethyl-4H-benzo[5,6]cyclohepta[1,2-d]imidazol-4-yl)-1-methyl-3,4-dihydro-4-thioxo-2(1H)-pyrimidinone A mixture of the product from step (iv) (0.535 g), and phosphorus pentasulphide (0.967 g) in 1,4-dioxane (10 ml) was heated at 100° C. for 3 h. The solvent evaporated and the residue dissolved in dichloromethane, washed with saturated aqueous sodium bicarbonate solution then with water, dried (MgSO$_4$) and evaporated. Purification was by chromatography on a biotage silica column, using 3% methanol/0.1% 0.880 ammonia in dichloromethane as eluant.

Yield: 0.3 g. MS: APCI (+ve): 385 (M+1, 100%), APCI (−ve): 383 (M−1, 100%) 1HNMR δ (DMSO): 7.67 (d, 1H), 7.44 (d, 1H), 7.32 (dd, 1H), 7.25 (s, 1H), 6.93 (d, 1H), 6.84 (d, 1H), 5.75 (s, 1H), 3.56 (s, 3H), 3.21 (s, 3H), 2.31 (s, 3H)

EXAMPLE 43

(S)-5-(7-Chloro-1,2-dimethyl-4H-benzo[5,6] cyclohepat[1,2-d]imidazol-4-yl)-1-methyl-3,4-dihydro-4-thioxo-2(1H)-pyrimidinone The title compound was obtained from the product of example 42 step (v) (0.3 g) by resolution of the racemate on HPLC (chiral-pak AD® column and ethanol as eluant). The title compound was the first enantiomer to be eluted off the column and was obtained as a yellow powder.

Yield: (0.090 g) MS: APCI (+ve); 385 (M+1, 100%), APCI (−ve): 383 (M−1, 100%) 1HNMR δ (DMSO): 7.67 (d, 1H), 7.44 (d, 1H), 7.32 (dd, 1H), 7.25 (s, 1H), 6.93 (d, 1H), 6.84 (d, 1H), 5.75 (s, 1H), 3.56 (s, 3H), 3.21 (s, 3H), 2.31 (s, 3H)

EXAMPLE 44

(±)-5-(2,7-Dichloro-4H-benzo[5,6]cyclohepta[1,2-d] thiazol-4-yl)-1-methyl-2,4(1H,3H)-pyrimidinedione i) 2-Amino-5-(2-(3-chlorophenyl)ethyl)-4-thiazolecarboxylic acid, methyl ester A solution of sodium methoxide (made from 1.43 g of sodium in dry methanol (20 ml) was added dropwise to a stirred solution of 2-(3-chlorophenyl)propanal (10.4 g) and methyl dichloroacetate (6.4 ml) in diethyl ether (30 ml) at 0° C. under nitrogen. After 1 h the mixture was quenched with brine and the product extracted into diethyl ether. The organic phase was collected, dried (MgSO$_4$) and evaporated under reduced pressure to leave a yellow oil. The oil and thiourea (4.72 g) were dissolved in methanol (40 ml) and the mixture set at reflux for 4 h. The solvent was removed under reduced pressure and the residue partitioned between ethyl acetate and saturated sodium bicarbonate solution. The organic phase was separated, washed with water, collected, dried (MgSO$_4$) and solvent evaporated under reduced pressure to leave a brown solid. The solid was triturated with isohexane and ethyl acetate mixtures and filtered to leave the subtitle product.

Yield: 5.9 g MS: APCI (+ve); 297/9 (M+1, 100%)

ii) 2-Chloro-5-(2-(3-chlorophenyl)ethyl)-4-thiazolecarboxylic acid, methyl ester Tert-Butylnitrite (4.5 ml) was added to a suspension of the product of step (i) (5.85 g) and anhydrous copper(II)chloride (4.03 g) in dry acetonitrile (50 ml) at room temperature over 0.5 hours. After a further 1 h the reaction mixture was quenched with 2M HCl and extracted with ethyl acetate. The organic phase was collected, dried (MgSO$_4$) and solvent evaporated under reduced pressure. Purification was by chromatography eluting with 10–15% ethyl acetate in isohexane.

Yield: 3.98 g MS:APCI (+ve); 316/8 (M+1, 100%)

iii) 2-Chloro-5-(2-(3-chlorophenyl)ethyl)-4-thiazolecarboxylic acid

The product from step (ii) (3.46 g) was treated with sodium hydroxide (0.7 g) in tetrahydrofuran (15 ml) and water (15 m) at room temperature. After 3 h the mixture was partitioned between 2M HCl and ethyl acetate. The organic phase was collected, dried (MgSO$_4$) and solvent evaporated under reduced pressure to leave a colourless solid.

Yield: 3.22 g MS:APCI (+ve); 300/2 (M+1, 100%)

iv) 2-Chloro-5-(2-(3-chlorophenyl)ethyl)-4-thiazolecarboxylic acid chloride

Oxalyl chloride (1.75 ml) was added to a solution of the product from step (iii) (3.14 g) in dichloromethane (30 ml) at room temperature containing 2 drops of dimethylformamide. After 4 h the volatiles were removed under reduced pressure to leave the subtitle product. Used directly in the next step.

v) 2,7-Dichloro-9,10-dihydro-4H-benzo[5,6]cyclohepta[1,2-d]thiazol-4-one

Aluminium chloride (5.3 g) was added to a solution of the product from step (iv) in dichloromethane (30 ml) at room temperature. After 3 h the mixture was poured onto 2M HCl/ice and the product extracted into ethyl acetate. The organic phase was collected, dried, (MgSO$_4$) and solvent evaporated under reduced pressure to leave a brown solid. This was triturated with isohexane/ethyl acetate and filtered to leave the subtitle product as a beige solid.

Yield: 1.93 g MS: APCI (+ve); 284/6 (M+1), 248/50 (100%)

vi) 2,7-Dichloro-4H-benzo[5,6]cyclohepta[1,2-d]thiazol-4-one

The product from step (v) (1.72 g) in 1,2-dichloroethane (30 ml) was treated with N-bromosuccinimide (1.08 g) with irradiation from a 500 Watt halogen lamp for 1.25 h. Triethylamine (8 ml) was then added and the mixture further stirred for 3 h. The subtitle product was obtained as the precipitated solid by filtration.

Yield: 1.27 g MS: APCI (+ve); 282/4 (M+1, 100%)

vii) (±)-2,7-Dichloro-4H-benzo[5,6]cyclohepta[1,2-d]thiazol-4-ol

Sodium borohydride (0.159 g) was added to a suspension of the product from step (vi) (1.27 g) in methanol (20 ml) and dichloromethane (5 ml) at room temperature. After 3 h the mixture was partitioned between 2N NaOH and dichloromethane. The organic phase was collected, dried, (MgSO$_4$) and solvent evaporated to leave a colourless foam. Yield: 1.27 g Used directly in the next step.

viii) (±)-5-(2,7-Dichloro-4H-benzo[5,6]cyclohepta[1,2-d]thiazol-4-yl)-1-methyl-2,4(1H,3H)-pyrimidinedione The title product was prepared from the product of step (vii) (1.27 g) and 1-methyluracil (1 g) according to the method of example 38 step (iv). Purification was by chromatography eluting with 50–60% ethyl acetate in isohexane.

Yield: 1.29 g MS: APCI (+ve); 392/4 (M+1, 100%) 1HNMR δ (DMSO): 11.28 (s, 1H), 7.57–7.47 (m, 3H), 7.12 (d, 1H), 7.04 (d, 1H), 6.87 (s, 1H), 5.51 (s, 1H), 3.14 (s, 3H)

EXAMPLE 45

(±)-5-(7-Chloro-4H-benzo[5,6]cyclohepta[1,2-d]thiazol-4-yl)-1-methyl-2,4(1H,3H)-pyrimidinedione Zinc powder (4 g) was added to a solution of the product from example 44 step (viii) (0.5 g) in acetic acid. After 24 h the solvent was evaporated under reduced pressure and the residue partitioned between saturated sodium bicarbonate solution and dichloromethane. The organic phase was collected, dried, (MgSO$_4$) and solvent evaporated to leave as a beige foam. Purification by trituration and filtration from isohexane/ethyl acetate mixtures gave the title product.

Yield: 0.44 g MS: APCI (+ve); 358 (M+1, 100%) 1HNMR δ (DMSO): 11.28 (s, 1H), 9.12 (s, 1H), 7.65–7.41 (m, 3H), 7.13 (d, 2H), 6.96 (s, 1H), 5.57 (s, 1H), 3.15 (s, 3H).

EXAMPLE 46

(±)-5-(7-Chloro-2-methoxy-4H-benzo[5,6]
cyclohepta[1,2-d]thiazol-4-yl)-1-methyl-2,4(1H,3H)-
pyrimidinedione The product from example 44 step (viii) (0.1 g) was heated with a solution of sodium methoxide (made from sodium (0.2 g) in dry methanol (10 ml)) at reflux for 3 h. The mixture was partitioned between ethyl acetate and water. The organic phase was collected, dried (MgSO$_4$) and solvent evaporated under reduced pressure. Purification was by chromatography eluting with 70% ethyl acetate in isohexane to give the title product as a colourless solid.

Yield: 0.025 g MS: APCI (+ve); 388/90 (M+1, 100%) 1HNMR δ (DMSO): 11.27 (s, 1H), 7.52–7.41 (m, 3H), 6.97 (d, 1H), 6.96 (s, 1H), 6.90 (d, 1H), 5.33 (s, 1H), 3.16 (s, 3H), 4.04 (s, 3H) MP: 150° C. (dec)

EXAMPLE 47

(±)-5-(7-Chloro-2-methylthio-4H-benzo[5,6]
cyclohepta[1,2d-]thiazol-4-yl)-1-methyl-2,4(1H,3H)-
pyrimidinedione The product from example 44 step (viii) (0.05 g) was treated with sodium methane thiolate (0.02 g) in dimethylformamide (2 ml) at room temperature. After 1 h the mixture was was partitioned between ethyl acetate and water. The organic phase collected, dried (MgSO$_4$) and solvent evaporated under reduced pressure. Purification was by precipitation with ethyl acetate/isohexane mixtures and filtration to give the title product.

Yield: 0.031 g MS:APCI (+ve); 404/6 (M+1, 100%) 1HNMR δ (DMSO): 11.28 (s, 1H), 7.53 (d, 1H), 7.52 (d, 1H), 7.44 (dd, 1H), 7.07–6.98 (d, 2H), 6.98 (s, 1H), 5.47 (s, 1H), 3.15 (s, 3H), 2.69 (s, 3H) MP: 214–6° C.

EXAMPLE 48

(±)-5-(2-Amino-7-chloro-4H-benzo[5,6]cyclohepta
[1,2-d]thiazol-4-yl)-1-methyl-2,4(1H,3H)-
pyrimidinedione The product from example 44 step (viii) (0.05 g) was heated with 0.88 ammonia (2 ml) and ethanol (1 ml) in a sealed tube at 100° C. for 24 h. The volatiles were removed under reduced pressure and the residue triturated with ethyl acetate and methanol mixtures to leave the title product as a yellow solid.

Yield: 0.008 g MS: APCI (+ve): 373/5 (M+100%) 1HNMR δ (DMSO): 11.22 (s, 1H), 7.45–7.34 (m, 3H), 7.30 (s, 2H), 6.93 (s, 1H), 6.67 (d, 2H), 5.21 (s, 1H), 3.15 (s, 3H) MP:>240° C.

EXAMPLE 49

(±)-5-(7-Chloro-2-methylamino-4H-benzo[5,6]
cyclohepta[1,2-d]thiazol-4-yl)-1-methyl-2,4(1H,3H)-
pyrimidinedione The product from example 44 step (viii) (0.05 g) was heated with 40% aq. Methylamine (4 ml) in ethanol (1 ml) for 3 hours. The mixture was partitioned between ethyl acetate and water. The organic phase was collected, dried (MgSO$_4$) and solvent evaporated under reduced pressure. The residue was triturated with ethyl acetate/iso-hexane mixtures and the title product collected by filtration as a pale yellow solid.

Yield: 0.033 g MS:APCI (+ve); 387/9; (M+1, 100%) 1HNMR δ (DMSO): 11.23 (s, 1H), 7.83 (brq, 1H), 7.46 (d, 1H), 7.42 (d, 1H), 7.36 (dd, 1H), 6.95 (s, 1H), 6.81 (d, 1H), 6.74 (d, 1H), 5.25 (s, 1H), 3.15 (s, 3H), 2.82 (d, 3H) MP: >240° C.

EXAMPLE 50

(±)-5-(7-Chloro-2-dimethylamino-4H-benzo[5,6]
cyclohepta[1,2-d]thiazol-4-yl)-1-methyl-2,4(1H,3H)-
pyrimidinedione The product from example 44 step (viii) (0.05 g) was heated with 40% aq. dimethylamine (2 ml) in ethanol (1 ml) for 1 hour. The mixture was partitioned between ethyl acetate and water. The organic phase was collected, dried (MgSO$_4$) and solvent evaporated under reduced pressure. The residue was triturated with ethyl acetate/isohexane mixtures and the title product collected by filtration as a pale yellow solid.

Yield: 0.031 g MS: APCI (+ve); 401/3 (M+1, 100%) 1HNMR δ (DMSO): 7.46 (d, 1H), 7.42 (d, 1H), 7.36 (dd, 1H), 6.96 (s, 1H), 6.86 (d, 1H), 6.76 (d, 1H), 5.28 (s, 1H), 3.15 (s, 3H), 3.04 (s, 6H) MP: >220° C.

EXAMPLE 51

(±)-5-(7-Chloro-2-(pyrrolidin-1-yl)-4H-benzo[5,6]
cyclohepta[1,2-d]thiazol-4-yl)-1-methyl-3,4-
dihydro-4-thioxo-2(1H)-pyrimidinone i) (±)-5-(7-Chloro-2-(pyrrolidin-1-yl)-4H-benzo[5,6] cyclohepta[1,2-d]thiazol-4-yl)-1-methyl-2,4(1H,3H)-pyrimidinedione The product from example 44 step (viii) (0.042 g) was treated with pyrrolidine (0.1 ml) in 1,4-dioxane (3 ml) at reflux for 6 h. The volatiles were removed under reduced pressure and the residue triturated with diethyl ether/isohexane mixtures to leave the subtitle product as a pale yellow solid.

Yield: 0.04 g MS:APCI (+ve); 427/9 (M+1, 100%)

ii) (±)-5-(7-Chloro-2-(pyrrolidin-1-yl)-4H-benzo[5,6] cyclohepta[1,2-d]thiazol-4-yl)-1-methyl-3,4-dihydro-4-thioxo-2(1H)-pyrimidinone The product from step (i) (0.04 g) was treated with Lawesson's reagent (0.037 g) according to the method of example 34 step (iv). Purification was by chromatography eluting with 1:1 ethyl acetate/isohexane to give the title product as a yellow solid.

Yield: 0.016 g MS: APCI (+ve); 443/5 (M+1, 100%), APCI (−ve); 441/3; (M−1, 100%) 1HNMR δ (CDCl$_3$): 11.60 (bs, 1H), 7.70 (d; 1H), 7.28 (m, 2H), 7.10 (s, 1H), 6.7 (dd, 2H), 6.09 (s, 1H), 6.30 (bs, 2H), 3.27 (s, 3H)

EXAMPLE 52

(±)-5-(7-Chloro-2-(N4-methyl-piperazin-1-yl))-4H-
benzo[5,6]cyclohepta[1,2-d]thiazol-4-yl)-1-methyl-
3,4-dihydro-4-thioxo-2(1H)-pyrimidinone i) (±)-5-(7-Chloro-2-(N4-methyl-piperazin-1-yl))-4H-benzo[5,6]cyclohepta[1,2-d]thiazol-4-yl)-1-methyl-2,4(1H, 3H)-pyrimidinedione The subtitle compound was prepared from the product of example 44 step (viii) (0.225 g) and N-methyl piperazine (0.32 ml) according to the method of example 51 step (i). Purification was by precipitation using ethyl acetate and isohexane with filtration to give the subtitle product as yellow solid.

Yield: 0.254 g MS: APCI (+ve); 456/8 (M+1, 100%)

ii) (±)-5-(7-Chloro-2-(N4-methyl-piperazin-1-yl))-4H-benzo[5,6]cyclohepta[1,2-d]thiazol-4-yl)-1-methyl-3,4-dihydro-4-thioxo-2(1H)-pyrimidinone The title product was prepared from the product of step (i) (0.225 g) and Lawesson's reagent (0.77 g) according to the method of example 34 step (iv). Purification was by chromatography eluting with dichloromethane/ethanol/triethylamine mixtures to give the title product as a yellow solid.

Yield. 0.086 g MS:APCI (+ve); 472/4 (M+1, 100%), APCI (−ve); (470/2; (M−1, 100%) 1HNMR δ (CDCl): 7.74 (d, 1H), 7.32 (dd, 1H), 7.30 (s, 1H), 7.10 (s, 1H), 6.72 (dd, 2H), 6.02 (s, 1H), 3.50 (m, 4H), 3.30 (s, 3H), 2.50 (t, 4H), 2.35 (s, 3H). rotamers

EXAMPLE 53

(±)-5-(7-Chloro-2-(2-(4-morpholinyl)ethylamino)-4H-benzo[5,6]cyclohepta[1,2-d]thiazol4-yl)-1-methyl-3,4-dihydro-4-thioxo-2(1H)-pyrimidinone i) (±)-5-(7-Chloro-2-(2-(4-morpholinyl)ethylamino)-4H-benzo[5,6]cyclohepta[1,2-d]thiazol-4-yl)-1-methyl-2,4(1H,3H)-pyrimidinedione The subtitle product was prepared from the product of example 44 step (viii) (0.225 g) and 4-(2-aminoethyl) morpholine (0.38 ml) according to the method of example 51 step (i). Purification was by precipitation using diethyl ether with filtration to give the subtitle product as yellow solid.

Yield: 0.162 g MS: APCI (+ve); 486/8 (M+1, 100%), APCI (−ve); 484/6 (M−1, 100%)

ii) (±)-5-(7-Chloro-2-(2-(4-morpholinyl)ethylamino)-4H-benzo[5,6]cyclohepta[1,2-d]thiazol-4-yl)-1-methyl-3,4-dihydro-4-thioxo-2(1H)-pyrimidinone The title product was prepared from the product of step (i) (0.162 g) and Lawesson's reagent (0.7 g) according to the method of example 34 step (iv). Purification was by chromatography eluting with dichloromethane/ethanol/triethylamine mixtures to give the title product as a yellow solid.

Yield. 0.074 g MS:APCI (+ve); 502/4 (M+1, 100%), 1HNMR δ (CDCl$_3$): 9.40 (bs, 1H), 7.72 (d, 1H), 7.30 (dd, 1H), 7.26 (s, 1H), 7.06 (s, 1H), 6.71 (dd, 2H), 6.07 (s, 1H), 3.80 (m, 4H), 3.40 (m, 2H), 3.30 (s, 3H), 3.15 (m, 2H), 2.50 (m, 4H) rotamers

EXAMPLE 54

(±)-5-(7-Chloro-4H-benzo[5,6]cyclohepta[1,2-d]thiazol4-yl)-1-methyl-3,4-dihydro-4-thioxo-2(1H)-pyrimidinone The title product was prepared from the product of example 45 step (i) (0.44 g) and Lawesson's reagent (1.5 g) according to the method of example 34 step (iv). Purification was by chromatography eluting with 7:3 ethyl acetate/isohexane to give the title product as a yellow solid.

Yield: 0.23 g MS: APCI (+ve); 374 (M+1, 100%) 1HNMR δ (CDCl$_3$): 9.4 (bs, 1H), 7.60 (d, 1H), 8.78 (s, 1H), 7.40 (m, 3H), 7.0 (s, 2H), 6.24 (s, 1H), 3.35 (s, 3H)

EXAMPLE 55

(S)-5-(7-Chloro-4H-benzo[5,6]cyclohepta[1,2-d]thiazol4-yl)-1-methyl-3,4-dihydro-4-thioxo-2(1H)-pyrimidinone The title compound was obtained from the product of example 54 by resolution of the racemate on HPLC (chiralpak AD® column and ethanol as eluant). The title compound was the second enantiomer to be eluted off the column and was obtained as a yellow powder.

MS:APCI (+ve); 374 (M+1, 100%) 1HNMR δ (CDCl$_3$): 9.45 (bs, 1H), 8.80 (s, 1H), 7.60 (d, 1H), 7.40 (m, 2H), 7.0 (s, 2H), 6.23 (s, 1H), 3.35 (s, 3H)

EXAMPLE 56

(±)-5-(2-Amino-7-Chloro-4H-benzo[5,6]cyclohepta[1,2-d]thiazol-4-yl)-1-methyl-3,4-dihydro-4-thioxo-2(1H)-pyrimidinone The title product was obtained from the product of example 48 (0.11 g) and Lawesson's reagent (0.6 g) according to the method of example 34 step (iv). Purification was by chromtography eluting with ethyl acetate to give the title product as yellow solid.

Yield: 0.01 g MS:APCI (+ve); 389 (M+1, 100%), APCI (−ve); 387 (M−1, 100%) 1HNMR δ (DMSO+CDCl$_3$): 11.60 (bs, 1H), 8.0 (bs, 1H), 7.70 (d, 1H), 7.30 (m, 2H), 7.10 (s, 1H), 6.7 (dd, 2H), 6.10 (s, 1H), 3.27 (s, 3H)

EXAMPLE 57

(±)-5-(7-chloro-2-methyl-4H-benzo[5,6]cyclohepta[1,2-d]thiazol-4-yl)-1-methyl-3,4-dihydro-4-thioxo-2(1H)-pyrimidinone A solution of the product of example 39 step (i) (0.1 g) together with methyl iodide (0.040 ml) and a 1M solution of potassium tert-butoxide in tetrahydrofuran (0.52 ml) in N,N-dimethylformamide (10 ml) was heated at 80° C. for 2 h. The reaction mixture was cooled, diluted with ethyl acetate and washed with saturated aqueous ammonium chloride and brine. The organic phase was dried over magnesium sulphate, filtered and evaporated. The crude product was purified by chromatography eluting with 5% ethanol in ethyl acetate to give a yellow oil (86 mg). This material was dissolved in a saturated blue solution of sodium hydrosulphide in N,N-dimethylformamide (3 ml) and heated at 80° C. for 3 h. The reaction mixture was cooled, diluted with dichloromethane and washed with water. The organic phase was dried over magnesium sulphate, filtered and evaporated. The crude product was purified by chromatography eluting with 30% isohexane in ethyl acetate to give the title compound as a yellow solid.

Yield: 0.02 g. MS: APCI (+ve): 388 (M+1, 100%). 1H NMR: δ (CDCl$_3$) 9.30 (br s, 1H), 7.68 (d, 1H), 7.36 (m, 2H), 7.17 (s, 1H), 6.91 (dd, 2H), 6.20 (s, 1H), 3.31 (s, 3H), 2.70 (s, 3H). MP: 305° C.

EXAMPLE 58

(±)-5-(7-Chloro-1-ethyl-2-methyl-4H-benzo[5,6]cyclohepta[1,2-d]imidazol-4-yl)-1-methyl-3,4-dihydro-4-thioxo-2(1H)-pyrimidinone i) (±)-5-(7-Chloro-1-ethyl-2-methyl-4H-benzo[5,6]cyclohepta[1,2-d]imidazol-4-yl)-1-methyl-2,4(1H,3H)-pyrimidinedione A solution of the product of example 42 step (i) (0.15 g) and diethylamine (0.157 g of a 70% solution in water) in butanol (0.5 ml) and N-methylpyrrolidinone (0.5 ml) was heated at 80° C. in a sealed tube for 24 h. The reaction mixture was cooled, diluted with ethanol (3 ml), sodium borohydride (0.070 g) added, and heated at 50° C. in a sealed tube for 3 h. The reaction was diluted with dichloromethane (50 ml), washed with pH5 phosphate buffer solution and brine, dried over magnesium sulphate and evaporated. The crude material was redissolved in acetonitrile (3 ml) and 1-methyl uracil (0.115 g) and boron trifluoride etherate (0.225 ml) added. The reaction was heated at 80° C. for 1 h before quenching with methanol (2 ml). After removal of solvent, the crude product was purified by chromatography eluting with 0.5% 880 ammonia, 4% methanol in dichloromethane to give the subtitle compound as a colourless oil.

Yield 0.068 g. MS: APCI (+ve) 384 (M+1) (100%)

ii) (±)-5-(7-Chloro-1-ethyl-2-methyl-4H-benzo[5,6]cyclohepta[1,2-d]imidazol-4-yl)-1-methyl-3,4-dihydro-4-thioxo-2(1H)-pyrimidinone A mixture of the product of step (i) (0.065 g) and Lawesson's reagent (0.343 g) in 1,4-dioxane (5 ml) was heated at reflux for 20 hours. The solvent was evaporated under reduced pressure and the residue partitioned between dichloromethane and water. Purification was by chromatography eluting with 0.2% 880 ammonia, 4% methanol in dichloromethane to give the title compound.

Yield: 0.047 g. MS: APCI (+ve): 399 (M+1, 100%). 1H NMR: δ (CDCl$_3$) 9.37 (br s, 1H), 7.75 (d, 1H), 7.29 (m, 2H), 7.03 (s, 1H), 6.77 (d, 1H), 6.66 (d, 1H), 6.01 (s, 1H), 3.98 (q, 2H), 3.26 (s, 3H), 2.43 (s, 3H), 1.33 (t, 3H). MP: 260–262° C. (dec).

EXAMPLE 59

(±)-5-(7-Chloro-1-cyclopropyl-2-methyl-4H-benzo[5,6]cyclohepta[1,2-d]imidazol-4-yl)-1-methyl-3,4-dihydro-4-thioxo-2(1H)-pyrimidinone i) (±)-5-(7-Chloro-1-cyclopropyl-2-methyl-4H-benzo[5,6]cyclohepta[1,2-d]imidazol-4-yl)-1-methyl-2,4(1H,3H)-pyrimidinedione A solution of the product of example 42 step (i) (0.15 g) and cyclopropylamine (0.140 g) in butanol (0.3 ml) and N-methylpyrrolidinone (0.3 ml) was heated at 80° C. in a sealed tube for 24 h. The reaction mixture was cooled, diluted with ethanol (3 ml), sodium borohydride (0.070 g) added, and heated at 50° C. in a sealed tube for 3 h. The reaction was diluted with dichloromethane (50 ml), washed with pH5 phosphate buffer solution and brine, dried over magnesium sulphate and evaporated. The crude material was redissolved in acetonitrile (3 ml) and 1-methyl uracil (0.115 g) and boron trifluoride etherate (0.225 ml) added. The reaction was heated at 80° C. for 1 h before quenching with methanol (2 ml). After removal of solvent, the crude product was purified by chromatography eluting with 0.5% 880 ammonia, 4% methanol in dichloromethane to give the title compound as a colourless oil.

Yield: 0.073 g. MS: APCI (+ve): 395 (M+1, 100%)

ii) (±)-5-(7-Chloro-1-cyclopropyl-2-methyl-4H-benzo[5,6]cyclohepta[1,2-d]imidazol-4-yl)-1-methyl-3,4-dihydro-4-thioxo-2(1H)-pyrimidinone A mixture of the product of step (i) (0.070 g) and Lawesson's reagent (0.350 g) in 1,4-dioxane (5 ml) was heated at reflux for 8 hours. The solvent was evaporated under reduced pressure and the residue partitioned between dichloromethane and water. Purification was by chromatography eluting with 0.2% 880 ammonia, 2% methanol in dichloromethane to give the title compound.

Yield: 0.043 g. MS: APCI (+ve): 411 (M+1, 100%). 1H NMR: δ (CDCl$_3$) 9.30 (br s, 1H), 7.74 (d, 1H), 7.30 (m, 2H), 7.04 (s, 1H), 6.96 (d, 1H), 6.76 (d, 1H), 5.99 (s, 1H), 3.27 (s, 3H), 3.10 (m, 1H), 2.50 (s, 3H), 1.20 (m, 2H), 0.98 (m, 2H).

MP: 295–298° C. (dec).

EXAMPLE 60

(±)-5-(7-Chloro-2-methyl-4H-benzo[5,6]cyclohepta[1,2-d]thiazol-4-yl)-1-(2-hydroxyethyl-3,4-dihydro-4-thioxo-2(1H)-pyrimidinone A solution of the product of example 39 step (i) (0.250 g) together with 2-bromoethanol (0.114 ml) and a 1M solution of potassium tert-butoxide in tetrahydrofuran (1.29 ml) in N,N-dimethylformamide (3 ml) was heated at 50° C. for 20 h. Sufficient sodium hydrosulphide was added to give a blue solution and the reaction mixture heated at 80° C. for 4 h. The reaction mixture was cooled, diluted with ethyl acetate and washed with saturated aqueous ammonium chloride. The organic phase was dried over magnesium sulphate, filtered and evaporated. The crude product was purified by chromatography eluting with 2% methanol in dichloromethane, followed by trituration with ethyl acetate to give the subtitle compound as a yellow solid.

Yield: 0.045 g. MS: APCI (+ve): 418 (M+1, 100%). 1H NMR: δ (CDCl$_3$) 9.52 (br s, 1H), 7.66 (d, 1H), 7.34 (m, 3H), 6.90 (dd, 2H), 6.16 (s, 1H), 3.83 (m, 4H), 2.69 (s, 3H).

EXAMPLE 61

(S)-5-(7-chloro-2-methyl-4H-benzo[5,6]cyclohepta[1,2-d]thiazol-4-yl)-1-(2-hydroxyethyl)-3,4-dihydro-4-thioxo-2(1H)-pyrimidinone The title compound was obtained from the product example 54 step by resolution of the racemate on HPLC (chiral-pak AD® column and ethanol as eluant). The title compound was the second enantiomer to be eluted off the column and was obtained as a yellow powder.

MS: APCI (+ve): 418 (M+1, 100%). 1H NMR: δ (CDCl$_3$) 9.52 (br s, 1H), 7.66 (d, 1H), 7.34 (m, 3H), 6.90 (dd, 2H), 6.16 (s, 1H), 3.83 (m, 4H), 2.69 (s, 3H).

EXAMPLE 62

(±)-5-(7-chloro-2-methyl-4H-benzo[5,6]cyclohepta[1,2-d]thiazol-4-yl)-1-(2-methoxyethyl)-3,4-dihydro-4-thioxo-2(1H)-pyrimidinone A solution of the product of example 39 step (i) (0.120 g) together with 2-bromoethyl methyl ether (0.073 ml) and a 1M solution of potassium tert-butoxide in tetrahydrofuran (0.62 ml) in N,N-dimethylformamide (3 ml) was heated at 50° C. for 20 h. Sufficient sodium hydrosulphide was added to give a blue solution and the reaction mixture heated at 80° C. for 4 h. The reaction mixture was cooled, diluted with ethyl acetate and washed with saturated aqueous ammonium chloride. The organic phase was dried over magnesium sulphate, filtered and evaporated. The crude product was purified by chromatography eluting with 1% methanol in dichloromethane, followed by trituration with ethyl acetate to give the title compound as a yellow solid.

Yield: 0.01 g. MS: APCI (+ve): 432 (M+1, 100%). 1HNMR: δ (CDCl$_3$) 9.31 (br s, 1H), 7.71 (d, 1H), 7.34 (m, 3H), 6.90 (dd, 2H), 6.20 (s, 1H), 3.93 (m, 1H), 3.76 (m, 1H), 3.53 (m, 2H), 3.31 (s, 3H), 2.69 (s, 3H).

EXAMPLE 63

(±)-5-(7-Chloro-2-[(phenylmethyl)amino]-4H-benzo[5,6]cyclohepta[1,2-d]thiazol-4-yl)-1-methyl-3,4-dihydro-4-thioxo-2(1H)-pyrimidinone i) (±)-5-(7-Chloro-2-[(phenylmethyl)amino]-4H-benzo[5,6]cyclohepta[1,2-d]thiazol-4-yl)-1-methyl-2,4(1H,3H)-pyrimidinedione A mixture of the product from example 44 step (viii) (0.25 g) and benzylamine (0.14 ml) in dry 1,4-dioxane (3 ml) were heated at 60° C. for 36 h. After this time benzylamine (0.14 ml) and dry dimethylsulphoxide (2 ml) were added and the mixture was heated at 60° C. for a further 72 h. The solvent was removed under reduced pressure. Purification was by trituration with diethyl ether and water.

Yield: 0.17 g. MS: APCI (+ve): 465/463 (M+1, 100%).

ii) (±)-5-(7-Chloro-2-[(phenylmethyl)amino]-4H-benzo[5,6]cyclohepta[1,2-d]thiazol-4-yl)-1-methyl-3,4-dihydro-4-thioxo-2(1H)-pyrimidinone The title compound was prepared from the product of step (i) (0.14 g) by the method of example 34 step (iv). Purification was by flash chromatography eluting with dichloromethane/20% ethyl acetate.

Yield 0.106 g. MS: APCI (+ve): 481/479 (M+1, 100%). 1H NMR: δ (DMSO) 12.65 (s, 1H), 8.42 (t, 1H), 7.64 (s, 1H), 7.54 (d, 1H), 7.43 (d, 1H), 7.35 (m, 5H), 6.86 (s, 2H), 5.69 (s, 1 H), 4.45 (m, 2H), 3.26 (s, 3H).

EXAMPLE 64

(±)-5-(7-Chloro-2-(cyclobutylamino)-4H-benzo[5,6]cyclohepta[1,2-d]thiazol-4-yl)-1-methyl-3,4-dihydro-4-thioxo-2(1H)-pyrimidinone i) (±)-5-(7-Chloro-2-(cyclobutylamino)-4H-benzo[5,6]cyclohepta[1,2-d]thiazol-4-yl)-1-methyl-2,4(1H,3H)-pyrimidinedione A mixture of the product from example 44 step (viii) (0.25 g) and cyclobutylamine (0.54 ml) in dry 1,4-dioxane (3 ml) were heated at 60° C. for 34 h. The solvent was removed under reduced pressure and the residue partitioned between water and ethyl acetate. The organic extracts were dried (MgSO$_4$) and evaporated under reduced pressure.

Yield 0.25 g. MS: APCI (+ve): 429/427 (M+1, 100%).

ii) (±)-5-(7-Chloro-2-(cyclobutylamino)-4H-benzo[5,6]cyclohepta[1,2-d]thiazol-4-yl)-1-methyl-3,4-dihydro-4-thioxo-2(1H)-pyrimidinone The title compound was prepared from the product of step (i) (0.21 g) by the method of example 34 step (iv). Purification was by flash chromatography eluting with dichloromethane/10% ethyl acetate.

Yield 0.109 g. MS: APCI (+ve): 445/443 (M+1, 100%). $^1$H NMR: δ (DMSO) 12.65 (s, 1H), 8.23 (d, 1H), 7.57 (t, 2H), 7.43 (d, 1H), 7.33 (d of d, 1H), 6.85 (q, 2H), 5.71 (s, 1H), 4.04 (sextet, 1H), 3.29 (s, 3H), 2.28 (m, 2H), 1.90 (m, 2H), 1.67 (m, 2H).

EXAMPLE 65

(±)-5-(7-Chloro-2-(cyclopropylamino)-4H-benzo[5,6]cyclohepta[1,2-d]thiazol-4-yl)-1-methyl-3,4-dihydro-4-thioxo-2(1H)-pyrimidinone i) (±)-5-(7-Chloro-2-(cyclopropylamino)-4H-benzo[5,6]cyclohepta[1,2-d]thiazol-4-yl)-1-methyl-2,4(1H,3H)-pyrimidinedione A mixture of the product from example 44 step (viii) (0.25 g) and cyclopropylamine (0.44 ml) in dry 1,4-dioxane (3 ml) was heated at 100° C. for 34 h. The solvent was removed under reduced pressure and the residue partitioned between water and ethyl acetate. The organic extracts were dried (MgSO$_4$) and evaporated under reduced pressure.

Yield: 0.25 g. MS: APCI (+ve): 415/413 (M+1, 100%).

ii) (±)-5-(7-Chloro-2-(cyclopropylamino)-4H-benzo[5,6]cyclohepta[1,2-d]thiazol-4-yl)-1-methyl-3,4-dihydro-4-thioxo-2(1H)-pyrimidinone The title compound was prepared from the product of step (i) (0.21 g) by the method of example 51 step (ii). Purification was by flash chromatography eluting with dichloromethane/2% ethanol.

Yield: 0.03 g. MS: APCI (+ve): 431/429 (M+1, 100%) 1HNMR δ (DMSO): 8.29 (s, 1H), 7.60 (d, 1H), 7.53 (s, 1H), 7.44 (d, 1H), 7.34 (dd, 1H), 6.91 (d, 1H), 6.84 (d, 1H), 5.79 (s, 1H), 3.26 (s, 3H), 0.72 (m, 2H), 0.51 (m, 2H)

EXAMPLE 66

(±)-5-(7-Chloro-2-(1,3,4-thiadiazolylthio)-4H-benzo[5,6]cyclohepta[1,2-d]thiazol-4-yl)-1-methyl-2,4(1H,3H)-pyrimidinedione To a mixture of the product from example 44 step (viii) (0.20 g) and 2-mercapto-1,3,4-thiadiazole (0.120 g) in dry dimethylformamide (2 ml) was added 60% sodium hydride (0.041 g). The mixture was stirred for 16 h then heated at 55° C. for 24 h. The reaction mixture was diluted with water and neutralised by the addition of acetic acid. The aqueous was extracted with dichloromethane and the combined organic extracts were dried (MgSO$_4$). The solvent was removed under reduced pressure and the residue purified by flash chromatography eluting with dichloromethane/5% ethanol.

Yield 0.135 g. MS: APCI (+ve): 476/474 (M+1, 100%). $^1$H NMR: δ (CDCl$_3$) 9.18 (s, 1H), 8.26 (s, 1H), 7.52 (d, 1H), 7.40 (d of d, 1H), 7.36 (d, 1H), 6.96 (d, 1H), 6.85 (d, 1H), 6.64 (s, 1H), 5.79 (s, 1H), 3.23 (s, 3H).

EXAMPLE 67

(±)-5-(7-Chloro-2-mercapto-4H-benzo[5,6]cyclohepta[1,2-d]thiazol-4-yl)-1-methyl-3,4-dihydro-4-thioxo-2(1H)-pyrimidinone i) (±)-S-(7-Chloro-2-(2-pyridinylthio)-4H-benzo[5,6]cyclohepta[1,2-d]thiazol4-yl)-1-methyl-2,4(1H,3H)-pyrimidinedione To a mixture of the product from example 44 step (viii) (0.20 g) and 2-mercapto-pyridine (0.113 g) in dry N,N-dimethylformamide (2 ml) was added 60% sodium hydride (0.041 g). The mixture was stirred for 16 h then heated at 55° C. for 2 h. The reaction mixture was diluted with water and neutralised by the addition of acetic acid. The aqueous was extracted with dichloromethane and the combined organic extracts were dried (MgSO$_4$). The solvent was removed under reduced pressure and the residue purified by flash chromatography eluting with dichloromethane/3% ethanol.

Yield: 0.15 g. MS: APCI (+ve): 469/467 (M+1, 100%).

ii) (±)-5-(7-Chloro-2-mercapto-4H-benzo[5,6]cyclohepta[1,2-d]thiazol-4-yl)-1-methyl-3,4-dihydro-4-thioxo-1(2H)-pyrimidinone The title compound was prepared from the product of step (i) (0.135 g) by the method of example 34 step (iv). Purification was by flash chromatography eluting with dichloromethane/15% ethyl acetate.

Yield: 0.038 g. MS: APCI (+ve): 408/406 (M+1, 100%). $^1$H NMR: δ (DMSO) 13.43 (s, 1H), 12.68 (s, 1H), 7.55 (m, 3H), 7.04 (d, 1H), 6.82 (s, 1H), 6.69 (d, 1H), 5.83 (s, 1H), 3.19 (s, 3H).

EXAMPLE 68

(±)-5-(7-Chloro-2-(imidazol-2-yl)thio)-4H-benzo[5,6]cyclohepta[1,2-d]thiazol-4-yl)-1-methyl-2,4-(1H,3H)-pyrimidinedione A suspension of sodium hydride (60% in oil, 20 mg) in N,N-dimethylformamide (2 ml) was treated with a solution of 2-mercaptoimidazole (50 mg) in N,N-dimethylformamide (2 ml). After 1 hour at room temperature a solution of example 44 step (viii) (200 mg) in N,N-dimethylformamide (2 ml) was added. The reaction mixture was heated at 60° C. for 18 hours, treated with a further equivalent of thiolate anion and heated at 60° C. for a further 8 hours. The reaction mixture was partitioned between ethyl acetate and dilute acetic acid. The organic phase was washed with water and brine, dried (MgSO$_4$) and evaporated. The product was purified by flash chromatography eluting with 0–2% methanol in dichloromethane.

Yield 0.13 g. MS: APCI (+ve) 456 (M+1, 100%) 1H NMR: δ (DMSO) 13.15 (br s, 1H), 11.28 (br s, 1H), 7.55–7.44 (m, 4H), 7.21 (s, 1H), 6.99 (s, 2H), 6.89 (s, 1H), 5.47 (s, 1H), 3.13 (s, 3H).

EXAMPLE 69

(±)-5-[7-Chloro-2-((1H-1,2,4-triazol-3-yl)thio)-4H-benzo[5,6]cyclohepta[1,2-d]thiazol-4-yl]-1-methyl-2,4(1H,3H)-pyrimidinedione The title compound was prepared from example 44 step (viii) (200 mg) and 3-mercapto-1,2,4-triazole (51 mg) according to the method of example 68.

Yield: 35 mg. MS: APCI (+ve) 457 (M+1, 100%) 1H NMR: δ (DMSO) 11.27 (br s, 1H), 8.79 (br s, 1H), 7.56–7.44 (m, 3H), 7.03 (s, 2H), 5.50 (s, 1H), 3.14 (s, 3H).

EXAMPLE 70

(±)-5-(7-Chloro-2-(imidazol-2-yl)thio)-4H-benzo[5,6]cyclohepta[1,2-d]thiazol-4-yl)-1-methyl-3,4-dihydro-4-thioxo-2(1H)-pyrimidinone The product from example 68 (0.18 g), and 1,2,4-triazole (0.3 g) was dissolved in dry acetonitrile (10 ml) and triethylamine (1 ml) under nitrogen at 0° C. Phosphorous oxychloride (0.072 ml) was added and the mixture stirred for a further 5 h. The reaction mixture was quenched with saturated sodium bicarbonate solution and extracted with dichloromethane (×3). The combined organic phases were collected, dried (MgSO$_4$) and solvents evaporated under reduced pressure to leave a colourless gummy solid. A solution of this solid in methanol (10 ml) was immediately added to a previously prepared saturated solution of hydrogen sulphide gas in methanol and triethylamine—(prepared by bubbling hydrogen sulphide gas through a solution of triethylamine (0.115 ml) in methanol (10 ml) for 20 min at room temperature). After stirring for 20 min the volatiles were removed under reduced pressure leaving a yellow gum. Purification was by chromatography eluting with ethyl acetate to give the product as a yellow solid.

Yield: 0.16 g MS:APCI (+ve): 472 (M+1, 100%), APCI (−ve); 470 (M−1, 100%) 1HNMR δ (CDCl$_3$): 9.62 (bs, 1H), 7.56 (d, 1H), 7.40 (d+s, 2H), 7.11 (s, 2H), 6.90 (s, 1H), 6.80 (dd, 2H), 6.39 (s, 1H), 3.27 (s, 3H) MP: 190° C.

EXAMPLE 71

(±)-5-(1-(2-Acetyloxyethyl)-7-chloro-2-methyl-4H-benzo[5,6]cyclohepta[1,2-d]imidazol-4-yl)-1-methyl-3,4-dihydro-4-thioxo-2(1H)-pyrimidinone i) 7-Chloro-1-(2-hydroxyethyl)-2-methyl-4H-benzo[5,6]cyclohepta[1,2-d]imidazol-4-one A mixture of the product from example 42 step (i) (1 g) and ethanolamine (10 ml) was stirred at 90° C. for 14 hours. The mixture was diluted with water (10 ml) and the solid filtered. The solid was further washed with water and then dichloromethane to leave the subtitle product as a beige powder.

Yield: 0.796 g MS: APCI (+ve): 289 (M+1, 100%)

ii) (±)-7-Chloro-1-(2-hydroxyethyl)-2-methyl-4H-benzo[5,6]cyclohepta[1,2-d]imidazol-4-ol A mixture of the product of step (i) (0.79 g) in ethanol (100 ml) was treated with sodium borohydride (0.207 g) followed by heating at reflux for 4 hours. The mixture was treated with a few drops of acetone and then concentrated under reduced pressure to dryness. Used directly in the next step.

MS: APCI (+ve); 243 (M−17, 100%).

iii) (±)-5-(7-Chloro-1-(2-hydroxyethyl)-2-methyl-4H-benzo[5,6]cyclohepta-[1,2-d]imidazol-4-yl)-1-methyl-2,4(1H,3H)-pyrimidinedione The subtitle compound was prepared from the product from step (ii) (1.85 g) and 1-methyluracil (0.4 g) according to the method of example 42 step (iv). Purification was by biotage chromatography on silica eluting with 5% methanol in dichloromethane with 1% 0.880 ammonia present.

Yield: 0.7 g MS: APCI (+ve); 399 (M+1, 100%)

iv) (±)-5-(1-(2-Acetyloxyethyl)-7-chloro-2-methyl-4H-benzo[5,6]cyclohepta[1,2-d]imidazol-4-yl)-1-methyl-2,4(1H,3H)-pyrimidinedione A solution of the product of step (iv) (0.75 g) in pyridine (5 ml) was treated with acetic anhydride (0.35 ml). After 4 hours the solvents were evaporated under reduced pressure. Purification was by biotage chromatography on silica eluting with 2–5% methanol in dichloromethane.

Yield: 0.701 g MS: APCI (+ve); 441 (M+1, 100%), APCI (−ve); 439 (M−1, 100%)

v) (±)-5-(1-(2-Acetyloxyethyl)-7-chloro-2-methyl-4H-benzo[5,6]cyclohepta[1,2-d]imidazol-4-yl)-1-methyl-3,4-dihydro-4-thioxo-2(1H)-pyrimidinone The title compound was prepared from the product of step (iv) (0.3 g) and Lawesson's reagent (1.376 g) according to the method of example 34 step (iv). Purification was by biotage chromatography on silica eluting with 3% methanol in dichloromethane with 1% 0.880 ammonia present to give a yellow glass.

Yield: 0.259 g MS: APCI (+ve); 457 (M+1, 100%), APCI (−ve); 455 (M−1, 100%) 1HNMR δ (DMSO): 12.62 (s, 1H), 7.68 (d, 1H), 7.46 (s, 1H), 7.33 (d, 1H), 7.25 (s, 1H), 6.95 (d, 1H), 6.86 (d, 1H), 5.74 (s, 1H), 4.41–4.11 (m, 4H), 3.22 (s, 3H), 2.34 (s, 3H), 1.89 (s, 3H)

EXAMPLE 72

(±)-5-(7-Chloro-1-(2-hydroxyethyl)-2-methyl-4H-benzo[5,6]cyclohepta[1,2-d]imidazol-4-yl)-1-methyl-3,4-dihydro-4-thioxo-2(1H-pyrimidinone The title compound was prepared from the product of example 71 step (v) (0.231 g) and lithium hydroxide monohydrate (0.045 g) in methanol (20 ml) and water (5 ml) according to the method of example 1 step (ix) as a yellow powder.

Yield: 0.144 g MS: APCI (+ve); 415 (M+1, 100%) 1HNMR δ (DMSO): 12.68 (s, 1H), 7.73 (d, 1H), 7.50 (d, 1H), 7.39 (dd, 1H), 7.29 (s, 1H), 7.02 (d, 1H), 6.88 (d, 1H), 5.80 (s, 1H), 5.02 (t, 1H), 4.12–4.04 (m, 2H), 3.72 (−3.63 (m, 2H), 3.26 (s, 3H), 2.40 (s, 3H),

EXAMPLE 73

(±)-5-(9-Chloro-3-methylbenzo[f]oxepano[3,4-d]imidazol-6-yl)-1-methyl-3,4-dihydro-4-thioxo-2(1H)-pyrimidinone i) Ethyl 2-bromo-5-bromomethyl-1-methylimidazole-4-carboxylate A mixture of ethyl 1,5-dimethylimidazole-4-carboxylate (*J. Org. Chem.*, 1982, 47, 144) (3.58 g) and N-bromosuccinimide (8.34 g) in ethyl acetate was irradiated with a 500 Watt halogen lamp for 3 h. The solvent was removed under reduced pressure and the residue purified by flash chromatography eluting with 5% ethyl acetate in dichloromethane.

Yield: 4.29 g. MS: APCI (+ve): 329/327 (M+1, 100%)/325 ii) Ethyl 2-bromo-5-(3-chlorophenoxy)methyl-1-methylimidazole-4-carboxylate

To a solution of 3-chlorophenol (1.73 g) in dry N,N-dimethylformamide (60 ml) was added 60% sodium hydride (0.535 g) in small portions. After the addition was complete the resultant solution was stirred at room temperature for 1 h. The product of step (i) (4.0 g) was added and the mixture was stirred at room temperature for 16 h. The solvent was removed under reduced pressure and the residue was partitioned between water and dichloromethane. The organic phase was washed with saturated potassium carbonate solution (×2), saturated brine (×2) and dried (MgSO$_4$). The solvent was removed under reduced pressure.

Yield: 4.8 g. MS: APCI (+ve): 377/375/373, 247/245 (100%).

iii) 2-Bromo-5-(3-chlorophenoxy)methyl-1-methylimidazole-4-carboxylic acid

A mixture of the product from step (ii) (4.8 g) and lithium hydroxide monohydrate (2.58 g) in tetrahydrofuran/water 1:1 (40 ml) was stirred at room temperature for 16 h. The solvent was removed under reduced pressure, the residue triturated with water and the resultant solid collected by filtration. This solid was partitioned between ethyl acetate and dilute hydrochloric acid, the organic phase was dried (MgSO$_4$) and the solvent removed under reduced pressure.

Yield 3.30 g. MS: APCI (+ve): 349/347/345, 331/329/327, 219 (100%)/217.

iv) 4,9-Dichloro-3-methylbenzo[f]oxepano[3,4-d]imidazol-6-one

A mixture of the product from step (iii) (1 g) and thionyl chloride (10 ml) were heated at 70° C. for 1 h. The thionyl chloride was evaporated under reduced pressure and the residue dissolved in dichloromethane (60 ml). Aluminium trichloride (1.55 g) was added and the mixture was stirred under nitrogen for 48 h. The reaction mixture was quenched with ice/water and the organic phase was separated. The aqueous layer was extracted with ethyl acetate, the combined organic extracts were dried (MgSO$_4$) and the solvent removed under reduced pressure.

Yield 0.64 g. MS: APCI (+ve): 285/283 (M+1, 100%).

v) (±)-4,9-Dichloro-3-methylbenzo[f]oxepano[3,4-d]imidazol-6-ol

To a solution of the product from step (iv) (0.64 g) in dichloromethane/methanol 1:1 (20 ml) was added sodium borohydride (0.11 g). After 2 h a further amount of sodium borohydride (0.11 g) was added. After 1 h water (20 ml) was added and the organic solvents were removed under reduced pressure. The aqueous residue was extracted with ethyl acetate and the combined organic extracts were dried (MgSO$_4$) and the solvent evaporated under reduced pressure.

Yield 0.52 g. MS: APCI (+ve): 287/285(M+1), 269/267 (100%).

vi) (±)-5-(4,9-Dichloro-3-methylbenzo[f]oxepano[3,4-d]imidazol-6-yl)-1-methyl-2,4(1H,3H)-pyrimidinedione The subtitle compound was prepared from the product of step (v) (0.52 g), 1-methyluracil (0.69 g) and boron trifluoride diethyletherate (2.3 ml) according to the method of example 42 step (iv). Purification was by flash chromatography eluting with 5% ethyl acetate in methanol.

Yield: 0.08 g. MS: APCI (+ve): 397/395/393 (M+1, 100%).

vii) (±)-5-(9-Chloro-3-methylbenzo[f]oxepano[3,4-d]imidazol-6-yl)-1-methyl-2,4(1H,3H)-pyrimidinedione The subtitle compound was prepared from the product of step (vi) (0.08 g) and zinc dust (5 g) according to the method of example 45. Purification was by flash chromatography eluting with dichloromethane/methanol/0.88 ammonia 93:5:2.

Yield 0.068 g. MS: APCI (+ve): 361/359 (M+1, 100%).

vii) (±)-5-(9-Chloro-3-methylbenzo[f]oxepano[3,4-d]imidazol-6-yl)-1-methyl-3,4-dihydro-4-thioxo-2(1H)-pyrimidinone The title compound was prepared from the product of step (vii) (0.053 g) by the method of example 34 step (iv). Purification was by flash chromatography eluting with dichloromethane/methanol/0.88 ammonia 94:5:1.

Yield: 0.023 g. MS: APCI (+ve): 377/375 (M+1, 100%). 1H NMR: δ (DMSO): 12.66 (s, 1H), 7.66 (d, 1H), 7.55 (s, 1 H), 7.51 (s, 1H), 7.20 (d, 1H), 7.14 (d of d, 1H), 5.64 (s, 1H), 5.52 (d, 1H), 4.92 (d, 1H), 3.48 (s, 3H), 3.28 (s, 3H).

PHARMACOLOGICAL DATA

The following examples describe the assay used to determine how strongly the compounds of the invention bind to P2-purinoceptor 7-TM G-protein coupled receptors. The assay used a human P2Y$_2$ receptor clone which was isolated from HL60 cells cDNA and then stably transfected into a Jurkat cell line (using methods described in "Cloning and Characterisation of a Bovine P$_{2Y}$ Receptor" Henderson et al (1995), 212, 2, 648–656; Parr et al Proc. Natl. Acad. Sci USA (1994), 91, 3275–3279 and Proc Natl Acad Sci USA (1994), 91, 13067). The cloned receptor mediates an increase in intracellular calcium in the cell line, which possesses no endogenous nucleotide receptor of its own.

1. The transfected Jurkat cells were maintained at a concentration of from about 1×10$^5$ to 10×10$^5$ cells/ml in RPMI containing 4% heat inactivated bovine serum, 2% penicillin/streptomycin and 1% glutamine. The cells were incubated at 37° C. in an atmosphere of air with 5% CO$_2$.

The cells were spun down at 1000 r.p.m. for 5 minutes and resuspended in 10 ml basal salt solution (BSS) containing 125 mM of NaCl, 5 mM of KCl, 1 mM of MgCl, 1.5 mM of CaCl$_2$, 25 mM of HEPES, 5 mM of glucose and 1 mg/ml of bovine serum albumin, having a pH of 7.3. The concentration of cells was determined using a Technicon cell counter. From 0.75×10$^8$ to 1×10$^8$ cells were spun down, resuspended to a concentration of 3.3× 10$^7$ cells/ml in BSS and incubated with either 17 μM fluo-3AM or 17 μM Fura-2AM at 37° C. for 35 minutes with vigorous shaking. The dye used was dependent upon the fluorescence and absorption properties of the compounds of the invention. In general for compounds of formula (I) wherein Q$^1$ is a S atom, fluo-3AM was used and for compounds wherein Q$^1$ is an O atom, either fluo-3AM or fura-2AM were used. The cells were again spun down and washed once with the same volume of BSS before being resuspended in BSS to a concentration of 1×10$^6$ cells/ml ready for testing.

When fluo-3AM was used as the dye, the cell solution was left at room temperature to recover for approximately 30 minutes before testing.

Fura-2AM loaded cells were divided into aliquots of about 10 ml and were warmed to 37° C. for 10 minutes before testing.

Calcium responses were measured on a SPEX Fluomax using 508 nm excitation and 525 nm emission wavelengths at room temperature for Fluo-3AM loaded cells and 340/380 nm excitation and 510 nm emission wavelengths for Fura-2AM loaded cells. Each cuvette contained 2 ml of cells and was stirred at high speed throughout the test. Basal fluorescence was measured for 5 seconds before 20 μl of a $10^{-2}$–$10^{-6}$M solution of the test compound in water was added to the 2 ml solution of the cells. The response was calibrated by the addition of Triton-X-100 (68 μl, 10% solution) and then EGTA (180 μl, 0.5 M solution). For each compound the response was compared to that of UTP.

or

2. The appropriate number of cells ($3\times10^7$ per plate) were spun down at 1000 r.p.m. for 5 minutes and resuspended in 10 ml of fresh RPMI at a concentration of $1\times10^7$ cell·ml$^{-1}$. The concentration of cells was determined using a Coulter cell counter. The cells were then incubated with 5 μM Fluo3-AM (TEFLABS) for 45 min. with vigorous shaking, 2 U·ml$^{-1}$ of apyrase (Sigma) was added after 30 min. The cells were spun down again, washed twice with 50 ml of BSS (basal salt solution containing 125 mM NaCl, 5 mM KCl, 1 mM MgCl$_2$, 1.5 mM CaCl$_2$, 25 mM HEPES, 5 mM glucose and 1 mg·ml$^{-1}$ bovine serum albumin, pH~7.3) before being resuspended in BSS to a concentration of $3\times10^6$ cells·ml$^{-1}$. The cells were then plated out (100 μl of cell suspension per well) in black, clear bottomed 96-well plates (Costar) before being spun down at 1000 r.p.m. for 5 minutes. Following a 15 min. recovery the plates were read at room temperature on a Fluorometric Imaging Plate Reader (FLIPR, Molecular Devices Corp.). Compound affinities were calculated either from inhibition of a UTP [A$_{50}$] or from the shift of a UTP concentration-effect curve.

The compounds exemplified have pA2 or PK$_B$ values greater than 4.0.

What is claimed is:

1. A compound of formula I or a salt thereof:

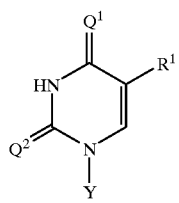

(I)

where

Y is hydrogen, $C_{1-4}$alkyl, $C_{1-4}$alkyl optionally substituted by hydroxy, alkoxy, amino, alkylamino, dialkylamino, phenyl, nitrogen and/or oxygen or optionally substituted by a $C_{3-8}$cycloalkyl ring which is optionally substituted by $C_{1-4}$alkyl; or Y is a group of formula (i):

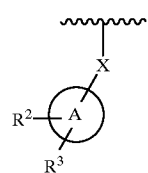

(i)

where

A is furan, oxazole, pyrimidine or phenyl;

$R^1$ is a group of formula (ii):

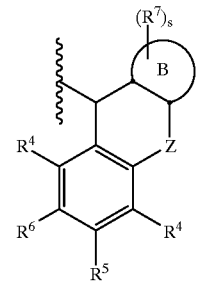

(ii)

where $R^4$ is hydrogen, halogen, $C_{1-3}$alkoxy, $C_{1-3}$alkylthio or $C_{1-3}$alkyl (optionally substituted by one or more fluorine atoms);

$R^5$ is hydrogen, hydroxy, halogen, $C_{1-3}$alkylthio, $C_{1-4}$alkyl (optionally substituted by one or more fluorine atoms), $C_{3-4}$cycloalkyl, MeOCH$_2$, MeSCH$_2$, phenyl, pyridyl, or $C_{1-3}$alkoxy; or $R^4$ and $R^5$ are —(CH$_2$)t- where t is 3 or 4 forming a fused ring;

$R^6$ is hydrogen, halogen, $C_{1-3}$alkoxy, $C_{1-3}$alkylthio, or $C_{1-3}$alkyl (optionally substituted by one or more fluorine atoms); or $R^5$ and $R^6$ are —(CH$_2$)t- where t is 3 or 4 forming a fused ring;

$R^7$ is hydrogen, hydroxy, $C_{1-3}$alkoxy, amino, hydroxyC$_{1-3}$alkyl, —NHC$_{1-3}$alkyl, —NC$_{1-3}$dialkyl, —NHC$_{3-8}$cycloalkyl, —N$_{3-8}$cycloalkyl, —NHphenyl, —NHC$_{1-3}$alkylphenyl, (heterocycle)C$_{1-3}$alkyl-, (heterocycle)C$_{1-3}$alkylthio-, (heterocycle)C$_{1-3}$alkyloxy-, (heterocycle)C$_{1-3}$alkylamino-, (heterocycle)thio-, (heterocycle)oxy-, (heterocycle)amino-, C$_{1-3}$alkylthio-, cyano, SH, C$_{1-3}$alkyl (optionally substituted by one or more fluorine atoms), —C$_{1-3}$alkylamino, —C$_{1-3}$alkylaminoalkyl, carboxamidoC$_{1-3}$alkyl, acetoxyC$_{1-3}$alkyl, or C$_{3-4}$cycloalkyl;

s is 1 or 2;

B is a 5 or 6 membered heterocyclic ring containing 1 to 3 heteroatoms selected from sulphur, oxygen or nitrogen;

X is a bond or a $C_{1-3}$alkylene group;

Z is a bond, —O—, —S—, —SO$_2$—, —CH$_2$—, —NH—, —Nalkyl-, —CH═CH—, —CF═CH—, —CH═CF—, —CF═CF—, —CH$_2$CH$_2$—, —CH═Calkyl-, —Calkyl═CH—, —CH═C(halogen)-, —C(halogen)═CH—, —NHCO—, —CONH—, —SO$_2$NH—, —NHSO$_2$—, or a group —R$^8$CH$_2$— or —CH$_2$R$^8$— where R$^8$ is NH, Nalkyl, NCOalkyl, CO, O or S;

$R^2$ is hydrogen, NO$_2$, NH$_2$, N(C$_{1-6}$alkyl)$_2$, CO$_2$H, CH$_2$OH, halogen, CO$_2$C$_{1-6}$alkyl, C$_{1-8}$alkyl optionally substituted by CO$_2$H or R$^2$ is hydroxy, imidazol-1-ylCH$_2$—, phenyl optionally substituted by CH$_2$CO$_2$H or CONR$^9$R$^{10}$ where R$^9$ and R$^{10}$ are independently hydrogen, C$_{1-6}$alkyl optionally substituted by hydroxy or CO$_2$H;

$R^3$ is hydrogen, R$^{11}$CO$_2$H, R$^{11}$PO(OH)$_2$, R$^{12}$tetrazol-5-yl, COR$^{13}$, NR$^{14}$R$^{15}$, CH$_2$NR$^{16}$CH$_2$CO$_2$H, C$_{1-8}$alkyl optionally substituted by CO$_2$H or R$^3$ is a group of formula (iii):

where D is a 4, 5 or 6 membered saturated ring containing a nitrogen optionally substituted by hydroxy and substituted by $CO_2H$ or CONH-het where het is tetrazol-5-yl or a thiazole or a thiadiazole ring, said thiadiazole ring being substituted by $CH_2CO_2H$ or D is a phenyl ring or a 5 membered aromatic heterocyclic ring containing 1–3 heteroatoms selected from nitrogen, oxygen or sulphur optionally substituted by one or more groups selected from $CF_3$, $CO_2H$, $CH_2OH$, $C_{1-6}$alkyl optionally interrupted by one or more oxygen atoms, $(CH_2)pCO_2H$, $C(CO_2H)=NOMe$, tetrazol-5-yl, $CH_2$tetrazol-5-yl, $CH_2CON(CH_2CO_2H)_2$, or $CH_2COR^{18}$;

where $R^{11}$ is $OCH_2$, $(CH_2)p$, $SCH_2$, $CONHCH_2$, NHCH $(R^{19})$ or $NR^{20}(CH_2)p$; $R^{12}$ is a bond, $(CH_2)p$, $OCH_2$, $SCH_2$, CONH, $CONHCH_2$, $CONHCH_2CONH$, $NHCH_2CONH$, $NHCH(R^9)$;

$R^{13}$ is OH, $N(CH_2CO_2H)_2$, $NHS(O)_2R^2$ or a group of formula (iv):

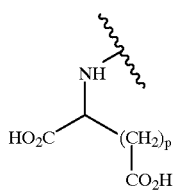

$R^{14}$ and $R^{15}$ are independently hydrogen, $CH_2CO_2H$, $CHPh_2$ or $C(=S)CH_2CH_2CO_2H$;

$R^{16}$ is hydrogen, $C_{1-6}$alkyl or $CO_2CH_2Ph$; $R^{17}$ is a bond, sulphur atom, CONH, $CH_2$, $CH_2O$, $OCH_2$, a group $-NR^{22}CH(CO_2H)CH_2-$ group or a group $CONR^{22}(CH_2)pCONR^{23}$ or $NR^{22}(CH_2)pCONR^{23}$;

$R^{18}$ is a group of formula (iv) as defined above or a group of formula (v):

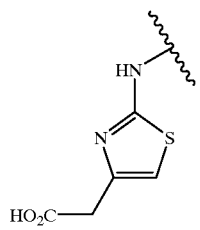

$R^{19}$ is hydrogen, $C_{1-6}$alkyl optionally substituted by hydroxy and/or optionally interrupted by oxygen, nitrogen or sulphur;

$R^{20}$ is hydrogen or $C_{1-6}$alkyl;

p is 1 or 2;

$R^{21}$ is $NH_2$ or $C_{1-6}$alkyl optionally interrupted by oxygen or nitrogen;

$R^{22}$ and $R^{23}$ are independently hydrogen, $C_{1-6}$alkyl; and $Q^1$ and $Q^2$ each independently represent an O or S atom.

2. A compound according to claim 1 in which Y is hydrogen, methyl, 2-(NN-dimethylamino)ethyl, 2-(N (pyrrolidinyl)ethyl, 2-(pyrrolidinyl)methyl, (1-methyl)-1H-imidazole-2ylmethyl, hydroxyethyl, methoxyethyl, or Y is a group of formula (i), and X is a bond or $CH_2$ group.

3. A compound according to claim 1 in which A is furan, oxazole, pyrimidine or phenyl.

4. A compound according to claim 1 in which $R^4$ is hydrogen and $R^6$ is hydrogen or methyl.

5. A compound according to claim 1 in which $R^5$ is hydrogen, chlorine, hydroxy or $C_{1-6}$alkyl.

6. A compound according to claim 1 in which $R^7$ is $C_{1-3}$ alkyl, hydrogen, chlorine, methoxy, methylthio, amino, methylamino, dimethylamino, pyrrolidin-1-yl, N-4-methyl-piperazin-1-yl, 2-(2-(4-morpholinyl)ethylamino, cyclopropyl, benzylamino, cyclobutylamino, cyclopropylamino, imidazol-2-ylthio, thiadiazol-2-ylthio, thiol, triazol-2-ylthio, imidazol-1-ylethoxy, acetoxyethyl, hydroxyethyl or imidazol-4-ylethyl.

7. A compound according to claim 1 in which B is pyridine, oxazole, thiazole or imidazole.

8. A compound according to claim 1 in which Z is $CH=CH$, $CH_2CH_2$ or $-CH_2O-$.

9. A compound according to claim 1 in which $R^2$ is hydrogen or $CO_2H$.

10. A compound according to claim 1 in which $R^3$ is hydrogen, a group of formula (iii) where D is a 4-membered saturated ring containing a nitrogen atom and substituted by $CO_2H$, or D is a 5-membered aromatic heterocycle containing 2 or 3 heteroatoms selected from nitrogen and sulphur and optionally substituted by $CH_2CO_2H$ or $CF_3$ and $R^{13}$ is a bond, CONH, $NHCH_2CONH$ or $CH_2$.

11. A compound according to claim 1 in which $Q^1$ is S and $Q^2$ is O or S.

12. A compound according to claim 1 which is:

(±)-5-[[5-(2-Ethyl-7-methyl-4H-benzo[5,6]cyclohepta[1,2-d]oxazol-4-yl)-3,4-dihydro-2,4-dioxo-1(2H)-pyrimidinyl]methyl]-2-furancarboxylic acid, (±)-2-[[5-(2-Ethyl-7-methyl-4H-benzo[5,6]cyclohepta[1,2-d]oxazol-4-yl)-3,4-dihydro-2-oxo-4-thioxo-1(2H)-pyrimidinyl]methyl]-4-oxazolecarboxylic acid, (±)-2-[2-[[4-[5-(7-Ethyl-2-methyl-4H-benzo[5,6]cyclohepta[1,2-d]oxazol-4-yl)-3,4-dihydro-2,4-dioxo-1(2H)-pyrimidinyl]pyrimidin-2-yl]amino]acetylamino]-4-thiazoleacetic acid, (±)-5-[[3,4-Dihydro-5-(2-methyl-4H-benzo[5,6]cyclohepta[1,2-d]oxazol-4-yl)-2-oxo-4-thioxo-1(2H)-pyrimidinyl]methyl]-2-furancarboxylic acid, (±)-N-[4-[3,4-Dihydro-5-(7-hydroxy-2-methyl-4H-benzo[5,6]cyclohepta[1,2-d]oxazol-4-yl)-2,4-dioxo-1(2H)-pyrimidinyl]pyrimidin-2-yl]-3-azetidinecarboxylic acid, (±)-2-[[5-(2-Ethyl-7-methyl-4H-benzo[5,6]cyclohepta[1,2-d]oxazol-4-yl)-3,4-dihydro-2-oxo-4-thioxo-1(2H)-pyrimidinyl]methyl]-N-[5-(trifluoromethyl)-1H-1,2,4-triazol-3-yl]-4-oxazolecarboxamide, (±)-3-[[5-(7-Ethyl-2-methyl-4H-benzo[5,6]cyclohepta[1,2-d]oxazol-4-yl)-3,4-dihydro-2-oxo-4-thioxo-1(2H)-pyrimidinyl]methyl]-5-[imidazol-1-ylmethyl]benzoic acid, (±)-2-[[5-(7-Ethyl-2-methyl-4H-benzo[5,6]cyclohepta[1,2-d]oxazol-4-yl)-3,4-dihydro-2-oxo-4-thioxo-1(2H)-pyrimidinyl]methyl]-4-oxazolecarboxylic acid, (±)-3-[[5-(7-Ethyl-2-methyl-4H-benzo[5,6]cyclohepta[1,2-d]oxazol-4-yl)-3,4-dihydro-2-oxo-4-thioxo-1(2H)-pyrimidinyl]methyl]benzoic acid, (±)-3-[[5-(7-Ethyl-2-methyl-4H-benzo[5,6]cyclohepta[1,2-d]oxazol-4-yl)-3,4-dihydro-2-oxo-4-thioxo-1(2H)pyrimidinyl]methyl]-N-[5-(trifluoromethyl)-1H-1,2,4-triazol-3-yl]benzenecarboxamide, (±)-3-[[5-(7-Ethyl-9,10-dihydro-2-methyl-4H-benzo[5,6]cyclohepta[1,2-d]oxazol-4-yl)-3,4-dihydro-2-oxo-4-thioxo-1(2H)-pyrimidinyl]methyl]benzoic acid, (±)-3-[[5-(7-Ethyl-2-methyl-4H-benzo[5,6]cyclohepta[1,2-d]thiazol-4-yl)-3,4-dihydro-2,4-dioxo-1(2H)-pyrimidinyl]methyl]benzoic acid, (±)-3-[[5-(2,7-Dimethyl-10H-benzo[4,5]cyclohepta[1,2-d]oxazol-10-yl)-3,4-dihydro-2-oxo-4-thioxo-1(2H)-pyrimidinyl]methyl]benzoic acid, (±)-5-(2,7-Dimethyl-4H-benzo[5,6]cyclohepta[1,2-d]oxazol-4-yl)-1-(3-methyl-5-(5-trifluoromethyl)-1H-1,2,4-triazol-3-yl)phenylmethyl-3,4-dihydro-4-thioxo-2(1H)pyrimidinone, (±)-3-[5-(2,7-Dimethyl-4H-benzo[5,6]cyclohepta[1,2-d]oxazol-4-yl)-3,4-dihydro-2-oxo-4-thioxo-1(2H)-pyrimidinylmethyl]benzoic acid, (±)-1-Methyl-5-(2,7-dimethyl-4H-benzo[5,6]cyclohepta[1,2-d]oxazol-4-yl)-3,4-dihydro-4-thioxo-2(1H)-pyrimidinone, (±)-1-Methyl-5-(2,6-dimethyl-4H-benzo[5,6]cyclohepta[1,2-d]oxazol-4-yl)-3,4-dihydro-4-thioxo-2(1H)-pyrimidinone, (±)-1-Methyl-5-(2,7-dimethyl-4H-benzo[5,6]cyclohepta[1,2-d]thiazol-4-yl)-3,4-dihydro-4-thioxo-2(1H)-pyrimidinone, (±)-1-Methyl-5-(2,7-dimethyl-10H-benzo[4,5]cyclohepta[1,2-d]oxazol-10-yl)-2,4-(1H,3H)-pyrimidinedione, (±)-1-Methyl-5-(2,7-dimethyl-10H-benzo[4,5]cyclohepta[1,2-d]oxazol-10-yl)-3,4-dihydro-2-oxo-4-thioxo-1(2H)-pyrimidine, (±)-1-Methyl-5-(2,7-dimethyl-10H-benzo[4,5]cyclohepta[1,2-d]thiazol-10-yl)-3,4-dihydro-4-thioxo-2(1H)-pyrimidinone, (±)-5-[8-Methyl-5H-benzo[4,5]cyclohepta[1,2-b]pyridin-5-yl]-3,4-dihydro-4-thioxo-2(1H)-pyrimidinone, (±)-1-Methyl-5-[8-Methyl-5H-benzo[4,5]cyclohepta[1,2-b]pyridin-5-yl]-3,4-dihydro-4-thioxo-2(1H)-pyrimidine, (±)-1-Methyl-5-[2,7-dimethyl-4H-benzo[5,6]cyclohepta[1,2-d]thiazol-4-yl]-2,4(1H,3H)-pyrimidinedione, (±)-5-[7-Chloro-2-methyl-4H-benzo[5,6]cyclohepta[1,2-d]oxazol-4-yl]-1-methyl-2,4(1H,3H)-pyrimidinedione, (±)-5-[7-Chloro-2-methyl-4H-benzo[5,6]cyclohepta[1,2-d]oxazol-4-yl]-1-methyl-3,4-dihydro-4-thioxo-2(1H)-pyrimidinone, (S)-5-[7-Chloro-2-methyl-4H-benzo[5,6]cyclohepta[1,2-d]oxazol-4-yl]-1-methyl-3,4-dihydro-4-thioxo-2(1H)-pyrimidinone, (±)-5-(7-Chloro-2-(2-(imidazol-1-yl)ethoxy)-4H-benzo[5,6]cyclohepta[1,2-d]thiazol-4-yl)-1-methyl-3,4-dihydro-4-thioxo-2(1H)-pyrimidinone, (±)-1-[(1-Methyl)-1H-imidazol-2-ylmethyl]-5-(2,6-dimethyl-4H-benzo[5,6]cyclohepta[1,2-d]oxazol-4-yl)-3,4-dihydro-4-thioxo-2(1H)-pyrimidinone, (±)-5-(2,7-Dimethyl-4H-benzo[5,6]cyclohepta[1,2-d]thiazol-4-yl)-1-(2-(N-pyrrolidinyl)ethyl)-3,4-dihydro-4-thioxo-2(1H)-pyrimidinone, (±)-5-(2-Ethyl-7-methyl-4H-benzo[5,6]cyclohepta[1,2-d]thiazol-4-yl)-3,4-dihydro-4-thioxo-2(1H)-pyrimidinone, (±) 5-(2-Ethyl-7-methyl-4H-benzo[5,6]cyclohepta[1,2-d]thiazol-4-yl)-1-(N-methyl)imidazol-2-ylmethyl)-3,4-dihydro-4-thioxo-2(1H)-pyrimidinone, (±)-5-(2-Ethyl-7-methyl-4H-benzo[5,6]cyclohepta[1,2-d]thiazol-4-yl)-1-(2-(N,N-dimethyl)ethyl)-3,4-dihydro-4-thioxo-2(1H)-pyrimidinone, (±)-5-[2-methyl-4H-benzo[5,6]cyclohepta[1,2-d]oxazol-4-yl)-1-methyl-3,4-dihydro-4-thioxo-2(1H)-pyrimidinone, (±)-1-Methyl-5-(2-methyl-7-ethyl-4H-benzo[5,6]cyclohepta[1,2-d]thiazol-4-yl)-3,4-dihydro-4-thioxo-2(1H)-pyrimidinone, (±)-1-Methyl-5-(2-methyl-7-n-propyl-4H-benzo[5,6]cyclohepta[1,2-d]thiazol-4-yl)-3,4-dihydro-4-thioxo-2(1H)-pyrimidinone, (±)-1-Methyl-5-(2-methyl-4H-benzo[5,6]cyclohepta[1,2-d]imidazol-4-yl)-3,4-dihydro-4-thioxo-2(1H)-pyrimidinone, (±)-5-(7-Chloro-2-methyl-4H-benzo[5,6]cyclohepta[1,2-d]thiazol-4-yl)-3,4-dihydro-4-thioxo-2(1H)-pyrimidinone, (5S,2R)-5-(7-Chloro-2-methyl-4H-benzo[5,6]cyclohepta[1,2-d]thiazol-4-yl)-1-(2-pyrrolidinylmethyl)-3,4-dihydro-4-thioxo-2(1H)-pyrimidinone, (5S,2S)-5-(7-Chloro-2-methyl-4H-benzo[5,6]cyclohepta[1,2-d]thiazol-4-yl)-1-(2-(pyrrolidinylmethyl)-3,4-dihydro-4-thioxo-2(1H)-pyrimidinone, (±)-5-(7-Chloro-1-((imidazol-4-yl)ethyl)-2-methyl-4H-benzo[5,6]cyclohepta[1,2-d]imidazol-4-yl)-1-methyl-3,4-dihydro-4-thioxo-2(1H)-pyrimidinone, (±)-5-(7-Chloro-1,2-dimethyl-4H-benzo[5,6]cyclohepta[1,2-d]imidazol-4-yl)-1-methyl-3,4-dihydro-4-thioxo-2(1H)-pyrimidinone, (S)-5-(7-Chloro-1,2-dimethyl-4H-benzo[5,6]cyclohepat[1,2-d]imidazol-4-yl)-1-methyl-3,4-dihydro-4-thioxo-2(1H)-pyrimidinone, (±)-5-(2,7-Dichloro-4H-benzo[5,6]cyclohepta[1,2-d]thiazol-4-yl)-1-methyl-2,4(1H,3H)-pyrimidinedione, (±)-5-(7-Chloro-4H-benzo[5,6]cyclohepta[1,2-d]thiazol-4-yl)-1-methyl-2,4(1H,3H)-pyrimidinedione (±)-5-(7-Chloro-2-methoxy-4H-benzo[5,6]cyclohepta[1,2-d]thiazol-4-yl)-1-methyl-2,4(1H,3H)-pyrimidinedione, (±)-5-(7-Chloro-2-methylthio-4H-benzo[5,6]cyclohepta[1,2-d]thiazol-4-yl)-1-methyl-2,4(1H,3H)-pyrimidinedione, (±)-5-(2-Amino-7-chloro-4H-benzo[5,6]cyclohepta[1,2-d]thiazol-4-yl)-1-methyl-2,4(1H,3H)-pyrimidinedione, (±)-5-(7-Chloro-2-methylamino-4H-benzo[5,6]cyclohepta[1,2-d]thiazol-4-yl)-1-methyl-2,4(1H,3H)-pyrimidinedione, (±)-5-(7-Chloro-2-dimethylamino-4H-benzo[5,6]cyclohepta[1,2-d]thiazol-4-yl)-1-methyl-2,4(1H,3H)-pyrimidinedione, (±)-5-(7-Chloro-2-(pyrrolidin-1-yl)-4H-benzo[5,6]cyclohepta[1,2-d]thiazol-4-yl)-1-methyl-3,4-dihydro-4-thioxo-2(1H)-pyrimidinone, (±)-5-(7-Chloro-2-(N4-methyl-piperazin-1-yl))-4H-benzo[5,6]cyclohepta[1,2-d]thiazol-4-yl)-1-methyl-3,4-dihydro-4-thioxo-2(1H)-pyrimidinone, (±)-5-(7-Chloro-2-(2-(4-morpholinyl)ethylamino)-4H-benzo[5,6]cyclohepta[1,2-d]thiazol-4-yl)-1-methyl-3,4-dihydro-4-thioxo-2(1H)-pyrimidinone, (±)-5-(7-Chloro-4H-benzo[5,6]cyclohepta[1,2-d]thiazol-4-yl)-1-methyl-3,4-dihydro-4-thioxo-2(1H)-pyrimidinone, (S)-5-(7-Chloro-4H-benzo[5,6]cyclohepta[1,2-d]thiazol-4-yl)-1-methyl-3,4-dihydro-4-thioxo-2(1H)-pyrimidinone, (±)-5-(2-Amino-7-Chloro-4H-benzo[5,6]cyclohepta[1,2-d]thiazol-4-yl)-1-methyl-3,4-dihydro-4-thioxo-2(1H)-pyrimidinone, (±)-5-(7-chloro-2-methyl-4H-benzo[5,6]cyclohepta[1,2-d]thiazol-4-yl)-1-methyl-3,4-dihydro-4-thioxo-2(1H)-pyrimidinone, (±)-5-(7-Chloro-1-ethyl-2-methyl-4H-benzo[5,6]cyclohepta[1,2-d]imidazol-4-yl)-1-methyl-3,4-dihydro-4-thioxo-2(1H)-pyrimidinone, (±)-5-(7-Chloro-1-cyclopropyl-2-methyl-4H-benzo[5,6]cyclohepta[1,2-d]imidazol-4-yl)-1-methyl-3,4-dihydro-4-thioxo-2(1H)-pyrimidinone, (±)-5-(7-Chloro-2-methyl-4H-benzo[5,6]cyclohepta[1,2-d]thiazol-4-yl)-1-(2-hydroxyethyl-3,4-dihydro-4-thioxo-2(1H)-pyrimidinone, (S)-5-(7-chloro-2-methyl-4H-benzo[5,6]cyclohepta[1,2-d]thiazol-4-yl)-1-(2-hydroxyethyl)-3,4-dihydro-4-thioxo-2(1H)-pyrimidinone, (±)-5-(7-chloro-2-methyl-4H-benzo[5,6]cyclohepta[1,2-d]thiazol-4-yl)-1-(2-methoxyethyl)-3,4-dihydro-4-thioxo-2(1H)-pyrimidinone, (±)-5-(7-Chloro-2-[(phenylmethyl)amino]-4H-benzo[5,6]cyclohepta[1,2-d]thiazol-4-yl)-1-methyl-3,4-dihydro-4-thioxo-2(1H)-pyrimidinone, (±)-5-(7-Chloro-2-(cyclobutylamino)-4H-benzo[5,6]cyclohepta[1,2-d]thiazol-4-yl)-1-methyl-3,4-dihydro-4-thioxo-2(1H)-pyrimidinone, (±)-5-(7-Chloro-2-(cyclopropylamino)-4H-benzo[5,6]cyclohepta[1,2-d]thiazol-4-yl)-1-methyl-3,4-dihydro-4-thioxo-2(1H)-pyrimidinone, (±)-5-(7-Chloro-2-(1,3,4-thiadiazolylthio)-4H-benzo[5,6]cyclohepta[1,2-d]thiazol-4-yl)-1-methyl-2,4(1H,3H)-pyrimidinedione, (±)-5-(7-Chloro-2-mercapto-4H-benzo[5,6]cyclohepta[1,2-d]thiazol-4-yl)-1-methyl-3,4-dihydro-4-thioxo-2(1H)-pyrimidinone, (±)-5-(7-Chloro-2-((imidazol-2-yl)thio)-4H-benzo[5,6]cyclohepta[1,2-d]thiazol-4-yl)-1-methyl-2,4-(1H,3H)-pyrimidinedione, (±)-5-[7-Chloro-2-((1H-1,2,4-triazol-3-yl)thio)-4H-benzo[5,6]cyclohepta[1,2-d]thiazol-4-yl]-1-methyl-2,4(1H,3H)-pyrimidinedione, (±)-5-(7-Chloro-2-((imidazol-2-yl)thio)-4H-benzo[5,6]cyclohepta[1,2-d]thiazol-4-yl)-1-methyl-3,4-dihydro-4-thioxo-2(1H)-pyrimidinone, (±)-5-(1-(2-Acetyloxyethyl)-7-chloro-2-methyl-4H-benzo[5,6]cyclohepta[1,2-d]imidazol-4-yl)-1-methyl-3,4-dihydro-4-thioxo-2(1H)-pyrimidinone, (±)-5-(7-Chloro-1-(2-hydroxyethyl)-2-methyl-4H-benzo[5,6]cyclohepta[1,2-d]imidazol-4-yl)-1-methyl-3,4-dihydro-4-thioxo-2(1H)-pyrimidinone, (±)-5-(9-Chloro-3-methylbenzo[f]oxepano[3,4-d]imidazol-6-yl)-1-methyl-3,4-dihydro-4-thioxo-2(1H)-pyrimidinone, and pharmaceutically acceptable salts thereof.

13. A pharmaceutical composition comprising a compound of formula I or a salt or solvate thereof as defined in claim 1 in association with a pharmaceutically acceptable adjuvant, diluent or carrier.

14. A process for the preparation of compounds of formula I as defined in claim 1 which comprises:

(a) reacting a compound of formula (II):

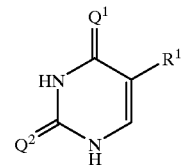

(II)

where $Q^1$ and $Q^2$ are as defined in formula (I) and $R^1$ is as defined in formula (I) or is a protected derivative thereof with a compound of formula (III):

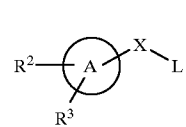

(III)

where $R^2$, $R^3$ and A are as defined in formula (I) or are protected derivatives thereof, X is as defined in formula (I) and L is a leaving group, or (b) reacting a compound of formula (IV):

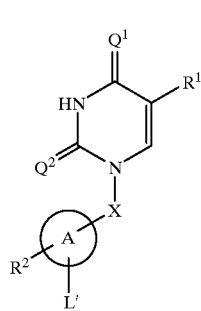

(IV)

where $Q^1$, $Q^2$, $R^1$ and X are as defined in formula (I), $R^2$ and A are as defined in formula (I) or are protected derivatives thereof and L' is a leaving group with a compound of formula (V), (VI) or (VII):

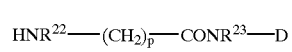

(V)

$$HNR^{22}-(CH_2)_{\overline{p}}-CONR^{23}-D$$

(VI)

$$HNR^{22}-CH(CO_2H)-CH_2-D$$

(VII)

where $R^{22}$, $R^{23}$ and p are as defined in formula (I) and D is as defined in formula (I) or is a protected derivative thereof, or (c) when $R^3$ is a group $-R^{11}-CO_2H$ and $R^{11}$ is $SCH_2$ or $NR^{20}(CH_2)_p$, reacting a compound of formula (iv) as defined above with a compound $H-R^{11}-CO_2R^{24}$ where $R^{11}$ is $SCH_2$ or $NR^{20}(CH_2)_p$ and $R^{24}$ is hydrogen or an ester forming group; and optionally thereafter (a), (b) or (c) in any order:

removing any protecting groups forming a salt.

15. A method of treating an inflammatory condition selected from the group consisting of asthma, inflammatory bowel disease, rheumatoid arthritis and osteoarthritis, which comprises the step of administering to a patient in need of such treatment an effective amount of a compound of formula (I).

16. A method according to claim 15, where said compound of formula (I) is co-administered with another anti-inflammatory agent.

* * * * *